(12) United States Patent
Fangrow, Jr.

(10) Patent No.: US 8,469,939 B2
(45) Date of Patent: Jun. 25, 2013

(54) VIAL ADAPTOR

(75) Inventor: Thomas F. Fangrow, Jr., Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 821 days.

(21) Appl. No.: 12/388,430

(22) Filed: Feb. 18, 2009

(65) Prior Publication Data
US 2009/0216212 A1  Aug. 27, 2009

Related U.S. Application Data

(60) Provisional application No. 61/029,542, filed on Feb. 18, 2008.

(51) Int. Cl.
*A61B 19/00* (2006.01)
*A61M 5/32* (2006.01)

(52) U.S. Cl.
USPC .......................................... 604/411; 604/406

(58) Field of Classification Search
USPC ................................................ 604/403–416
See application file for complete search history.

(56) References Cited

U.S. PATENT DOCUMENTS

| | | |
|---|---|---|
| 3,852,385 A | 12/1974 | Huggins |
| 4,128,098 A | 12/1978 | Bloom et al. |
| 4,296,786 A | 10/1981 | Brignola |
| 4,675,020 A | 6/1987 | McPhee |
| 4,759,756 A | 7/1988 | Forman et al. |
| 4,997,430 A | 3/1991 | Van der Heiden et al. |
| 5,061,264 A * | 10/1991 | Scarrow .................... 604/408 |
| 5,279,576 A | 1/1994 | Loo et al. |
| 5,334,179 A | 8/1994 | Poli et al. |
| RE35,167 E | 3/1996 | Mouchawar et al. |
| 5,526,853 A | 6/1996 | McPhee et al. |

(Continued)

FOREIGN PATENT DOCUMENTS

| | | |
|---|---|---|
| EP | 0 446 463 A1 | 12/1990 |
| WO | WO 03/066152 A2 | 8/2003 |
| WO | WO 03/066152 A3 | 8/2003 |
| WO | WO 2005/105014 | 11/2005 |

OTHER PUBLICATIONS

Baxter, *Catalog: IV Sets and Access Devices*, Baxter Healthcare Corporation, Medication Delivery, Route 120 and Wilson Road Round Lake, IL 60073; Lit # 6000054, Dec. 2002, 4 pages.

ICUMED, *Advertisement: Clave® Pump Port Spike*, San Clemente, CA 92673, I1-1152, Aug. 2004, 1 page.

(Continued)

*Primary Examiner* — Philip R Weist
(74) *Attorney, Agent, or Firm* — Knobbe Martens Olson & Bear LLP

(57) ABSTRACT

A vial adaptor configured to be attached to a wide range of vial sizes, the adaptor being configured to penetrate the vial seal so that the contents of a vial can be removed. The vial adaptor can have a body portion, a penetrating portion projecting from the body portion and configured to be inserted through the seal and positioned within an interior space of the vial so that the contents of the vial can flow through an opening in the penetrating portion, an interface portion supported by the body portion that is connectable to a syringe or other medical implement, at least one deflectable tab configured be bendable by hand or to bend in response to contact with the vial. The vial can also have a filtered air vent to allow air to fill the vial as the contents thereof are being removed.

28 Claims, 30 Drawing Sheets

U.S. PATENT DOCUMENTS

| | | | |
|---|---|---|---|
| 5,641,010 | A | 6/1997 | Maier |
| 6,142,446 | A | 11/2000 | Leinsing |
| 6,666,852 | B2 | 12/2003 | Niedospial, Jr. |
| 6,875,205 | B2 | 4/2005 | Leinsing |
| 7,354,427 | B2 | 4/2008 | Fangrow |
| 2003/0153895 | A1 | 8/2003 | Leinsing |
| 2005/0148994 | A1 | 7/2005 | Leinsing |
| 2006/0089594 | A1 | 4/2006 | Landau |
| 2007/0106244 | A1* | 5/2007 | Mosler et al. ............... 604/411 |
| 2007/0156112 | A1 | 7/2007 | Walsh |
| 2007/0244447 | A1 | 10/2007 | Capitaine et al. |
| 2008/0009789 | A1 | 1/2008 | Zinger et al. |
| 2008/0015496 | A1 | 1/2008 | Hamedi-Sangsari |
| 2008/0172024 | A1* | 7/2008 | Yow ............... 604/411 |

OTHER PUBLICATIONS

Injex the Soft Shot, *Needle Free Injector System: Vial Adapter*, © Injex—Equidyne Systems, http://www.injex.com/products/injex30.asp, pp. 3-4.

Bioject Products, *Bioject Needle—Free Injection Systems*, © Bioject, http://www.bioject.com/products.html, 2 pages.

Children with Diabetes, *Gentle Jet Injector*, © 1995-2008 Diabetes123 and with Children, http://www.childrenwithdiabetes.com/d_06_352.htm, 4 pages.

Medi-Jector, *The Medi-Jector VISION® Injector*, © 2005 Antares Pharma Inc., http://www.medijector.com/how_it_works/products.htm, 2 pages.

European Patent Office; "Notification of Transmittal of the International Search Report and the Written Opinion of the International Searching Authority, or the Declaration", "International Search report", and "Written Opinion of the International Searching Authority" of PCT/US2009/034426, filed Feb. 18, 2009; mailed May 25, 2009.

International Preliminary Report on Patentability and Written Opinion, regarding Application No. PCT/US2009/034426, in 6 pages, dated Aug. 24, 2010.

\* cited by examiner

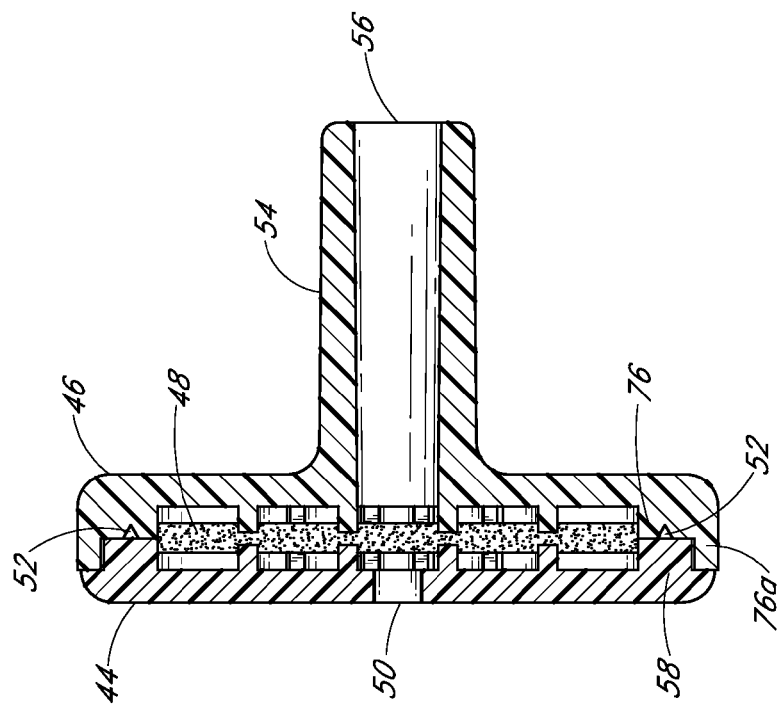
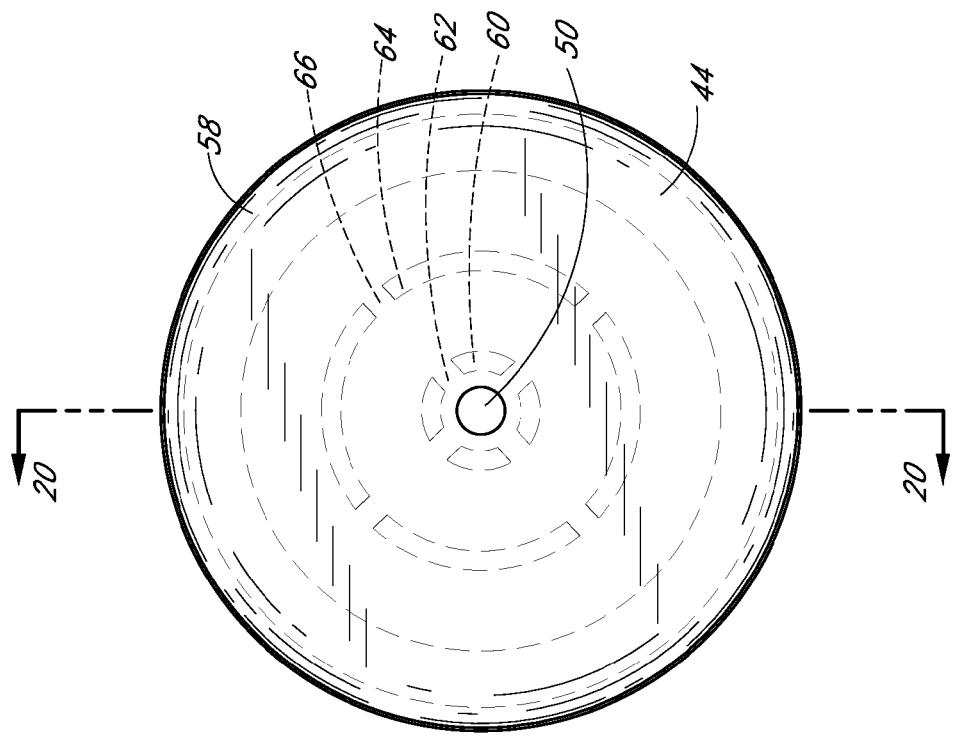
FIG. 20
FIG. 19

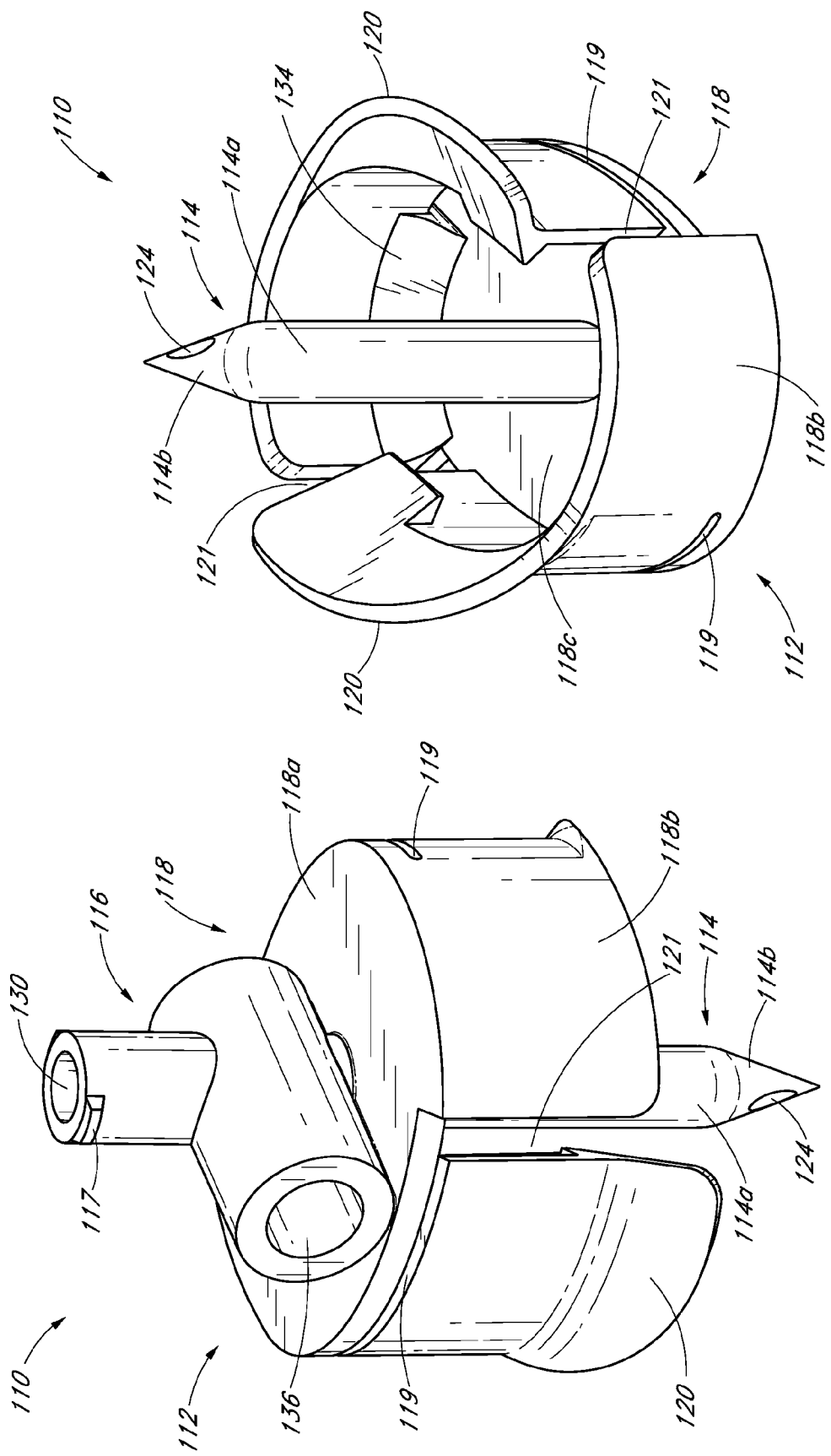

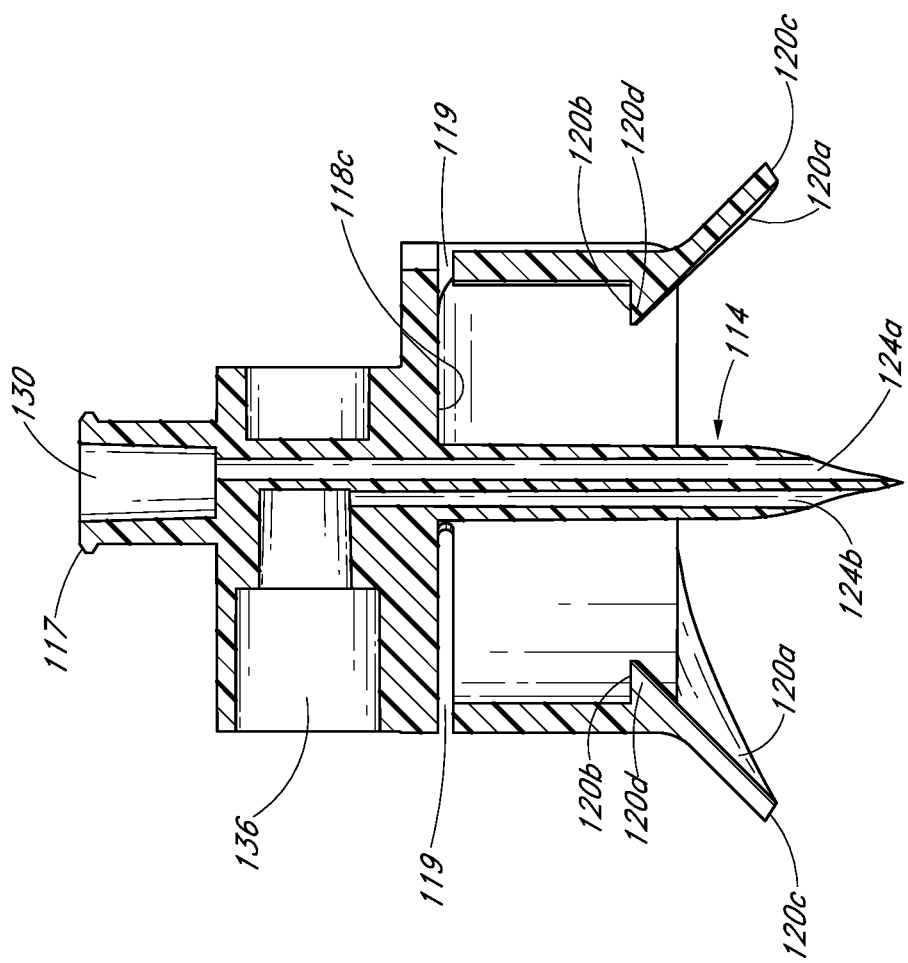

VIAL ADAPTOR

PRIORITY CLAIM AND INCORPORATION BY REFERENCE

This application claims the benefit under 35 U.S.C. §119 of U.S. Provisional Patent Application No. 61/029,542, filed Feb. 18, 2008 (entitled "VIAL ADAPTOR").

This application incorporates by reference the entire disclosure of U.S. Provisional Patent Application No. 61/029,542, filed Feb. 18, 2008 (entitled "VIAL ADAPTOR") and U.S. patent application Ser. No. 11/414,948, filed May 1, 2006 (entitled "VIAL ADAPTOR FOR REGULATING PRESSURE").

BACKGROUND OF THE DISCLOSURE

1. Field of the Disclosure

This invention relates generally to medical connectors through which fluids flow, and in particular, to medical connectors for use with medicament vials.

2. Description of the Disclosure

Vials or ampules are routinely used in hospitals and other medical settings for storing medications in the form of liquids and powders, as well as in other forms such as capsules. Vials can have a tubular shape or a bottle-like shape with a neck, but are available in a variety of other shapes as well. Vials are typically made from glass, such as borosilicate glass, but can be made from any desired material such as polypropylene or any other suitable glass or plastic. The glass can be colorless or colored, typically amber, depending on the application and medication stored. Vials are available in a range of opening sizes. For example, vials are commercially available having 8 mm, 11 mm, 13 mm, 17 mm, 20 mm, and 28 mm opening sizes, among others.

A range of different closure systems can be used with commonly used vials. Typically, vials have a stopper (or sometimes referred to herein as septa or septum) to sealingly close the opening in the vial. Metal foil, such as from aluminum, can be crimped or wrapped around the upper portion of the vial to secure the stopper to the vial in such a manner that an airtight seal can be created between the septum and the vial. The metal foil, or cap, as the term is used herein, can also prevent tampering and contamination of the vial. Some stoppers or septa, such as those made from soft rubber like butyl rubber, silicone, or other elastomeric materials, permit easy access to the medication or other contents within the vial without requiring the user to remove the cap from the vial. Septa also provide the benefit of helping to protect the contents of the vial from contamination from bacteria, germs, viruses, or other contaminants. The soft material allows a medical syringe or spike to penetrate the septa and allows the septa to sealingly close around the cannula of the medical syringe or spike to prevent leakage or contamination. Septa can be partially or fully coated with a more durable material such as polytetrafluoroethylene (PTFE) for added durability.

When a syringe or other connector is engaged with the septum, the closure of the septum can be temporarily opened, pierced, or moved to allow fluid to flow from the vial through the cannula of the syringe or other connector. Even in connectors that have a larger cannula than traditional syringes (such as in vial adaptors), the cannula can be withdrawn from the septum and the soft material of the septum will typically reseal itself after the desired amount of medication is drawn through the cannula and the connector is removed. However, because the depth or thickness of septa may vary from one vial to the next, due to the different sizes and configurations of the vials or septa, it may be difficult for a single vial adaptor to be optimally designed to work most effectively with a broad range of vial sizes and configurations. Thus, there is a need for a vial adaptor that is adaptable for a wide range of vial sizes and configurations.

Additionally, presently known vial adaptors and metal cannula syringes suffer from other drawbacks, including potentially exposing the syringe/vial adaptor user and recipient of the medicine to the harmful substances that are sometimes contained in the vials, either through inhalation or skin contact.

SUMMARY OF SOME EMBODIMENTS

Disclosed are various embodiments of vial adaptors. In many embodiments, the adaptors are configured to attach to multiple types and/or sizes of vials. It is contemplated that the features of the various embodiments disclosed herein are combinable to form additional embodiments. Such combinations are within the scope of this disclosure.

Some embodiments comprise a vial adaptor configured to be attachable to a vial so as to be in an operable position wherein contents of the vial can be removed through the vial adaptor, the vial having an opening and a seal wherein the seal defines a fluid barrier surface. In some embodiments, the vial adaptor comprises a body portion, a penetrating portion supported by the body portion, the penetrating portion projecting from a first surface of the body portion and comprising an outer surface and a distal end portion, the penetrating portion being configured to be inserted through the seal past the fluid barrier surface so as to be positioned within an interior space of the vial. In some embodiments, the vial adaptor can also include an interface portion supported by the body portion, the interface portion projecting from a second surface of the body portion and at least one deflectable tab comprising a proximal end, a distal end, and a protruding portion, the proximal end being supported by the body portion and the distal end being unrestrained so as to allow at least the distal end of the tab to be deflectable away from the penetrating portion, the tab being bendable about an axis that is generally parallel with a centerline axis through the penetrating portion. In some embodiments, the vial adaptor also comprises a first opening disposed axially through at least a portion of the interface portion and a second opening disposed axially through the penetrating portion, wherein the second opening comprises a first end portion and a second end portion and is configured such that the first end portion is in communication with the first opening and the second end portion passes through the outer surface of the penetrating portion.

In some embodiments, the operable position of the vial adaptor has a position of the vial adaptor relative to the vial where the second end portion of the second opening is positioned within the interior space of the vial.

Some embodiments comprise a vial adaptor configured to be attachable to a vial so as to be in an operable position wherein contents of the vial can be removed through the vial adaptor, the vial having an opening and a seal wherein the seal defines a fluid barrier surface. In some embodiments, the vial adaptor comprises a body portion, a penetrating portion supported by the body portion, the penetrating portion projecting from a first surface of the body portion and comprising an outer surface and a distal end portion, the penetrating portion being configured to be inserted through the seal past the fluid barrier surface so as to be positioned within an interior space of the vial, an interface portion supported by the body portion, the interface portion projecting from a first surface of the body portion, at least one deflectable tab comprising a proximal end, a distal end, and a protruding portion, the proximal end being supported by the body portion and the distal end being unrestrained so as to allow at least the distal end of the tab to be deflectable away from the penetrating portion, a first opening disposed axially through at least a portion of the interface portion, and a second opening disposed axially through the penetrating portion, wherein the second opening comprises a first end portion and a second end portion and is configured such that the first end portion is in communication with the first opening and the second end portion passes through the outer surface of the penetrating portion and the operable position of the vial adaptor is defined as the position of the vial adaptor relative to the vial when the second end portion of the second opening is positioned within the interior space of the vial, the vial adaptor being configured to provide support to the vial in at least the axial direction so as to bias the vial adaptor at least a predetermined axial position relative to the vial such that the second end portion of the second opening is located within the interior space of the vial and at least one tab being configured to bias the vial adaptor to a predetermined axial position relative to the fluid barrier surface so as to minimize the distance between the second end portion of the second opening and the fluid barrier surface for a wide range of vial sizes.

Some embodiments comprise a vial adaptor comprising a base comprising a first surface and a second surface, an interface portion extending from the first surface, and a penetrating portion extending from the second surface, the base further comprising a shroud extending from the second surface and spaced apart from and surrounding at least a portion of the penetrating portion, the shroud comprising at least one deflectable tab.

In some embodiments, the at least one deflectable tab deflects around an axis of deflection extending generally parallel to a centerline axis through the penetrating portion.

Some embodiments comprise a vial adaptor comprising a base comprising a first surface and a second surface, an interface portion extending from the first surface, and a penetrating portion extending from the second surface and forming a tip end, the base further comprising at least one pair of opposing tabs extending from the second surface and spaced apart from and on opposite sides of the penetrating portion, the opposing tabs each including an abutment surface extending toward the penetrating portion, the base defining a curve wherein a plane drawn through the intersection of the tabs and the base intersects the penetrating portion closer to the tip end of the penetrating portion than where the penetrating portion meets the second surface of the base.

BRIEF DESCRIPTION OF THE DRAWINGS

Certain embodiments of the present invention will now be described in reference to the accompanying drawings. The illustrated embodiments, however, are merely examples and are not intended to limit the invention. The following are brief descriptions of the drawings.

FIG. 19 is a top view of the embodiment of the filter member shown in FIG. 16.

FIG. 20 is a section view of the embodiment of the filter member shown in FIG. 16, taken through line 20-20 in FIG. 19.

FIG. 21 is a perspective view of another embodiment of a vial adaptor.

FIG. 22 is another perspective view of the embodiment of the vial adaptor shown in FIG. 21.

FIG. 25 is a section view of the embodiment of the vial adaptor shown in FIG. 21, taken through line 25-25 in FIG. 23.

DETAILED DESCRIPTION OF SOME EXEMPLIFYING EMBODIMENTS

The following detailed description is now directed to certain specific embodiments of the invention. In this description, reference is made to the drawings wherein like parts are designated with like numerals throughout the description and the drawings.

While needle-type medical syringes were conventionally used for many decades to access the contents of the vials, now safer, easier-to-use vial adaptors are favored in the medical industry, for many reasons. First, vial adaptors can have thicker cannulas and some degree of shielding of the cannulas to reduce the risk of the user inadvertently puncturing his or her skin. Also, some vial adaptors can be designed to be removably supported by the lip or end portion of the vial so that the vial adaptor can be axially as well as radially secured by the vial.

When a cannula is passed through the septum on a vial, the medication can be withdrawn through an open end of the cannula. Typically, the vial is turned upside down so that the stopper end is oriented downward, allowing the medication to be withdrawn from the vial with only minimal penetration of the cannula through the septum. Thus, the depth of the cannula into the vial (i.e., the length of the cannula that has penetrated past the inside, planar surface of the septum or stopper) can have a bearing on the volume of the medication that can be removed. With the vial in the upside down orientation, i.e., such that the stopper or septum side is facing downward, the medication will accumulate above the inside surface of the septum such that the end of the cannula can be positioned very close to the inside surface of the septum to extract as much medication as possible from the vial. As will be discussed, some embodiments of the vial adaptor described herein achieve this for a wide range of vial sizes.

Figure 1:
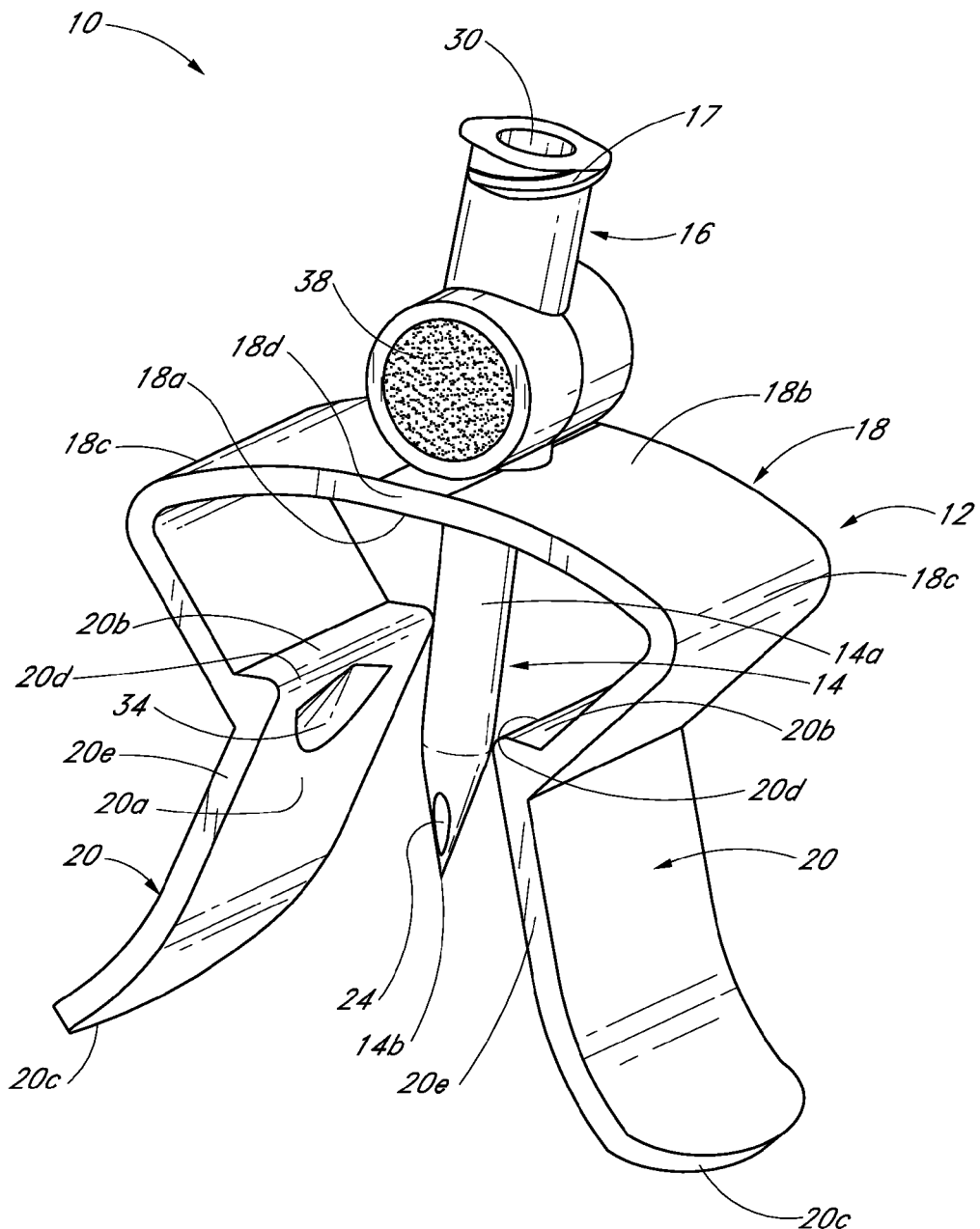
FIG. 1 is a perspective view of an embodiment of a vial adaptor.

FIG. 1 is a perspective view of an embodiment of a vial adaptor 10 comprising a body portion 12, a penetrating portion 14, and an interface portion 16. In some embodiments, the vial adaptor 10 can be formed without a penetrating portion 14, and can be used to seal an open vial that has already been opened or for which the septum or seal has been damaged or removed. In the illustrated embodiment, the body portion 12 can comprise a central portion 18 (that can be curved) and one or more tabs 20 (which can be opposing) attached to the central portion 18. Each of the tabs 20 can be supported at a proximal end of the tab 20 by the central portion 18 of the body portion 12. As can be seen in the referenced Figures, the distal end of the tabs 20 can each be unrestrained so as to allow the tab to deflect outward.

Figure 2A:
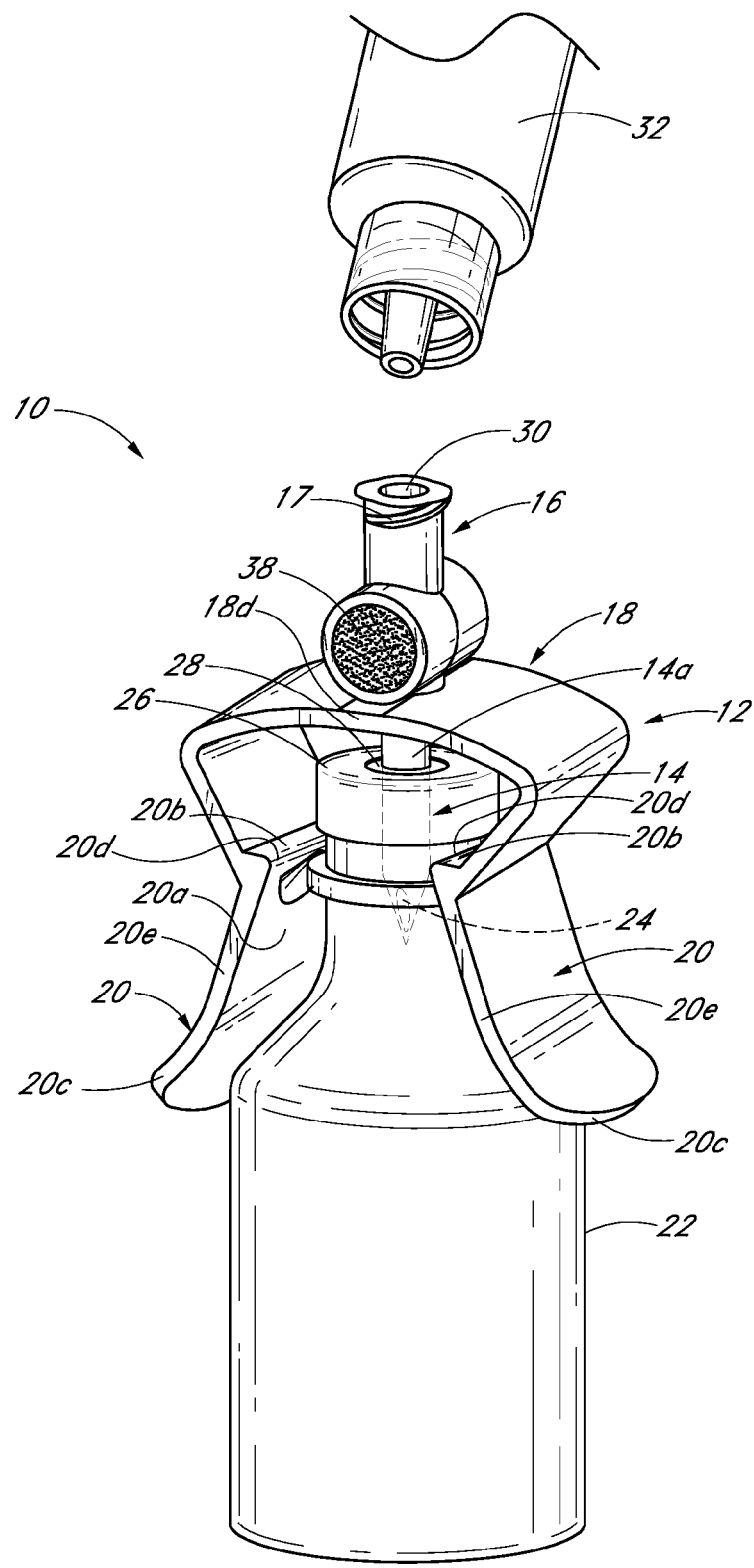
FIG. 2A is a perspective view of the embodiment of the vial adaptor of FIG. 1 attached to a vial.

FIG. 2A is a perspective view of the vial adaptor 10 of FIG. 1 attached to a vial 22. The body portion 12, including the central portion 18 and tabs 20, can help removably secure the vial adaptor 10 to the outside surface of the vial 22 and can help facilitate the removal of the vial adaptor 10 from the vial 22, as will be discussed in greater detail below. In some embodiments, not shown, the body portion 12 can define only one tab 20, as opposed to a pair of opposing tabs 20, the single tab being configured to removably secure the vial adaptor 10 to the outside surface of the vial 22 and to facilitate the removal of the vial adaptor 10 from the vial 22. The single tab 20 described above can be of any suitable configuration, including those set forth herein.

Figure 5:
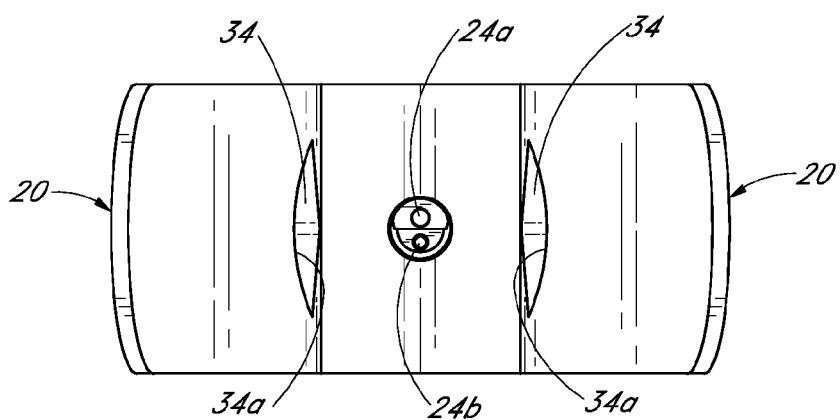
FIG. 5 is a bottom view of the embodiment of the vial adaptor of FIG. 1.
Figure 6:
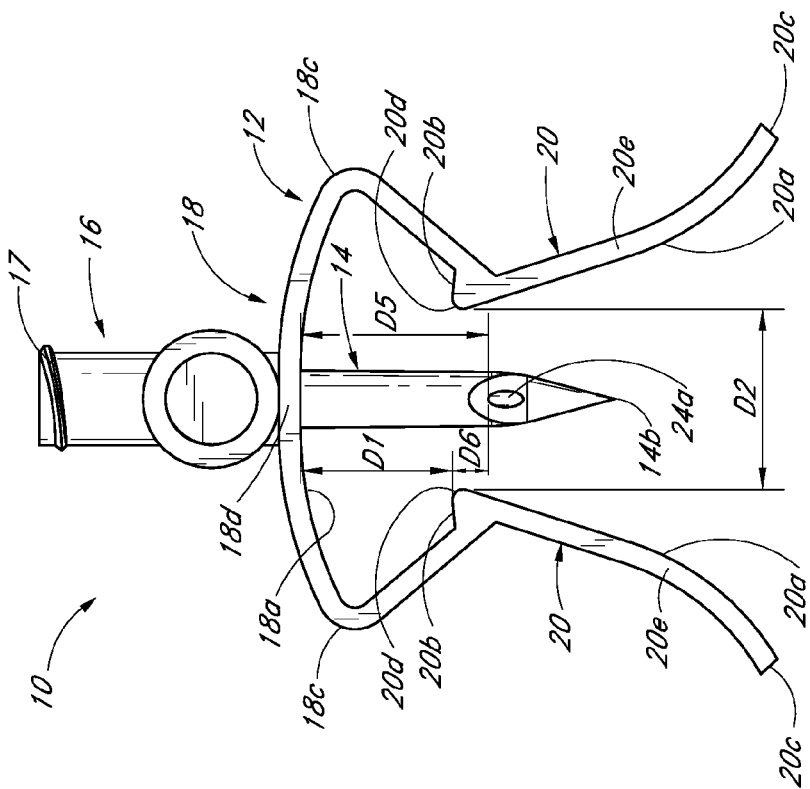
FIG. 6 is a side view of the embodiment of the vial adaptor of FIG. 1 from line 6-6 in FIG. 4.
Figure 9:
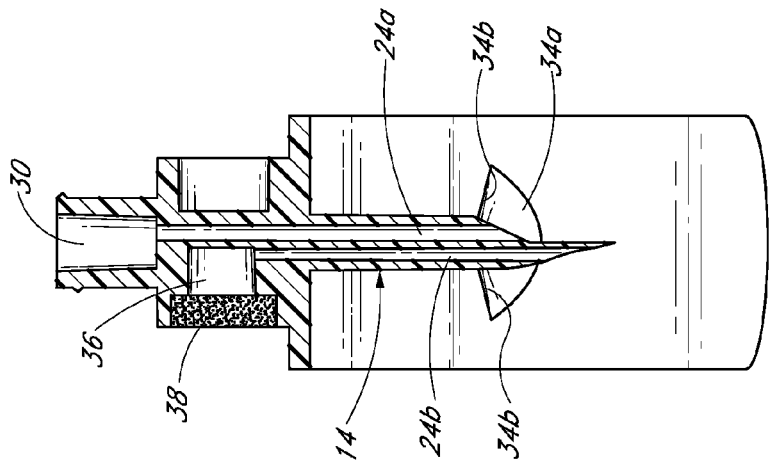
FIG. 9 is a section view of the embodiment of the vial adaptor of FIG. 1 taken along the line 9-9 in FIG. 4.

In the illustrated embodiment, the penetrating portion 14 can be supported by the body portion 12. As illustrated in FIG. 1, the penetrating portion 14 can project downward from the bottom or first surface 18a of the central portion 18 of the body portion 12. The penetrating portion 14 can comprise a cannula with a cylindrical outer surface 14a, an end portion 14b that can be configured to penetrate through a septum or stopper, and one or more axial openings 24 therethrough. The end portion 14b can be pointed (as illustrated), can be rounded or dulled, or can comprise any suitable shape. In particular, in some embodiments, as illustrated for example in FIGS. 5, 7, and 9, the penetrating portion 14 can have an opening 24a axially therethrough. The opening 24a can be configured to permit the contents of the vial 22 to be extracted therethrough. The vial adaptor 10 can have only one, or can have any number of openings 24 therethrough. In some embodiments, the penetrating portion 14 can also have another opening 24b axially therethrough, for example as illustrated in FIGS. 5, 6, and 9. Further, as illustrated in FIG. 2A, the vial 22 can comprise a foil cap 26 that can be made from aluminum or any other suitable material. As used herein, unless otherwise specified, the term vial is meant to refer to the vial, the seal, the cap, and/or any other components or features associated with the vial. For convenience of illustration, the cap 26 has been omitted from some of the figures herein. However, this omission is not meant to limit the applicability of any of the vial adaptors herein to vials and/or stoppers without foil caps. Any of the embodiments of the vial adaptors disclosed herein can be configured to work with vials having a foil cap surrounding the stopper or septum, as well as with vials not having such caps.

The penetrating portion 14 can be inserted through a septum or stopper 28, or any other object that is typically used to seal the opening in the vial 22, by pushing the penetrating portion 14 of the vial adaptor 10 against the stopper 28 until the penetrating portion 14 protrudes through the stopper 28, as shown in FIG. 2A. As used herein, the term cap refers to the upper portion of the vial that secures a penetrable portion and can include the foil (metal or otherwise) that can be wrapped around the upper portion of the vial to secure the stopper to the vial and prevent tampering and contamination. In this arrangement, as illustrated in FIG. 2A, the openings 24a, 24b can be positioned inside the vial 22 below the bottom surface of the stopper 28 so as to be in communication with the inside volume of the vial. In some embodiments, as in the illustrated embodiment, the penetrating portion 14 can define a circular cross-section. However, the penetrating portion 14 can define an ovular, triangular, square, rectangular, or any other suitably shaped cross-section. A result of having a triangular, square, or other non-smoothly shaped cross-section can be that the penetrating portion can engage with the cap 26 or stopper 28 of the vial to inhibit the vial adaptor 10 from twisting or rotating relative to the vial.

In some embodiments, the cross-section of the penetrating portion 14 can be substantially smaller than its length. For example, in some embodiments, the cross-section of the penetrating portion 16 can be less than approximately ¼th of its length. Additionally, the cross-section of the penetrating portion 16 can be less than approximately ⅛th of its length, than approximately $1/10^{th}$ of its length. The cross-section of the penetrating portion 14 can define a diameter or size that can be approximately 5 mm. In some embodiments, the penetrating portion 14 can define a cross-sectional diameter or size that can range from approximately 1 mm to approximately 4 mm, or from approximately 4 mm to approximately 7 mm, or from approximately 7 mm to approximately 10 mm.

Because, in some embodiments, the penetrating portion 14 can define a relatively large cross-sectional diameter or size, the frictional force of the seal from the stopper 28 around the outer surface 14a of the penetrating portion 14 can provide some axial support to the vial adaptor 10 so as to inhibit the axial movement of the vial adaptor 10 relative to the vial 22. In some embodiments, the outer surface 14a of the penetrating portion 14 can comprise features such as, but not limited to, ribs or striations that can be oriented perpendicular to the longitudinal axis of the penetrating portion 14, to increase the axial support provided by the stopper 28 to the penetrating portion 14. As will be discussed in greater detail below, in some embodiments, the vial adaptor 10 can be configured so as to control the depth of the end portion 14b of the penetrating portion 14 relative to the bottom surface of the cap 26 so as to increase or maximize the amount of fluid that can be withdrawn from the vial 22 when the vial is in a cap down orientation, even when used with a range of different vial sizes.

In some embodiments, the penetrating portion 14 can define a length (i.e., the distance from the first surface 18a to the end portion 14b of the penetrating portion 14) that can be approximately 20 mm. In some embodiments, the length of the penetrating portion 14 can be from approximately 12 mm to approximately 17 mm, or from approximately 17 mm to approximately 22 mm, or from approximately 22 mm to approximately 27 mm or from or to any value in these ranges.

For example, in some embodiments, the penetrating portion 14 can define a length that can be approximately 60% of the diameter of the largest sized vial that the vial adaptor 10 is intended to be inserted into. In some embodiments, the penetrating portion 14 can define a length that can be from approximately 40% to approximately 65%, or from approximately 65% to approximately 90%, or from approximately 90% to approximately 125% of the approximate diameter of the largest sized vial that the vial adaptor 10 is intended to be inserted into. However, the penetrating portion 14 is not limited to the specific ranges of lengths, diameters, or other configurations described above. The penetrating portion 14 can be of any size or configuration that is suitable for the vial or vials for which the vial adaptor 10 is intended to be used.

In the illustrated embodiment, the interface portion 16 can be supported by the body portion 12. As illustrated in FIG. 1, the interface portion 16 can project upward from the upper or second surface 18b of the central portion 18 of the body portion 12. In some embodiments, the interface portion 16 can comprise a cylindrical outer surface and a third opening 30 axially disposed through at least a portion of the interface portion 16. In the illustrated embodiment, as most clearly shown in FIGS. 4 and 9, the opening 30 can be in fluid communication with the opening 24a such that the contents of the vial 22 can pass from the opening 24a through the third opening 30. In some embodiments, the opening 30 can be sealed or sealable.

Any of a variety of suitable means for sealably closing the interface portion 16 of the vial adaptor 10 can be used to prevent the contents of the vial 22 from flowing out of the vial 22 when the vial adaptor 10 is inserted therein, as well as to seal the vial adaptor 10 and vial 22 from contamination from bacteria, germs, or other contaminants. In some embodiments, the closing means or mechanisms can function to prevent and/or impede the contents of the vial 22 from escaping from or entering into the vial, while allowing the contents of the vial 22 to flow through the vial adaptor 10 when the closing means is opened or engaged with a corresponding male tipped connector or syringe or otherwise. As used herein, terms such as "closed" or "sealed" should be understood as obstructions or barriers to fluid flow. These terms should not be understood to require that a particular structure or configuration achieves a complete fluid closure in all circumstances.

Figure 2B:
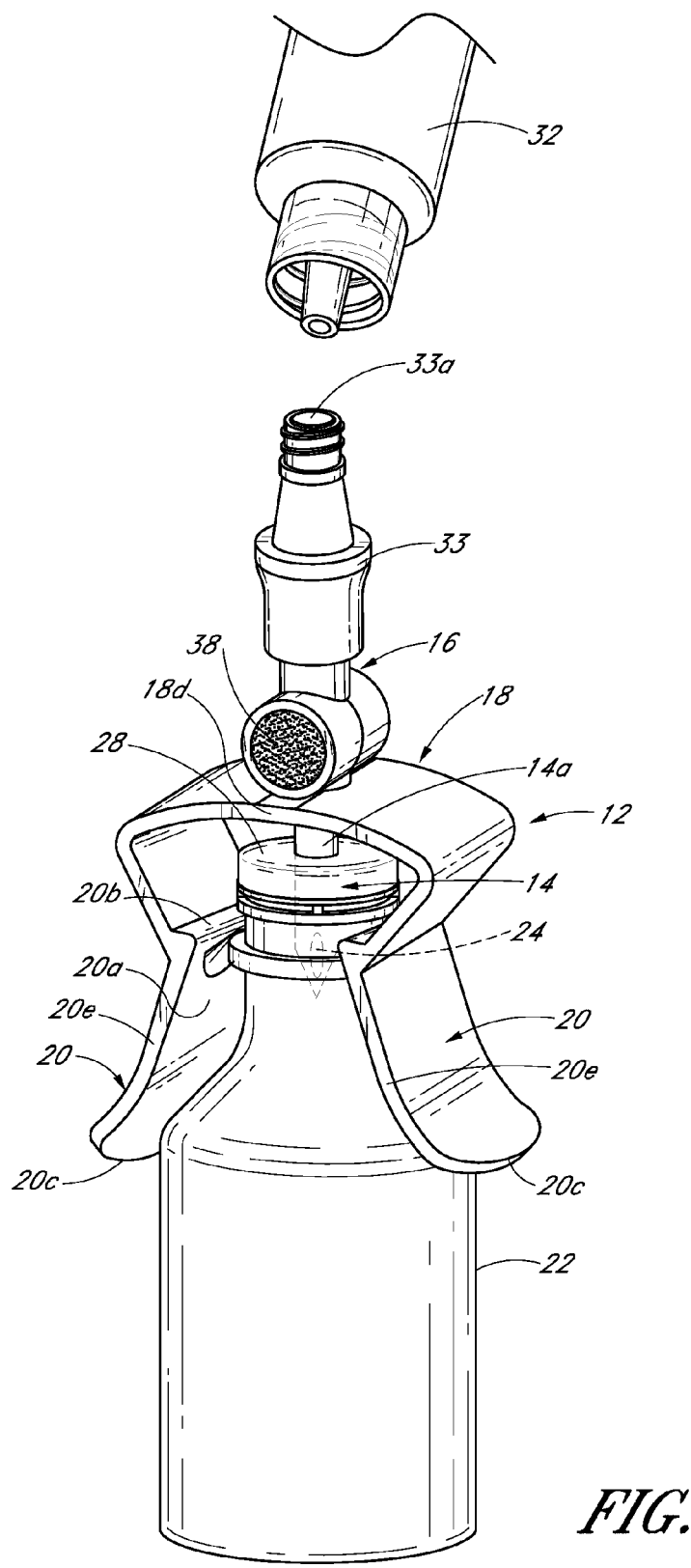
FIG. 2B is a perspective view of another embodiment of a vial adaptor attached to a vial.

The interface portion 16 can be configured to be connectable with any suitable medical connector or fluid flow connector, such as, without limitation, a male Luer connector. In some embodiments, the interface portion 16 can comprise a flange, protrusions (which can be opposing), or threads 17 to aid in coupling the vial adaptor 10 with the medical connector, a medical device, or other instrument. In some embodiments, the interface portion 16 can define a generally smooth cylindrical surface without such flange, protrusions, or threads. In some embodiments, the medical connector, a medical device, or other instrument can be secured to the interface portion 16 with adhesive or any other bonding or adhesive material. The interface portion 16 can be configured to accept any suitable medical connector, such as a syringe 32 or sealable medical connector 33, or other connectors capable of sealing upon removal of a medical device therefrom. As illustrated in FIG. 2b, in some arrangements, the flange 17 can be sized and configured to accept the Clave® connector, available from ICU Medical, Inc. of San Clemente, Calif. Certain features of the Clave® connector are disclosed in U.S. Pat. No. 5,685,866. Connectors of many other varieties, including other needleless connectors, can also be used.

With the vial adaptor 10 attached to the vial 22, the plunger of a syringe 32 can be withdrawn to extract the contents of the vial 22 through the vial adaptor 10. With reference to FIG. 2B, the medical connector 33 can be any suitable device, currently available or later developed. The medical connector 33 can have a sealable end portion 33a. The connector 33 can be sealable so that a user or practitioner can clean or swab the surface thereof without contaminating the contents of the vial. A sealable female end can also prevent the contents of the vial from leaking when the vial adaptor 10 is attached thereto. This can be particularly important in the field of oncology, where many of the fluids that are contained in the vials can be very harmful if touched or inhaled. Further, the sealable female end can prevent foreign substances, various airborne viruses, bacteria, dust, spores, molds, and other unsanitary and harmful debris or contaminants from entering of the vial.

In some embodiments, the sealable end portion 33a can comprise a soft or rigid poppet that can be depressed by a syringe or other suitable male medical implement. In some embodiments, the sealable end portion 33a can comprise a deformable rubber barrier having a slit, or other self-sealing mechanism incorporated therein. In some embodiments, the medical connector 33 or a portion of the medical connector 33 can be integrally formed with the vial adaptor 10. In some embodiments, the syringe 32 or a portion of the syringe 32 can be integrally formed with the vial adaptor 10. In some embodiments, the syringe 32 or female connector 33 can be separately formed and can be removably or fixedly attached to the vial adaptor 10.

Figure 3A:
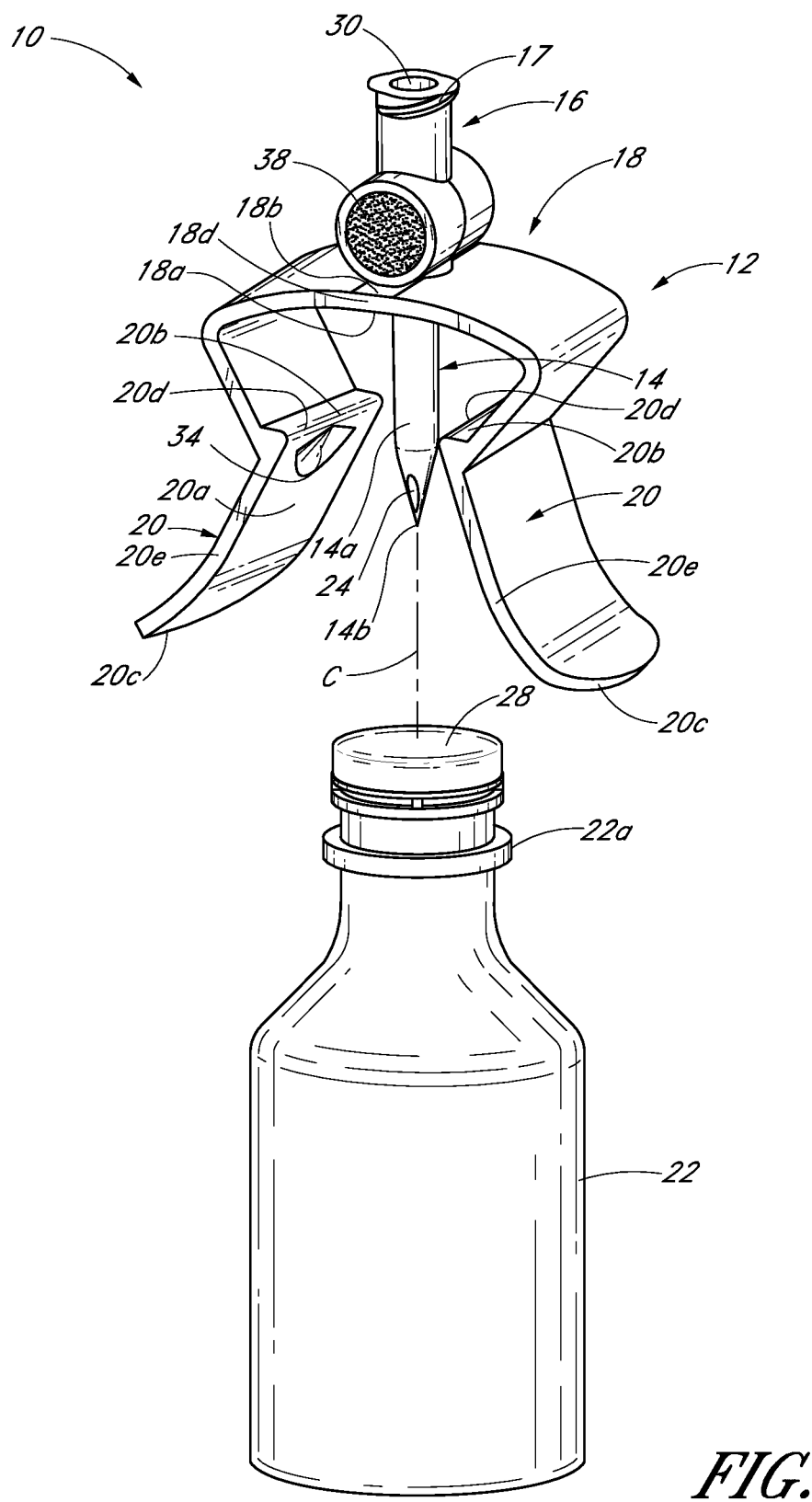
FIGS. 3A-3C are perspective views of the embodiment of the vial adaptor of FIG. 1, depicting the vial adaptor being inserted into a vial.
Figure 3B:
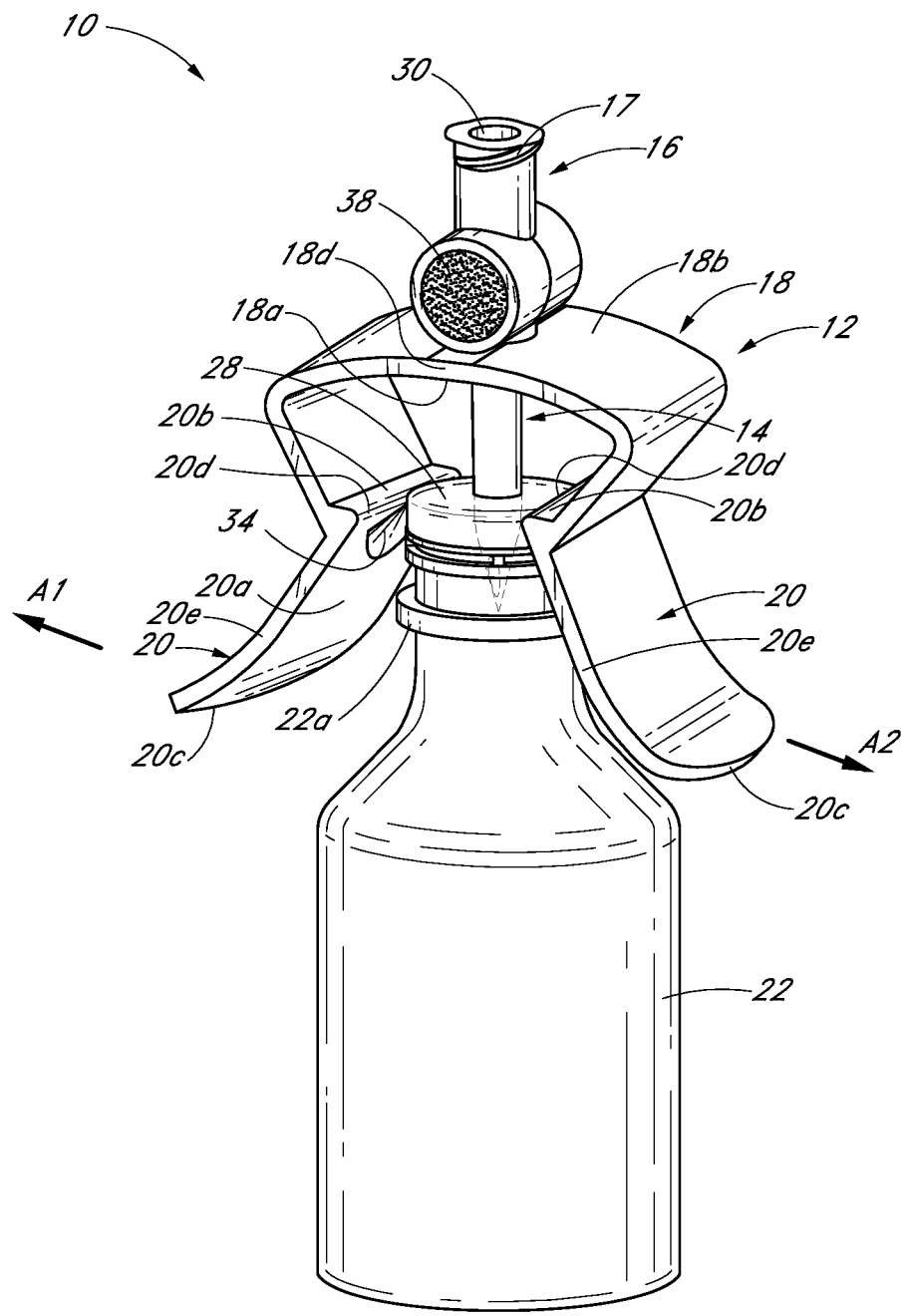
Figure 3C:
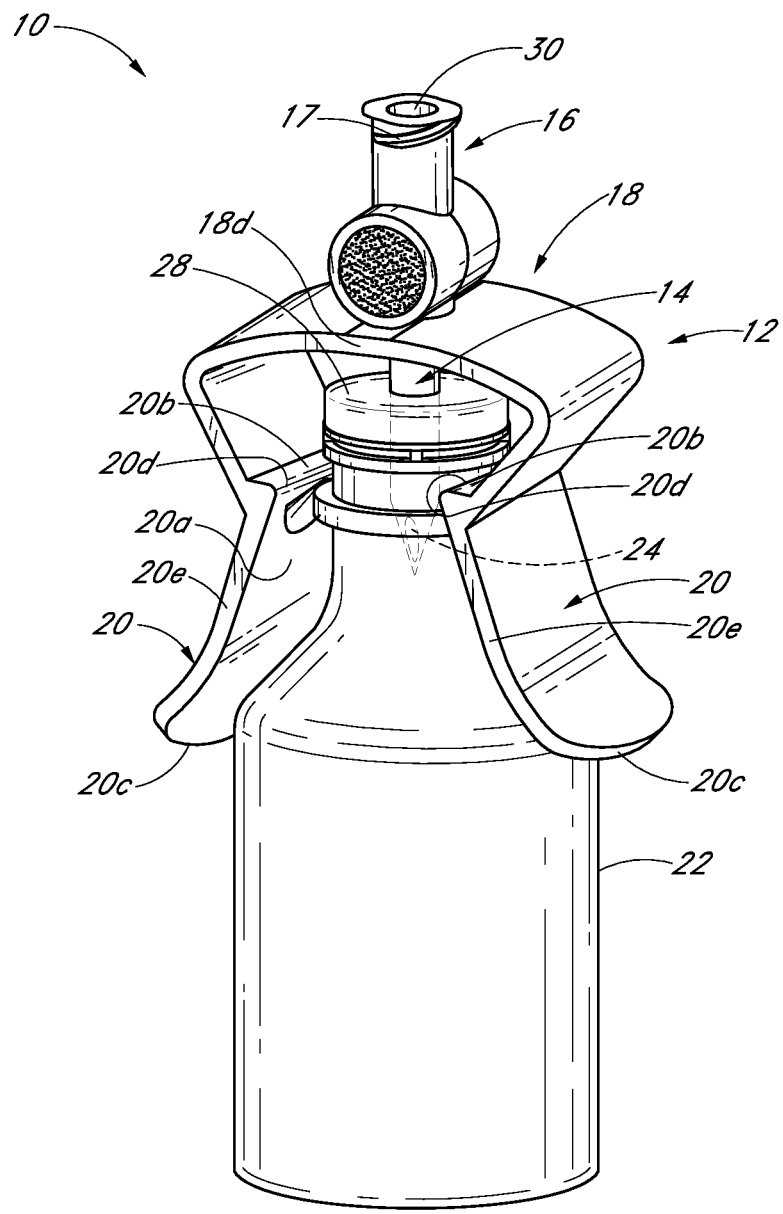

With reference to FIGS. 3A-3C, one method by which the vial adaptor 10 can be inserted on or attached to a vial will now be briefly described. With reference to FIG. 3A, the vial adaptor 10 can be positioned above the top of the stopper 28 of the vial 22 so that the axial center of the penetrating portion 14 is approximately aligned with the axial center of the rubber septum or stopper 28 (as indicated by the centerline C). By grasping the vial adaptor 10 and pushing the vial adaptor 10 downwardly against the stopper 28, the penetrating portion 14 can be introduced into the stopper 28, as illustrated in FIG. 3B. As force is continued to be applied to the vial adaptor 10, the stopper 28 of the vial 22 can eventually contact the inside surface 20a of the tabs 20. Further axial force can cause the deflectable tabs 20 to spread apart (e.g., in opposing directions as shown by arrows A1 and A2) so that the penetrating portion 14 of the vial adaptor 10 can be further inserted into the vial. For example, in some embodiments, the tabs 20 can be configured so that a user can easily spread the tabs 20 apart by grasping or otherwise exerting a force on the inside surface of the end portions 20c of the tabs 20 and deflecting the tabs 20 away from the vial.

The vial adaptor 10 can be inserted into the vial such that the end portion 14b of the penetrating portion 14 protrudes through the stopper 28 to a sufficient distance so that the one opening 24 in the penetrating portion 14 can be in communication with the inside volume of the vial 22. In this configuration, the contents of the vial 22 can be extracted through the opening or openings 24. As mentioned, the vial adaptor 10 can be configured to control the depth of penetration of the penetrating portion 14 into the vial for a multitude of the vial sizes so as to increase or maximize the amount of medicament or other substance that can be extracted from the vial through the vial adaptor 10.

Figure 4:
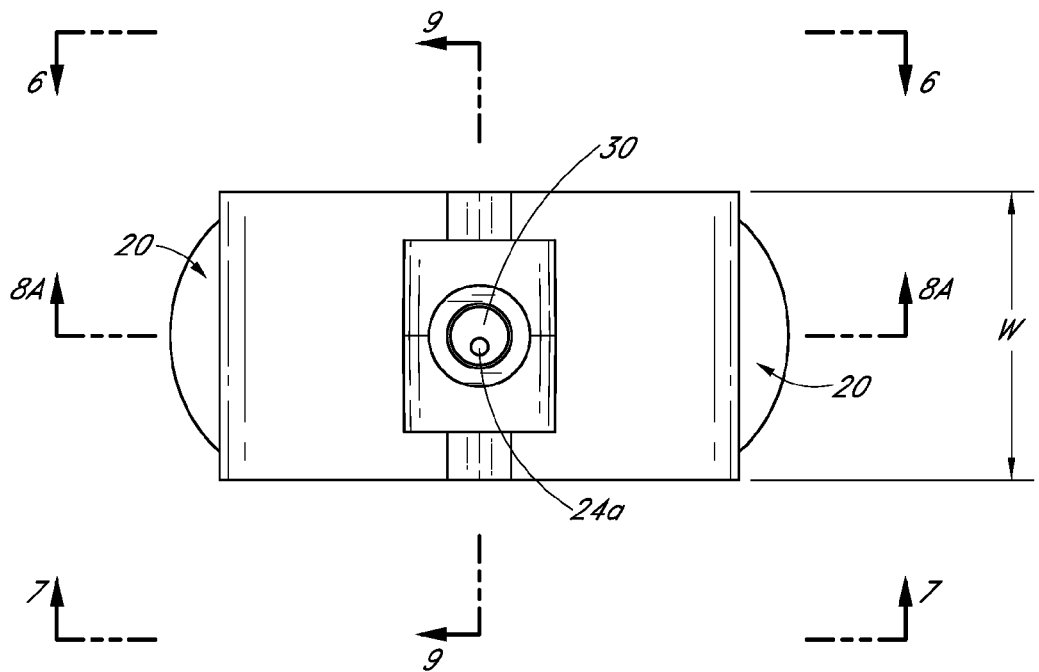
FIG. 4 is a top view of the embodiment of the vial adaptor of FIG. 1.
Figure 7:
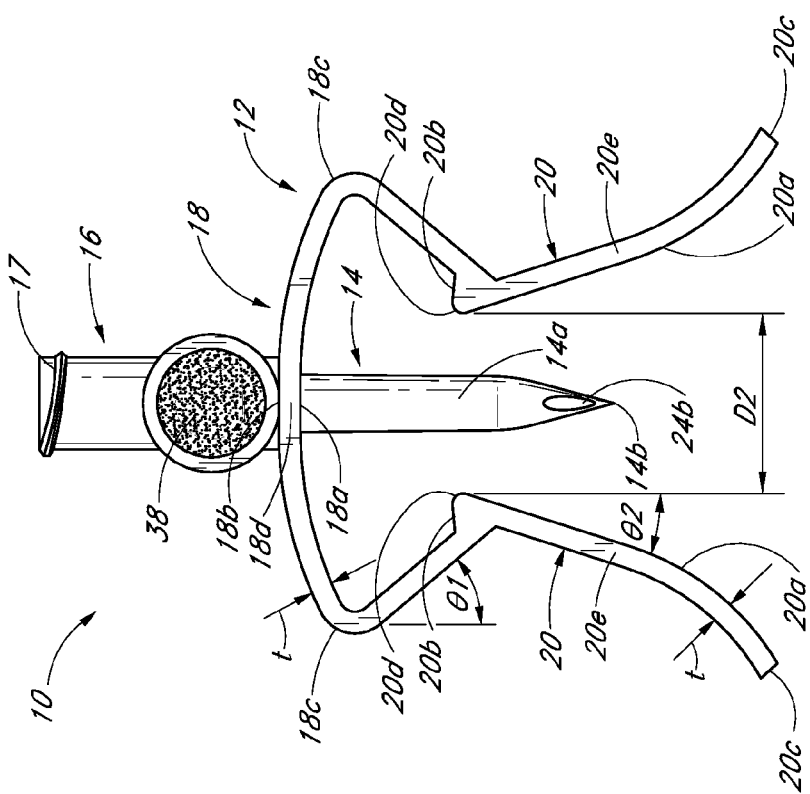
FIG. 7 is a side view of the embodiment of the vial adaptor of FIG. 1 from line 7-7 in FIG. 4.

With reference to FIGS. 1-9, the features of the various embodiments of the vial adaptors disclosed herein will now be described in greater detail. FIGS. 4 and 5 depict top and bottom views of the vial adaptor 10, respectively, while FIGS. 6 and 7 depict side views of the vial adaptor 10, respectively, as defined in FIG. 4. FIGS. 8A and 9 depict section views of the vial adaptor 10 as defined in FIG. 4.

As mentioned above, the body portion 12 can comprise a pair of opposing tabs 20 attached to the central portion 18. In some embodiments, the tabs 20 each can define an inside surface 20a, an abutment surface 20b, an end portion 20c, and a protruding portion 20d. As will be discussed below, the abutment surfaces 20b and protruding portions 20d can aid in removably securing the vial adaptor 10 to the vial 22. With reference to the side view of the FIG. 6, each tab 20 can be supported by and attached to the end portion 18c of the central portion 18. In some embodiments, the end portion 18c can be curved, as illustrated most clearly in FIG. 6.

In the illustrated embodiment, the first portion of each tab 20 (i.e., the portion of each tab 20 approximately above the abutment surfaces 20b and below the end portion 18c of the central portion 18) can angle inwardly toward the penetrating portion 14. In some embodiments, the first portion of each tab 20 can taper inwardly at an angle θ1 (defined in FIG. 6) that can be approximately 45° relative to a vertical plane, or from approximately 25° to approximately 40°, or from approximately 40° to approximately 55° relative to a vertical plane.

In some embodiments, the length of the first portion of each tab 20 can be less than the length of the penetrating portion 14. For example, in some embodiments, the length of the first portion of each tab 20 can be less than ¾ of the length of the penetrating portion 14, than ½ the length of the penetrating portion 14. The length of the first portion of each tab 20 can be from approximately 50% to approximately 60%, or from approximately 60% to approximately 70%, or from approximately 70% to approximately 80% of the length of the penetrating portion 14, or from or to any value within these ranges. In some embodiments, the length of the first portion of each tab 20 can be approximately 13 mm. In some embodiments, the length of the first portion of each tab 20 can be from approximately 10 mm to approximately 12.5 mm, or from approximately 12.5 mm to approximately 15 mm, or from approximately 15 mm to approximately 17.5 mm or from or to any value in these ranges.

The end portion 20c can be approximately defined as the portion of the tabs 20 below the abutment surfaces 20b. In some embodiments, the length of the end portion 20c of each tab 20 can be greater than the length of the penetrating portion 14. For example, in some embodiments, the length of the end portion 20c of each tab 20 can be at least approximately ¼ larger or at least approximately ½ larger than the penetrating portion. In some embodiments, the length of the end portion 20c of each tab 20 can be from approximately 110% to approximately 120%, or from approximately 120% to approximately 140%, or from approximately 140% to approximately 160% of the length of the penetrating portion 14. In some embodiments, the length of the end portion 20c of each tab 20 can be approximately 23 mm. In some embodiments, the length of the end portion 20c can be from approximately 18 mm to approximately 22 mm, or from approximately 22 mm to approximately 26 mm, or from approximately 26 mm to approximately 30 mm or from or to any value in these ranges.

In the illustrated embodiment, the end portion 20c of each tab 20 can taper outwardly away from the penetrating portion 14. In some embodiments, the end portion 20c of each tab 20 can taper outwardly at an angle θ2 (defined in FIG. 6) that can be approximately 25° relative to a vertical plane, or from approximately 15° to approximately 30°, or from approximately 30° to approximately 45° relative to a vertical plane.

In some embodiments, as in the illustrated embodiments, the tabs 20 can define generally planar side surfaces 20e that, for each tab 20, can be opposing and generally parallel to one another. In some embodiments, the width of each tab 20 (represented by "W" in FIG. 4, which can be the distance between the opposing side surfaces 20e for each tab 20) can be substantially greater than the diameter or size of the cross-section of the penetrating portion 14. For example, in some embodiments, the width of each tab 20 can be at least approximately twice as large or at least approximately three times as large as the diameter or size of the cross-section of the penetrating portion. In some embodiments, the width of each tab 20 can be from approximately 200% to approximately 325%, or from approximately 325% to approximately 450%, or from approximately 450% to approximately 600% of the diameter or size of the cross-section of the penetrating portion 14. In some embodiments, the width of each tab 20 can be approximately 19 mm. In some embodiments, the width of each tab 20 can be from approximately 10 mm to approximately 15 mm, or from approximately 15 mm to approximately 20 mm, or from approximately 20 mm to approximately 25 mm or from or to any value in these ranges.

Additionally, in some embodiments, the width of each tab 20 can be based on the diameter of the largest sized vial of the vial adaptor 10 is intended to be inserted into. For example, in some embodiments, the width W of each tab 20 can be from approximately 50% to approximately 75%, or from approximately 75% to approximately 100%, or from approximately 100% to approximately 125% of the diameter of the opening of the largest sized vial that the vial adaptor 10 is intended to be inserted into.

In some embodiments, the thickness of the material forming each tab 20 (represented by "t" in FIG. 6) can be significantly less than the diameter or size of the cross-section of the penetrating portion 14. For example, in some embodiments, the thickness "t" of the material forming each tab 20 can be less than approximately half than approximately one-quarter of the diameter or size of the cross-section of the penetrating portion 14. In some embodiments, the thickness "t" of the material forming each tab 20 can be approximately 40% of the diameter or size of the cross-section of the penetrating portion 14, or from approximately 25% to approximately 40%, or from approximately 40% to approximately 55%, or from approximately 55% to approximately 70% of the diameter or size of the cross-section of the penetrating portion 14, or from or to any value in these ranges.

In some embodiments, the thickness of the material forming each tab 20 can be approximately 1.5 mm. In some embodiments, the thickness "t" of the material forming each tab 20 can be from approximately 1 mm to approximately 1.5 mm, or from approximately 1.5 mm to approximately 2 mm, or from approximately 2 mm to approximately 2.5 mm or from or to any value in these ranges.

However, the size and configuration of each tab 20 is not limited to any of the specific sizes, ranges, or configurations described above. Each tab 20 can have any length, taper angle, thickness, width, size or configuration that is suitable for the vial or vials for which the vial adaptor 10 is intended to be used, or for the material that is chosen for each tab 20 or for any other components or features of the vial adaptor 10. In some embodiments, each tab 20 can define a different size, shape, or other configuration as compared to any other tab 20 formed on the vial adaptor.

Similarly, in some embodiments, as in the illustrated embodiments, the central portion 18 can define two generally planar side surfaces 18d that can be opposing and generally parallel to one another. In some embodiments, the width of the central portion 18 (represented by "W" in FIG. 4, which can be the distance between the opposing side surfaces 18d of the central portion 18) can be approximately 19 mm. In some embodiments, the width the central portion 18 can be significantly greater than the diameter or size of the cross-section of the penetrating portion 14. For example, in some embodiments, the width of the central portion 18 can be at least approximately twice or three times as large as the diameter or size of the cross-section of the penetrating portion. The width of the central portion 18 can be approximately at least approximately 400% of the diameter or size of the cross-section of the penetrating portion 14. In some embodiments, the width of the central portion 18 can be from approximately 200% to approximately 325%, or from approximately 325% to approximately 450%, or from approximately 450% to approximately 600% of the diameter or size of the cross-section of the penetrating portion 14. In some embodiments, the width of the central portion 18 can be approximately 19 mm. In some embodiments, the width of the central portion 18 can be from approximately 10 mm to approximately 15 mm, or from approximately 15 mm to approximately 20 mm, or from approximately 20 mm to approximately 25 mm or from or to any value in these ranges.

In some embodiments, the thickness of the material forming the central portion 18 (represented by "t" in FIG. 6) can be significantly less than the diameter or size of the cross-section of the penetrating portion 14. For example, in some embodiments, the thickness "t" of the material forming the central portion 18 can be less than approximately half than approximately three-quarters of the diameter or size of the cross-section of the penetrating portion 14. In some embodiments, the thickness "t" of the material forming the central portion 18 can be approximately 40% of the diameter or size of the cross-section of the penetrating portion 14, or from approximately 25% to approximately 40%, or from approximately 40% to approximately 55%, or from approximately 55% to approximately 70% of the diameter or size of the cross-section of the penetrating portion 14, or from or to any value in these ranges.

In some embodiments, the thickness of the material forming the central portion 18 can be approximately 1.5 mm. In some embodiments, the thickness "t" of the material forming the central portion 18 can be from approximately 1 mm to approximately 1.5 mm, or from approximately 1.5 mm to approximately 2 mm, or from approximately 2 mm to approximately 2.5 mm or from or to any value in these ranges.

As mentioned, in some embodiments, the central portion 18 can define a curved surface (as most clearly seen in FIGS. 6 and 7). In some embodiments, where the penetrating portion 14 defines a circular cross-section, the radius of curvature of the central portion 18 (that can be, but is not required to be, curved) can be significantly greater than the radius of the cross-section of the penetrating portion 14. In some embodiments, the radius of curvature of the central portion 18 can be approximately 3 cm. In some embodiments, the radius of curvature of the central portion 18 can be from approximately 2 cm to approximately 4 cm, or from approximately 4 cm to approximately 6 cm, or from approximately 6 cm to approximately 8 cm or to or from any value within these ranges.

However, the size and configuration of the central portion 18 is not limited to the specific ranges or configurations described above. The central portion 18 can be of any size or configuration that is suitable for the vial or vials for which the vial adaptor 10 is intended to be used, or for the material that is chosen for the central portion 18 or for any other components or features of the vial adaptor 10. In some embodiments, the width and thickness, or other aspects of the size and configuration of the central portion 18, can be the same as, or different than, that of the tabs 20 formed on the vial adaptor.

As mentioned, in some embodiments, the tabs 20 can each be sized and configured such that a portion of the inside surface 20a can slidingly receive the outer, generally cylindrical surface of the stopper 28 when the vial adaptor 10 is inserted into a vial. As most clearly illustrated in FIG. 3C, the abutment surfaces 20b can each be configured to inhibit the vial adaptor 10 from moving axially away from the vial 22 when the vial adaptor 10 is inserted into the vial 22 to a sufficient distance such that the abutment surfaces 20b overlap an adjacent protruding surface or surfaces on the vial 22 or stopper 28.

With reference to FIG. 7, which is a side view of the vial adaptor 10 in a pre-stressed or pre-installed state (i.e., before the vial adaptor 10 is inserted into the vial 22), the distance D1 represents the distance between the upper inside surface 18a of the body portion 18 and the abutment surfaces 20b. In some embodiments, in the pre-stressed state, the vial adaptor 10 can be sized and configured such that the distance D1 can be significantly less than the length of the penetrating portion 14. For example, in some embodiments, in the pre-stressed state, the distance D1 can be less than approximately three-quarters, than approximately half of the length of the penetrating portion 14. In some embodiments, the distance D1 can be from approximately 40% to approximately 50%, or from approximately 50% to approximately 60%, or from approximately 60% to approximately 70% of the length of the penetrating portion 14. In some embodiments, in the pre-stressed state, the vial adaptor 10 can be sized and configured such that the distance D1 is from approximately 7 mm to approximately 10 mm, or from approximately 10 mm to approximately 13 mm, or from approximately 13 mm to approximately 16 mm or to or from any value in these ranges. However, the vial adaptor 10 and any components or features thereof is not limited to the specific ranges or configurations described above. The vial adaptor 10 can be of any size or configuration that is suitable for the vial or vials for which the vial or vial adaptor 10 is intended to be used.

As mention above, the vial adaptor 10 can be configured such that the vial adaptor 10 can be attached to a wide range of vials having a wide range of cap or stopper diameters. In particular, the central portion 18 and tabs 20 can be configured so as to be elastically bendable or deformable by a user to attach to or fit around a wide range of vial cap diameters. With reference to FIG. 6, which is a side view of the vial adaptor 10 in a pre-installed state (i.e., before the vial adaptor 10 is inserted into the vial 22), the protruding portions 20$d$ on the tabs 20 of the vial adaptor 10 can define a distance therebetween (represented by distance D2). Therefore, for the illustrated embodiments, the distance D2 represents the length across the constricted portion of the vial adaptor 10 in the relaxed or pre-stressed state. In some embodiments, in the pre-stressed state, the vial adaptor 10 can be sized and configured such that the distance D2 can be significantly less than the length of the penetrating portion 14. For example, in some embodiments, in the pre-installed state, the vial adaptor 10 can be sized and configured such that the distance D2 is less than approximately three-quarters than approximately half as large as the length of the penetrating portion 14.

In some embodiments, in the pre-stressed state, the vial adaptor 10 can be sized and configured such that the distance D2 is approximately 14 mm. In some embodiments, in the pre-installed state, the vial adaptor 10 can be sized and configured such that the distance D2 is from approximately 10 mm to approximately 13 mm, or from approximately 13 mm to approximately 16 mm, or from approximately 16 mm to approximately 19 mm or from or to any value in these ranges. However, the vial adaptor 10 and any components or features thereof is not limited to the specific ranges or configurations described above. The vial adaptor 10 can be of any size or configuration that is suitable for the vial or vials for which the vial adaptor 10 is intended to be attached.

As mentioned, the vial adaptor 10 can be configured such that, when the vial adaptor 10 is attached to a vial, the tabs can be deflected and spread apart (either by the user grasping and deflecting the end portions 20$c$ of the tabs 20 or from the contact between the vial and the inside surface 20$a$ of the tabs 20) so as to accommodate a vial having a cap or stopper diameter that is larger than the distance D2 between the opposing protruding portions 20$d$ in the relaxed state. In some embodiments, the vial adaptor 10 can be sized and configured such that, when the tabs 20 are spread apart, the distance D2 between the protruding portions 20$d$ is significantly greater than the distance D2 between the protruding portions 20$d$ when the vial adaptor 10 is in the relaxed state. For example, in some embodiments, the vial adaptor 10 can be sized and configured such that the distance between the protruding portions 20$d$ when the tabs 20 are fully spread apart (i.e., when the vial adaptor 10 is mounted to a vial) can be at least approximately 50% larger than the distance between the protruding portions 20$d$ when the tabs 20 are in the relaxed state. In some embodiments, the vial adaptor 10 can be sized and configured such that the distance between the protruding portions 20$d$ when the tabs 20 are spread apart or when the vial adaptor 110 is mounted to a vial is from approximately 120% to approximately 135%, or from approximately 135% to approximately 150%, or from approximately 150% to approximately 165% or to or from any value within these ranges, of the distance between the protruding portions 20$d$ when the tabs 20 are in the relaxed state.

In particular, in some embodiments, the vial adaptor 10 can be sized and configured such that, when the tabs 20 are spread apart, the distance D2 between the protruding portions 20$d$ can be from approximately 16 mm to approximately 20 mm, or from approximately 20 mm to approximately 24 mm, or from approximately 24 mm to approximately 28 mm, or from approximately 28 mm to approximately 32 mm or from or to any value in these ranges. However, the vial adaptor 10 and any components or features thereof is not limited to the specific ranges or configurations described above. The vial adaptor 10 can be of any size or configuration that is suitable for the vial or vials for which the vial adaptor 10 is intended to be attached.

To facilitate removal of the vial adaptor 10 from the vial 22, the end portion 20$c$ of each tab 20 can be configured to have an outward flare or other structure to permit the user to easily grasp and deflect each of the tabs 20 radially outward so as to deflect away from the vial and, consequently, deflect each of the protruding portions 20$d$ radially outward away from the vial so that the abutment surfaces 20$b$ no longer overlap the protruding surface or surfaces on the vial 22, stopper 28, or cap. The end portions 20$c$ can be configured so that a user gripping or contacting the end portions 20$c$ of the tabs 20 with one hand and holding the vial 22 with the other can exert an axial, upward force on the vial adaptor 10 relative to the vial 22 so as to remove the vial adaptor 10 from the vial 22.

Additionally, in some embodiments, the end portion 20$c$ of each tab 20 can comprise channels, scores, protrusions, pits, a gnurled texture, soft rubber, or any other features, materials, or textures to prevent a user's fingers or hands from slipping relative to the surface of the end portion 20$c$ of each tab 20. Additionally, in some embodiments, as shown most clearly in a side view of FIG. 6, the distal end portions of the end portions 20$c$ can be configured to define an outwardly curved or flared surface to better enable a user to access or grasp the inside surface 20$a$ of the tabs 20. In other words, the curved or flared surface of the end portions 20$c$ of the tabs 20 better enable the user to slide his or her finger or fingers underneath the tabs 20 so that the user can exert a radially outward pressure on the tabs 20 to spread the tabs radially outward. Additionally, in some embodiments, as in the illustrated embodiments, the end of each end portion 20$c$ can be rounded or curved. This can be done to eliminate or soften otherwise sharp corners.

Because the vial adaptor 10 is configured to be attached to a wide range of vial sizes, in some embodiments, the central portion 18 and tabs 20 can be configured so as to elastically deform or deflect so that the protruding portions 20$d$ deflect outwardly over a wide range of distances to enable the vial adaptor 10 to accommodate a wide range of vial sizes. For this purpose, the central portion 18 and tabs 20 can be shaped and configured and made from a material that permits a significant amount of the elastic deflection while still allowing the tabs 20 and protruding portions 20$d$ to exert a radially inward force sufficient to adequately secure the vial adaptor 10 to the vial.

Accordingly, in some embodiments, in a relaxed state (i.e. before the vial adaptor 10 is inserted into a vial), the central portion 18 can define a curved profile, as shown most clearly in the side view of FIG. 6. With reference to FIG. 13B, when the vial adaptor is inserted into a larger vial, such as but not limited to the 28 mm vial illustrated in FIG. 13B, and the tabs 20 can be deflected radially outwardly away from the protruding portion 14, the central portion 18 can be elastically deformed so as to move toward an approximately flat profile. In some embodiments, the relaxed state curvature of the central portion 18 described above can increase the flexibility of the central portion 18, can permit the protruding portions 20d to deflect or bend outwardly over a greater distance or range of distances, and also can increase the radial inward force that the tabs 20 exert on the vial when the tabs 20 are deflected outwardly so as to allow the vial adaptor 10 to be adequately secured to a vial, without increasing the thickness of the material used to form the central portion 18.

In particular, as the tabs 20 are deflected outwardly from the relaxed state, the central portion 18 can be caused to bend so that the end portions 18c of the central portion 18 can rotate and deflect upwardly. For example, with reference to FIG. 13B, when the vial adaptor 10 has been inserted into a 28 mm vial, the tabs 20 are configured to deflect outwardly from the relaxed state, causing the central portion 18 to deflect to a more planar shape (i.e. such that the end portions 18c have been caused to deflect and rotate upwardly). As the end portions 18c of the central portion 18 are caused to deflect and rotate upwardly as described above, one result is that the taper angle θ1 can be reduced relative to a vertical plane, which increases the distance between the opposing protruding portions 20d. In this configuration, the curvature of the central portion 18 can provide for a greater expansion of the protruding portions 20d of the tabs 20.

In some embodiments, the tabs 20 can be integrally formed with the central portion 18. In some embodiments, the tabs 20 can be formed separately and fused, welded, or otherwise attached to the central portion 18 with adhesive or other suitable fastening substances or materials, such as, without limitation, screws, rivets, or pins. In some embodiments, the central portion 18 and the tabs 20 can be configured to be bendable so as to deflect when the vial adaptor 10 is inserted over the cap portion of a vial. In particular, in some embodiments, the body portion 12 can define a constricted portion such as, but not limited to, the distance between protruding portions 20d that is narrower than the diameter of the cap or neck on the vial into which the vial adaptor 10 is to be inserted, so that the tabs 20 deflect outward (as indicated by the arrows A1 and A2 in FIG. 3B) as the penetrating portion 14 is being inserted into and through the stopper 28. Consequently, the deflected tabs 20 can each exert a radial force directed toward the axial center of the vial adaptor 10 that is commensurate with the magnitude of their deflection so that the tabs 20 exert a reactive force on the vial and/or vial cap when the vial adaptor 10 is attached to the vial.

In some embodiments, each of the tabs 20 can also be configured so as to align the axial centerline of the vial adaptor 10 with the axial centerline of the vial to which the vial adaptor 10 is attached. For example, as shown most clearly in FIGS. 1, 3A, 5, and 8, the tabs 20 can each have an inside surface 26a and/or a depression 34 that are configured to contact a portion of the typically cylindrical outside surface 22a of the vial 22 (shown in FIG. 3A) or the typically cylindrical outside surface of the stopper 28 (shown in FIG. 3A) or cap 26. The inside surface 20a and/or depressions 34 can each bias the vial 22 to remain aligned with the axial centerline of the vial adaptor 10 and can prevent the tabs 20 from sliding laterally relative to the vial 22. With reference to FIGS. 5 and 8, in some embodiments, the depressions 34 can each define a first surface portion 34a that can be configured to contact a portion of the generally cylindrical outside surface 22a of the vial 22 (shown in FIG. 3A) or the cylindrical outside surface of the stopper 28 or other surface of the vial 22. As illustrated in FIGS. 5 and 8, the first surface portion 34a can define a curved surface. In some embodiments (not shown), the first surface portion 34a can define two generally planar surfaces defining a "V" shaped groove, which can be configured to contact a portion of the cylindrical outside surface 22a of the vial 22 or the generally cylindrical outside surface of the stopper 28 or cap 26 (see FIG. 2A) so as to bias the tabs 20 to remain aligned with the axial centerline of the vial 22 and to inhibit the tabs 20 from sliding laterally relative to the vial 22.

In some embodiments (not illustrated), the tabs 20 can each define a pair of protrusions or bumps that can be spaced apart from one another instead of the depression 34. In some embodiments, the protrusions or bumps can be configured to contact a portion of the typically cylindrical outside surface 22a of the vial 22 (shown in FIG. 3A) or the typically cylindrical outside surface of the stopper 28 (shown in FIG. 3A) or cap 26. Similar to the depressions 34 described above, among other things, the protrusions can bias the vial 22 to remain aligned with the axial centerline of the vial adaptor 10 and can prevent the tabs 20 from sliding laterally relative to the vial 22. The protrusions can be configured to contact a portion of the cylindrical outside surface 22a of the vial 22 or the generally cylindrical outside surface of the stopper 28 or cap 26 so as to bias the tabs 20 to remain aligned with the axial centerline of the vial 22 and to inhibit the tabs 20 from sliding laterally relative to the vial 22.

Additionally, as most clearly illustrated in FIG. 5, in some embodiments the depressions 34 can each comprise a second surface portion 34b. In some embodiments, the second surface portion 34b can be configured to interact with the planar surface or edge portion of a protruding lip portion 40 of a vial so as to bias the cap, stopper, or other protruding portion of a vial to remain positioned within the depression 34 of each tab 20 and to inhibit (but not necessarily prevent) further axial movement of the vial adaptor 10 into the vial 22. In some arrangements, the outermost portion of the second surface portion 34b can contact the cap, stopper, or other protruding portion of a vial so as to inhibit the vial adaptor 10 from further penetrating into the vial. In some arrangements, the first surface portion 34a can contact the cap, stopper, or other protruding portion of a vial. As will be discussed in greater detail, in some embodiments and for some vial configurations, the second surface portion 34b can be used as described above to bias the vial adaptor 10 to a predetermined depth in the vial 22 so as to maximize the amount of the contents of the vial 22 that can be extracted from the vial 22.

As most clearly illustrated in FIG. 9, the second surface portion 34b can comprise two planar surfaces defining a "V" shaped groove. In some embodiments (not shown), the second surface portion 34b can comprise a single planar surface that can be configured to bias the cap, stopper, or other protruding portion of a vial to remain positioned within the depression 34 of each tab 20 and to inhibit (but not necessarily prevent) further axial movement of the vial adaptor 10 into the vial. In some embodiments, the second surface portion 34b can define a curved surface that can be configured to bias the cap, stopper, or other protruding portion of a vial to remain positioned within the depression 34 of each tab 20 and to inhibit (but not necessarily prevent) further translation of the vial adaptor 10 into the vial.

Because the positioning of the second surface portion 34b can be used to control the depth of penetration of the penetrating portion 14 into the vial and, hence, the opening 24a relative to the stopper 28, the position of the second surface portion 34b relative to the opening 24a can be varied to enable the penetrating portion of each vial adaptor 10 to penetrate to a different distance as compared to another vial adaptor. Furthermore, the position of the second surface portion 34b relative to the inside surface 18a of the body portion 18 can be varied from one vial adaptor 10 to the next to enable each vial adaptor 10 to optimally work with a different range of vial sizes and stopper thicknesses.

As mentioned above, the penetrating portion 14 can comprise a cylindrical outer surface 14a and one axial openings 24 therethrough. As shown most clearly in FIG. 9, the opening 24a (which is sometimes referred to herein as the first opening) can pass through the entire penetrating portion 14, body portion 12, and interface portion 16, where it can be joined so as to be in communication with the opening 30. Thus, the opening 24a can provide a conduit through which the contents of the vial 22 can be extracted when the vial adaptor 10 is attached to the vial 22. The opening 24b (which is sometimes referred to herein as the second opening) can be in fluid communication with the transverse opening 36 to provide a conduit through which air can pass to fill the vial 22 and, hence, compensate for the displaced volume of the contents of the vial 22 that can be removed through the opening 24a. However, some embodiments of the vial adaptor 10 can be formed without a second opening (e.g., the opening 24b) or separate air vent. In these embodiments, the vial adaptor 10 can have only one opening (e.g., opening 24a) through which, at a minimum, fluid or medicament or other substance can be extracted from the vial.

In some embodiments, the vial adaptor 10 can comprise a filter member 38 that can be configured to prevent debris from contaminating the inside of the vial 22. In some embodiments, the filter member 38 can also be configured to prevent any bacteria, germs, viruses, or other contaminants from contaminating the inside of the vial 22. In the illustrated embodiment, the filter member 38 can be positioned inside of, or adjacent to, the transverse opening 36 and can be held in place with adhesive or by any other suitable attachment means.

In some embodiments (not illustrated), the vial adaptor 10 can comprise a one-way valve configured to prevent the contents of the vial 22 from leaking through the transverse opening 36, but to allow air to pass into the vial 22. The one-way valve can be formed separate from the filter member 38 or can be formed integrally with the filter member 38.

Figure 8B:
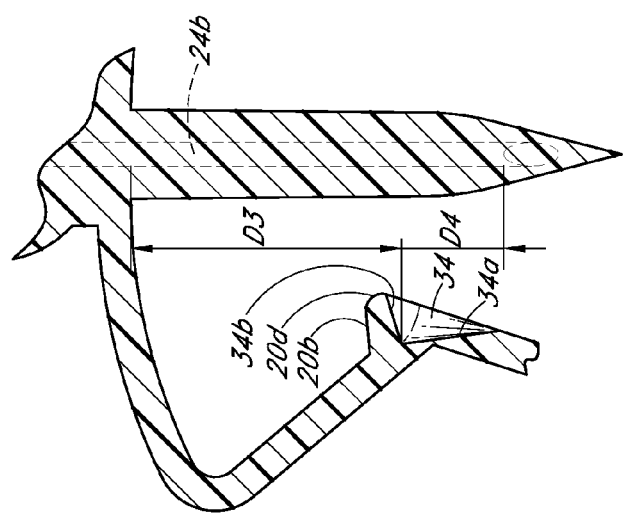
FIG. 8B is an enlarged section view of a portion of the embodiment of the vial adaptor of FIG. 1 generally defined by the curve 8B-8B in FIG. 8A.
Figure 8A:
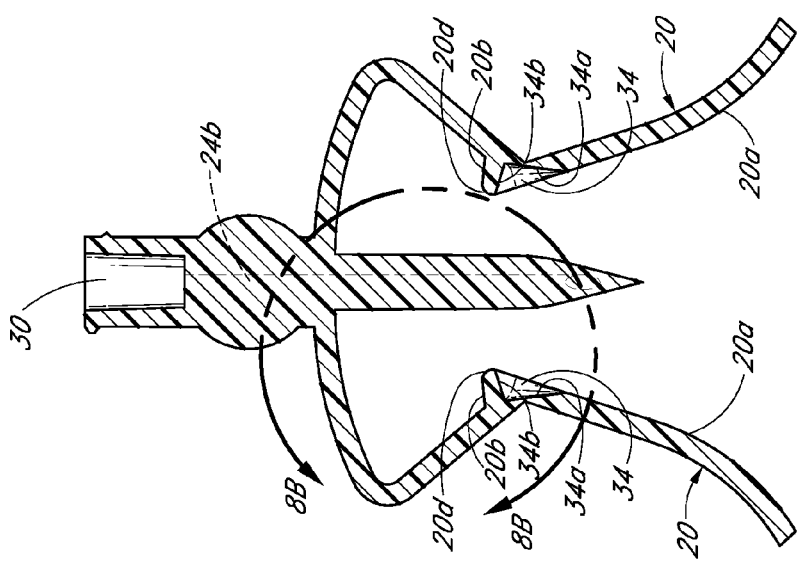
FIG. 8A is section view of the embodiment of the vial adaptor of FIG. 1 taken along the line 8A-8A in FIG. 4.

FIGS. 8A and 8B are a section view and an enlarged section of the vial adaptor 10, respectively, as defined in FIG. 4. With reference to FIGS. 8A-8B, the distance D3 represents the distance between the inside surface 18a of the body portion 18 and the outermost portion of the depression 34. In the illustrated embodiment, the outermost portion of the depression 34 coincides with the interconnection of the second surface portion 34b with the first surface portion 34a. In some embodiments, in the pre-stressed state, the vial adaptor 10 can be sized and configured such that the distance D3 is approximately 14 mm. In some embodiments, in the pre-stressed state, the vial adaptor 10 can be sized and configured such that the distance D3 can be significantly less than the length of the penetrating portion 14.

For example, in some embodiments, in the pre-stressed state, the distance D3 can be less than approximately ½ the length of the penetrating portion. The distance D3 can be from approximately 50% to approximately 60%, or from approximately 60% to approximately 70%, or from approximately 70% to approximately 80% of the length of the penetrating portion 14. In some embodiments, in the pre-stressed state, the vial adaptor 10 can be sized and configured such that the distance D3 is from approximately 9 mm to approximately 12 mm, or from approximately 12 mm to approximately 15 mm, or from approximately 15 mm to approximately 18 mm or to or from any value in these ranges. However, the vial adaptor 10 and any components or features thereof is not limited to the specific ranges or configurations described above. The vial adaptor 10 can be of any size or configuration that is suitable for the vial or vials for which the vial or vial adaptor 10 is intended to be used.

Further, with reference to FIG. 8B, the distance D4 represents the distance between the outermost portion of the depression 34 of the vial adaptor 10 in the relaxed state, as described above, and the top of the opening 24b. For example, in some embodiments, in the pre-stressed state, the vial adaptor 10 can be sized and configured such that the distance D4 is approximately 35% of the length of the penetrating portion 14, or from approximately 20% to approximately 30%, or from approximately 30% to approximately 40%, or from approximately 40% to approximately 50% of the length of the penetrating portion 14. In some embodiments, in the pre-stressed state, the vial adaptor 10 can be sized and configured such that the distance D4 is approximately 2 mm or from approximately 2 mm to approximately 4 mm, or from approximately 4 mm to approximately 6 mm or from or to any value in these ranges. In some embodiments, the distance between the outermost portion of the depression 34 of the vial adaptor 10 in the relaxed state, as described above, and the top of the first opening 24a can be the same as any of the values or ratios of D4 discussed above.

Additionally, in some embodiments, in the pre-stressed state, the vial adaptor 10 can be sized and configured such that the outermost portion of the depression 34 approximately coincides with, or is within approximately 2 mm of, the top of the opening 24a. However, the vial adaptor 10 and any components or features thereof is not limited to the specific ranges or configurations described above. The vial adaptor 10 can be of any size or configuration that is suitable for the vial or vials for which the vial adaptor 10 is intended to be used.

Similarly, the position of the opening 24a relative to the inside surface 18a can be varied. With reference to FIG. 7, distance D5 represents the distance between the inside surface 18a and the top of the opening 24a. In some embodiments, the vial adaptor 10 can be sized and configured such that the distance D5 is significantly less than the length of the penetrating portion 14. For example, in some embodiments, the distance D5 can be less than approximately half of the length of the penetrating portion. The distance D5 can be from approximately 40% to approximately 50%, or from approximately 50% to approximately 60%, or from approximately 60% to approximately 70% of the length of the penetrating portion 14. In some embodiments, the vial adaptor 10 can be sized and configured such that the distance D5 is equal to approximately 12 mm. In some embodiments, the vial adaptor 10 can be sized and configured such that the distance D5 is approximately 9 mm or from approximately 9 mm to approximately 11 mm, or from approximately 11 mm to approximately 13 mm, or from approximately 13 mm to approximately 15 mm or from or to any value in these ranges. However, the vial adaptor 10 and any components or features thereof is not limited to the specific ranges or configurations described above. The vial adaptor 10 can be of any size or configuration that is suitable for the vial or vials for which the vial adaptor 10 is intended to be used.

As described above, the position of the abutment surfaces 20b relative to the inside surface 18a of the body portion 18 can be varied from one vial adaptor 10 to the next (see distance D1 in FIG. 7). Further, the position of the distal end of the opening 24a relative to the inside surface 18a can be varied from one vial adaptor 10 to the next (see distance D5 above in FIG. 7). Accordingly, the position of the abutment surfaces 20b relative to position of the opening 24a can be varied from one vial adaptor 10 to the next. With reference to FIG. 7, distance D6 represents the distance between the abutment surfaces 20b and the top of the opening 24a, when the vial adaptor 10 is in a pre-installed state.

In some embodiments, in the pre-stressed state, the vial adaptor 10 can be sized and configured such that the distance D6 is significantly less than the length of the penetrating portion 14. For example, in some embodiments, in the pre-stressed state, the vial adaptor 10 can be sized and configured such that the distance D6 is approximately 5% of the length of the penetrating portion 14. For example, in some embodiments, in the pre-stressed state, the vial adaptor 10 can be sized and configured such that the distance D6 is from approximately 5% to approximately 10%, or from approximately 10% to approximately 15%, or from approximately 15% to approximately 20% of the length of the penetrating portion 14.

In some embodiments, in the pre-stressed state, the vial adaptor 10 can be sized and configured such that the distance D6 is approximately 2 mm. In some embodiments, in the pre-stressed state, the vial adaptor 10 can be sized and configured such that the distance D6 is from approximately 0.5 mm to approximately 1.5 mm, or from approximately 1.5 mm to approximately 2.5 mm, or from approximately 2.5 mm to approximately 3.5 mm or from or to any value in these ranges. However, the vial adaptor 10 and any components or features thereof is not limited to the specific ranges or configurations described above. The vial adaptor 10 can be of any size or configuration that is suitable for the vial or vials for which the vial adaptor 10 is intended to be used.

In some embodiments, the penetrating portion 14 can be configured such that the opening 24a terminates (i.e., passes through the wall of the penetrating portion 14) at an axial position on the penetrating portion 14 that is different than the point of termination of the opening 24b. In some embodiments, the penetrating portion 14 can be configured such that the opening 24a terminates at an axial position on the penetrating portion 14 that is closer to the inside surface 18a than the point of termination of the opening 24b. This configuration can allow air to pass through the end portion of the opening 24b at a point that is far enough removed from the opening 24a such that the air is not inadvertently drawn through the opening 24a as the contents of the vial are being extracted through the opening 24a. This configuration thus can prevent air bubbles from inadvertently entering the opening 24a when the vial is upside down and the contents of the vial are being extracted.

As mentioned, in some embodiments, the vial adaptor 10 can be sized and configured such that the end portion of the opening 24a is spaced apart from the end portion of the opening 24b. For example, in some embodiments, the vial adaptor 10 can be sized and configured such that the distance between the end portion of the opening 24a and the end portion of the opening 24b is approximately half of the diameter or size of the cross-section of the penetrating portion. The distance between the end of the portion of the opening 24a and the end portion of the opening 24b can be approximately 50% to approximately 65%, or from approximately 65% to approximately 80%, or from approximately 80% to approximately 95% of the diameter or size of the cross-section of the penetrating portion 14.

In some embodiments, the vial adaptor 10 can be sized and configured such that the end portion of the opening 24a can be approximately 1 mm away from the end portion of the opening 24b, or from approximately 1 mm to approximately 3 mm, or from approximately 3 mm to approximately 5 mm, or from approximately 5 mm to approximately 7 mm away from the end portion of the opening 24b. However, the vial adaptor 10 and any components or features thereof is not limited to the specific ranges or configurations described above. The vial adaptor 10 can be of any size or configuration that is suitable for the vial or vials for which the vial adaptor 10 is intended to be used.

Figure 10A:
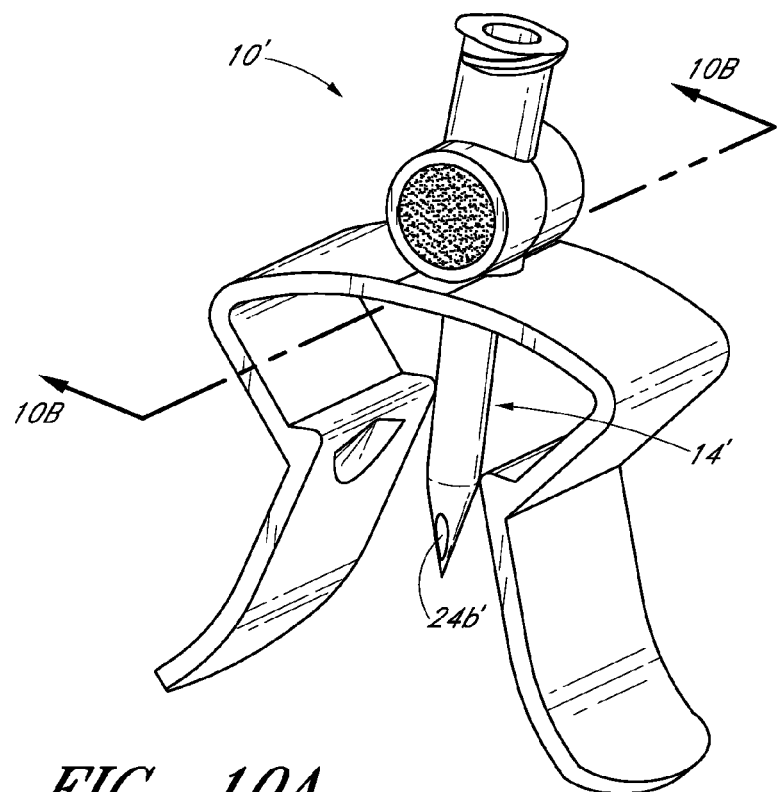
FIG. 10A is a perspective view of another embodiment of a vial adaptor.
Figure 10B:
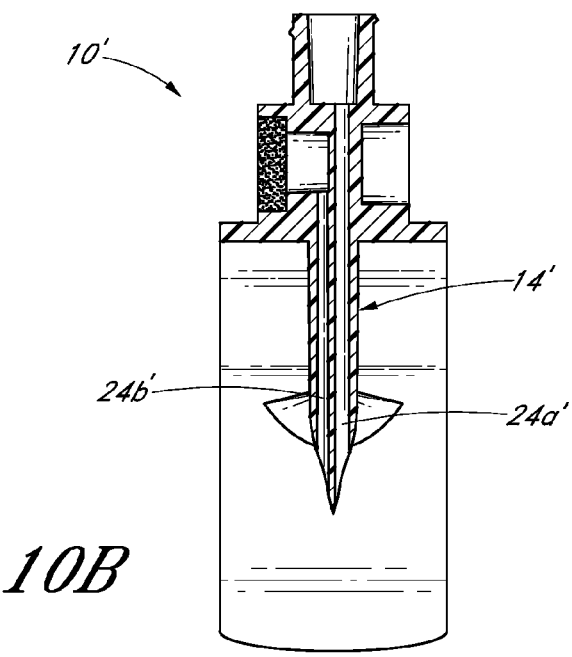
FIG. 10B is section view of the embodiment of the vial adaptor of FIG. 10A taken along the line 10B-10B in FIG. 10A.

For example, in some embodiments, the end portions of each of the openings 24a, 24b can be approximately aligned. For example, with reference to the vial adaptor 10' shown in FIGS. 10A-10B, which are a perspective view and section view of another embodiment of a vial adaptor 10', the penetrating portion 14' can be configured such that the end portion of the opening 24a' is approximately aligned with the end portion of the opening 24b'. The configuration of the penetrating portion 14' illustrated in FIGS. 10A, 10B can be used with any vial adaptor described herein.

Figure 11B:
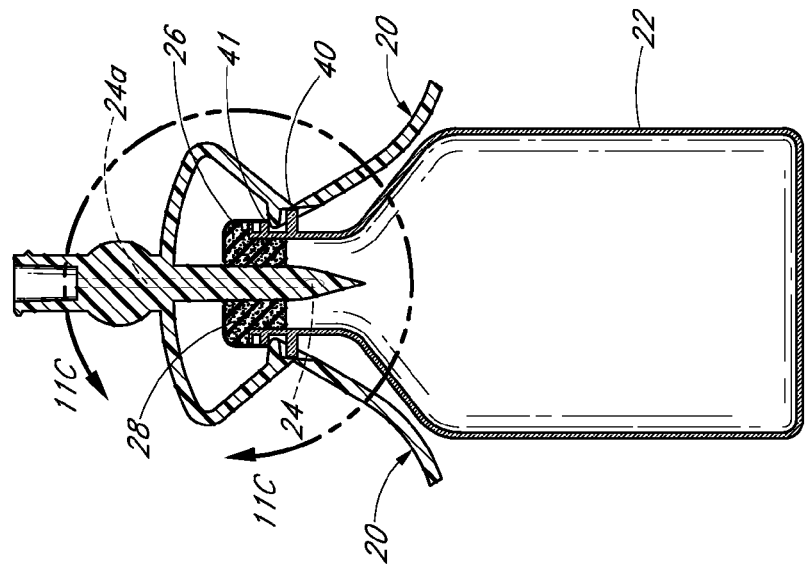
FIG. 11B is a section view of the embodiment of the vial adaptor of FIG. 1 inserted into a 20 mm vial, taken along the line 11B-11B in FIG. 11A.
Figure 11A:
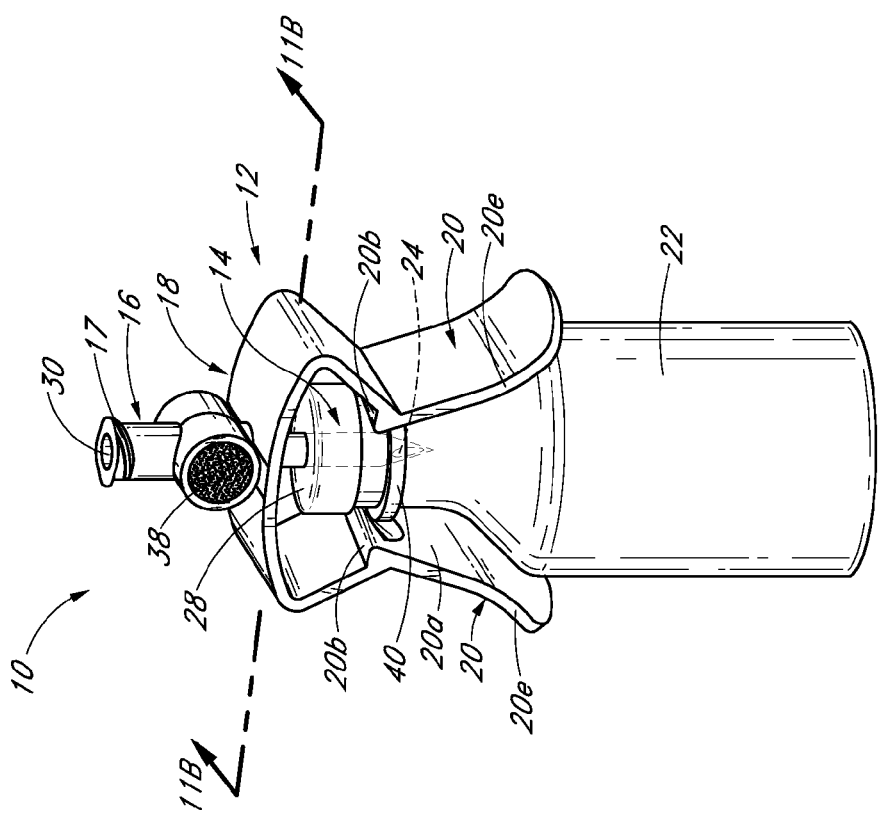
FIG. 11A is a perspective view of the embodiment of the vial adaptor of FIG. 1 inserted into a 20 mm vial.
Figure 11C:
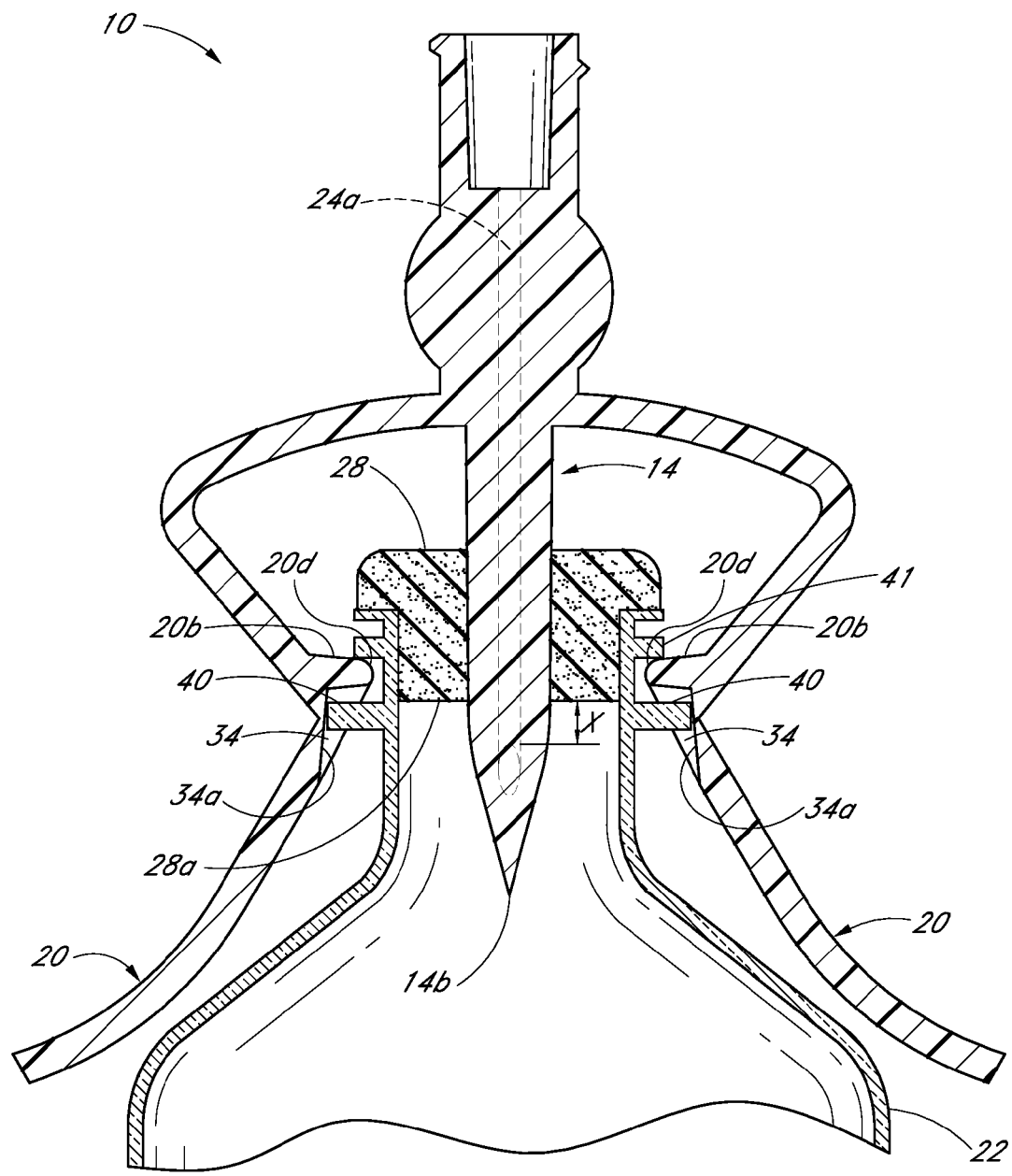
FIG. 11C is an enlarged section view of the embodiment of the vial adaptor of FIG. 1 inserted into a 20 mm vial, taken along curve 11C-11C in FIG. 11B.

FIG. 11A is a perspective view of the vial adaptor 10 inserted into a 20 mm vial 22. FIG. 11B is a section view from FIG. 11A taken along the line 11B-11B in FIG. 11A, and FIG. 11C is an enlarged section view from FIG. 1lB. FIGS. 11A-1-1C illustrate the configuration where the penetrating portion 14 of the vial adaptor 10 has already been inserted into the vial 22. As mentioned, to increase or optimize the amount of the contents that can be removed from the vial 22, the vial adaptor 10 can be configured such that the vial adaptor 10 is biased to affect the depth of the penetrating portion 14 into the vial 22.

As most clearly illustrated in FIG. 11C, as the vial adaptor 10 is being inserted into the vial 22, the protruding portions 20d can be biased to move into the space between the protruding lip portion 40 and the adjacent protruding lip portion 41. In some embodiments, as the vial adaptor 10 is being inserted into a vial, the protruding portions 20d can be biased to move into the space between a protruding lip portion and an adjacent planar surface of a stopper or cap, or other object attached to the vial. This can occur because the tabs 20 can be biased to exert a radial inward force against the vial 22, cap 26 and/or stopper 28 when the vial adaptor 10 is being attached to the vial 22. In other words, the tabs 20 can each contract inwardly toward their pre-stressed or pre-installed state such that the protruding portion 20d of each tab 20 moves into the necked or recessed portion of the vial 22 between the protruding lip portions 40 and 41, or between the protruding lip portion of the vial and the cap or stopper. In this arrangement, as the protruding portion 20d of each tab 20 moves further into the necked or recessed portion of the vial 22, the second surface portion 34b of each depression 34 (illustrated most clearly in FIGS. 8A-8B) can overlap an adjacent portion of the upper surface of the protruding lip portion 40 such that the vial adaptor 10 can be impeded or biased from being inserted further into the vial 22. In this configuration, the second surface portion 34b of each depression 34 can affect the depth of the penetrating portion 14 into the vial 22. Additionally, as discussed above, the abutment surfaces 20b can each be configured to prevent the vial adaptor 10 from being inadvertently removed from the vial 22 when the vial adaptor 10 is inserted into a vial. In some embodiments, this can be achieved when the vial adaptor 10 overlaps and abuts a protruding surface or surfaces on the vial 22, cap 26, or stopper 28.

As discussed above, the depth of the penetrating portion 14 into the vial 22 can affect the volume of the contents of the vial 22 that can be removed from the vial 22. With reference to FIG. 11C, the distance "X" represents the effective depth of the penetrating portion 14 into the vial 22. As used herein, the distance X is defined as the shortest distance between the interior fluid barrier surface 28a of the stopper 28 and the distal end of the opening 24a. As used herein, the fluid barrier surface 28a refers to the surface of the stopper or other sealing component that is most substantially exposed to the inside of the vial. In some seal arrangements, this can be a generally planar surface. In some seal arrangements, this can be a generally conical surface. In some seal arrangements, the fluid barrier surface can be concave or convex. It is not required for purposes of this description that the fluid barrier surface provide a completely leak proof barrier to the contents of the vial. The phrase "fluid barrier surface" is merely used to represent the innermost surface of the cap, septum, stopper, or other sealing object that defines surface of the stopper or other seal component.

Figure 12A:
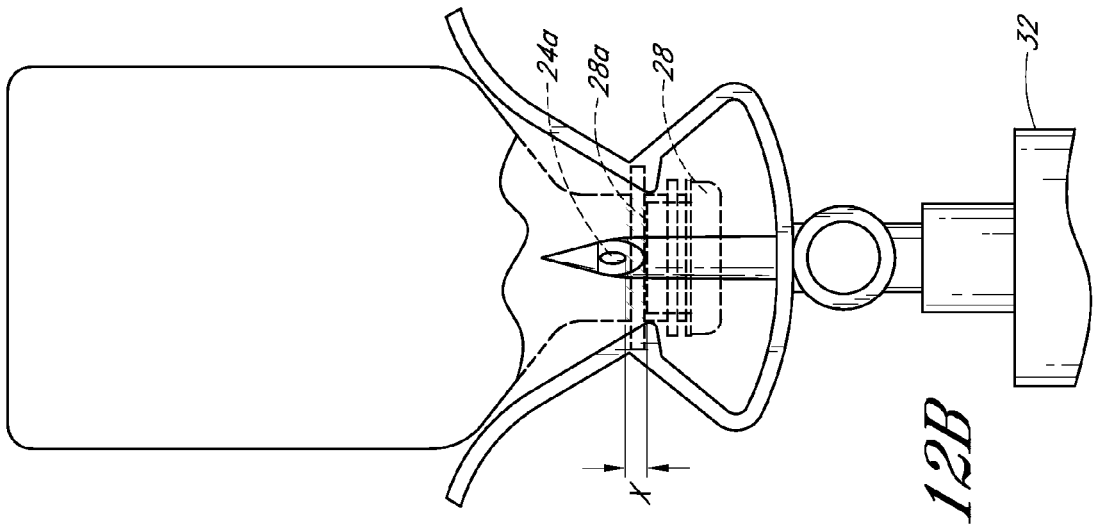
FIG. 12A is a side view of the embodiment of the vial adaptor of FIG. 1 inserted into a 20 mm vial, with a portion of the 20 mm vial and a fluid occupying the majority of the volume within the vial shown in dashed lines for clarity.
Figure 12B:
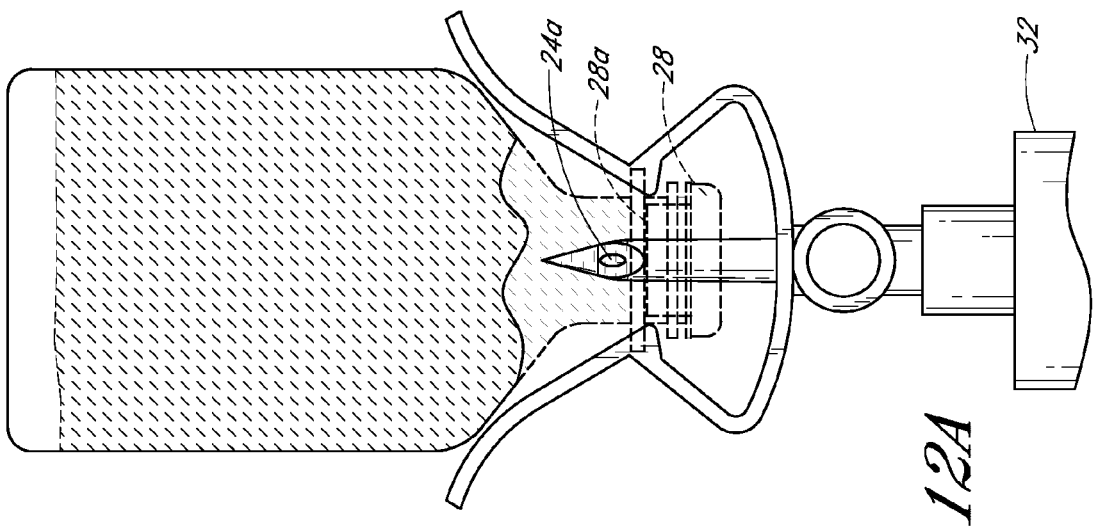
FIG. 12B is a side view of the embodiment of the vial adaptor of FIG. 1 inserted into a 20 mm vial, with a portion of the 20 mm vial and a fluid occupying the volume within the vial shown in dashed lines for clarity.

Because fluid is typically withdrawn from the vial 22 when the vial 22 is in an upside down orientation, as shown in FIGS. 12A and 12B, more fluid can generally be extracted through a vial adaptor 10 having a small value for distance X as compared to a vial adaptor 10 having a larger value for distance X. Thus, to increase or optimize the amount of medicament or other substance that can be extracted from the vial, the vial adaptor 10 can be configured so as to minimize the distance X. Therefore, in some embodiments, the vial adaptor 10 can be configured so that the distance from the fluid barrier surface 28a to the opening 24a is approximately the same when the vial adaptor 10 is attached to a wide range of vial sizes and configurations.

FIGS. 12A and 12B are side views of the vial adaptor 10 inserted into a 20 mm vial. In FIG. 12A, the contents of the vial occupy the majority of the volume of the vial 22. In FIG. 12B, only a limited amount of the volume of the vial 22 is occupied with fluid or medicament. A portion of the vial 22 and the contents of the vial 22 are shown in dashed lines for clarity. For reference, for each of the FIGS. 12A and 12B, the wavy line represents the break in the portion of the vial that is represented in solid lines versus the portion of the vial that is represented in dashed lines for clarity. With the vial in the upside down orientation as shown in FIGS. 12A and 12B (i.e., such that the outer septum surface is facing downward), the contents will accumulate above the inside surface 28a of the stopper 28. With reference to FIG. 12B, in some embodiments, the depth of the medication that is not extracted through the vial adaptor 10 is represented by the distance "X", which, again, is the distance from the opening 24a to the inside planar surface 28a of the stopper 28. In sum, the vial adaptor 10 can be configured to minimize the value of X so that the majority of the medication or contents of the vial 22 can be extracted by the vial adaptor 10.

When the user desires to remove the vial adaptor 10, the abutment surfaces 20b can be disengaged from the protruding vial lips, stopper 28, or cap 26 by spreading the tabs 20 away from one another until the abutment surfaces 20b no longer overlap protruding vial lips, stopper 28, or cap 26. The vial adaptor 10 can then be removed by exerting an axial force on the vial adaptor 10 away from the vial 22.

As mentioned, in the illustrated embodiment, the vial adaptor 10 can be configured to minimize the distance X over a wide range of vial sizes that the vial adaptor 10 is attached to.

In some embodiments, the vial adaptor 10 (or any other vial adaptors disclosed herein, including but not limited to vial adaptor 110 described below) can be configured so as to be inserted into any sized vial, including but not limited to vials having an opening diameter approximately equal to 8 mm, 11 mm, 13 mm, 17 mm, 20 mm, 28 mm, or other available or suitable vial sizes. Any dimension, dimensional range, or configuration described in this application is meant to be exemplary, but not limiting. The dimensional ranges set forth herein can be scaled to permit the vial adaptor 10 to work with any suitable vial. When the vial adaptor 10 is attached to a vial as described herein, the opening 24a in the penetrating portion 14 can be positioned inside the otherwise sealed space of the vial.

Figure 13A:
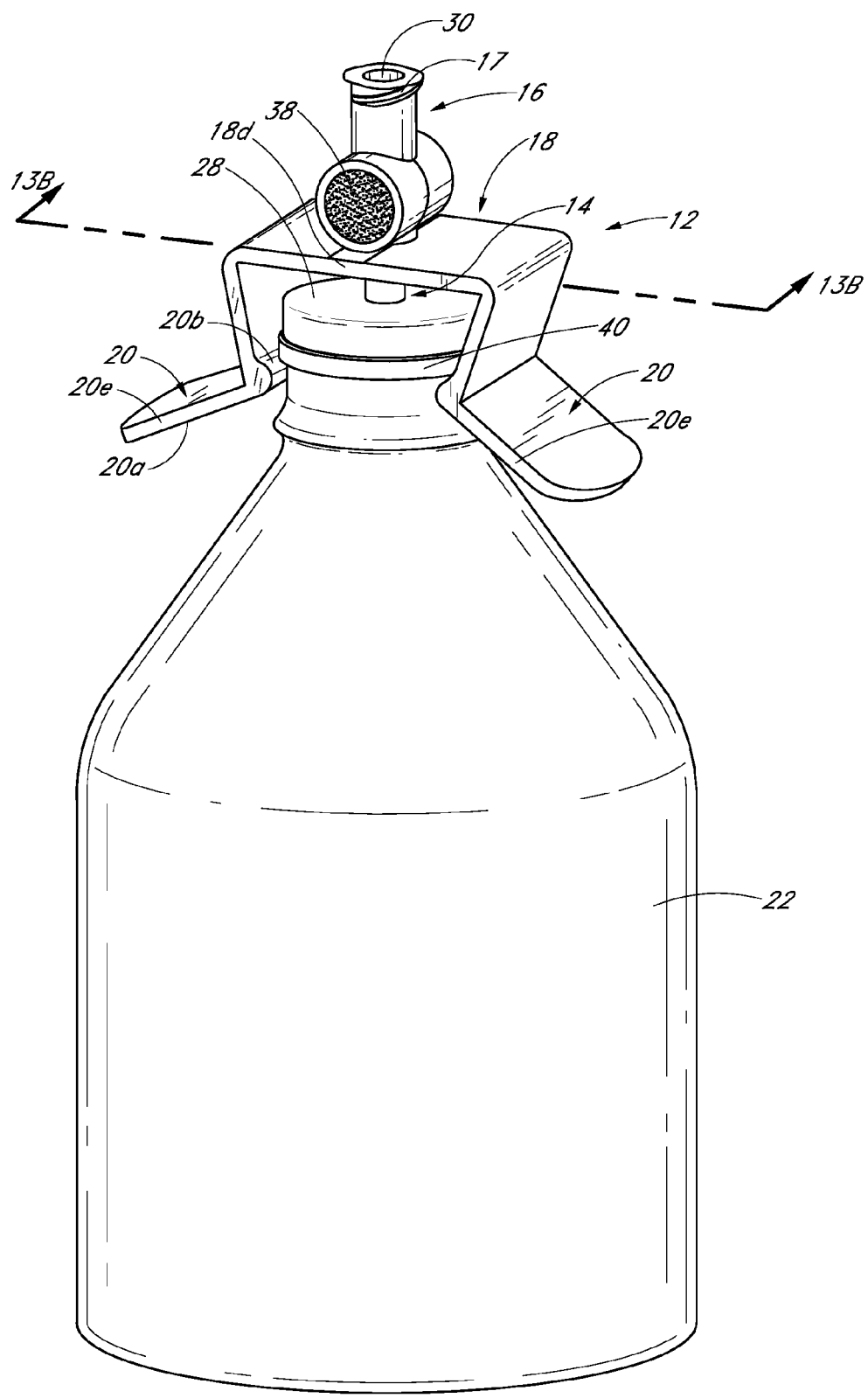
FIG. 13A is a perspective view of the embodiment of the vial adaptor of FIG. 1 inserted into a 28 mm vial.
Figure 13B:
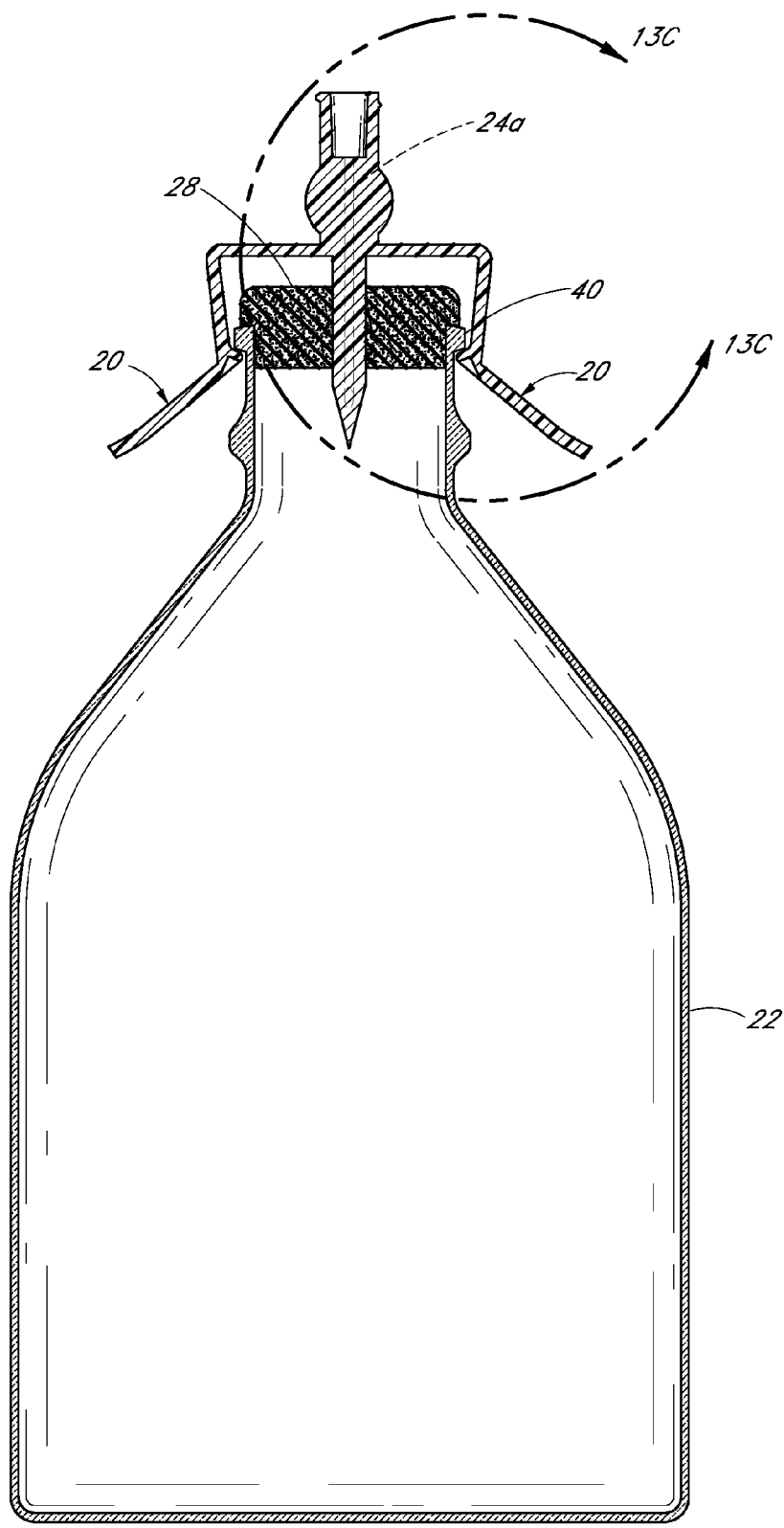
FIG. 13B is a section view of the embodiment of the vial adaptor of FIG. 1 inserted into a 28 mm vial, taken along the line 13B-13B in FIG. 13A.
Figure 13C:
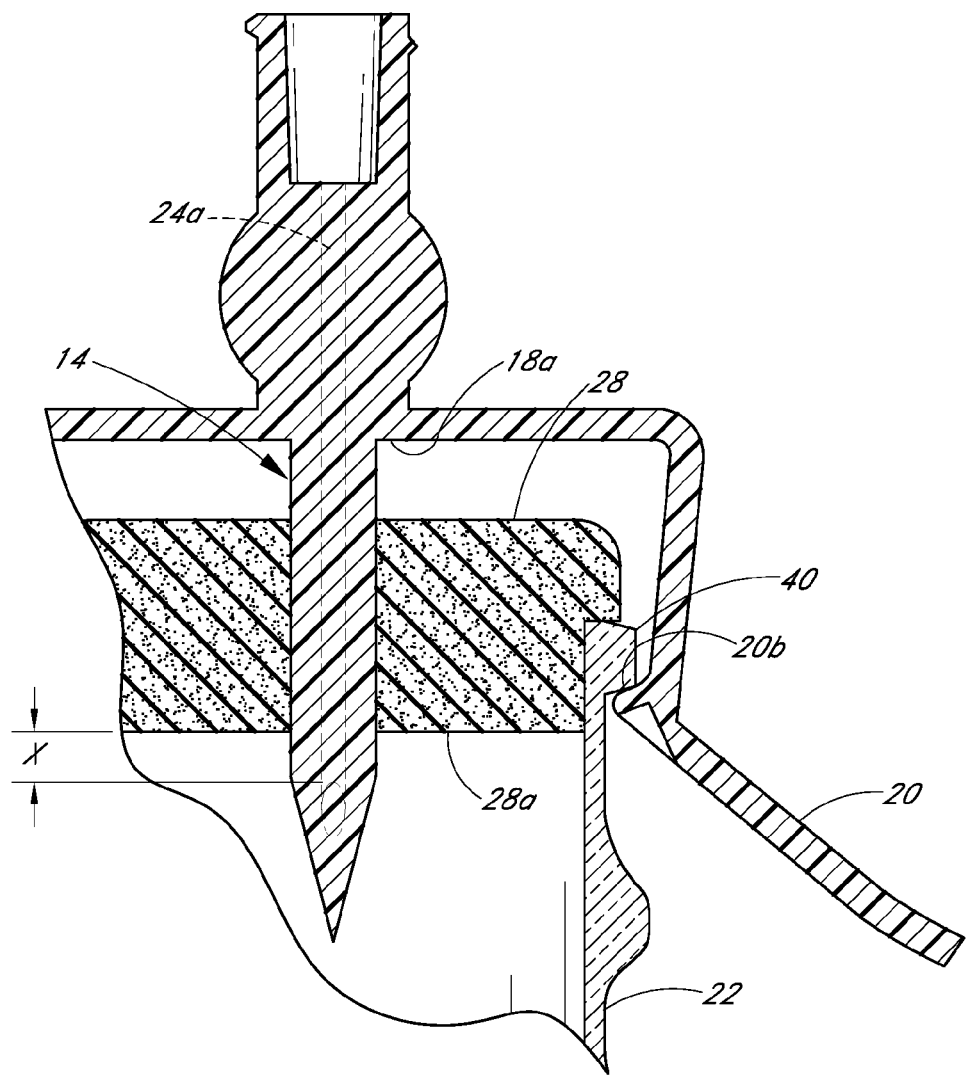
FIG. 13C is an enlarged section view of a portion of the embodiment of the vial adaptor of FIG. 1 inserted into a 28 mm vial, taken along curve 13C-13C in FIG. 13B.

In some embodiments, the vial adaptor 10 can be inserted into a 28 mm vial 22 as shown in FIGS. 13A-13C, which are perspective, sectional, and enlarged section views of the vial adaptor 10 inserted into a 28 mm vial. As illustrated most clearly in FIG. 13C, the penetrating portion 14 of the vial adaptor 10 can be inserted through a cap (not shown) and/or stopper 28 on the 28 mm vial 22 so that the opening 24a (shown in dashed lines) is below the inside planar surface 28a and, hence, inside the vial 22. Again, the "X" represents the distance between the fluid barrier surface 28a of the stopper 28 and the opening 24a.

As previously described, the vial adaptor 10 can be configured to limit the depth to which the engagement portion 14 of the vial adaptor 10 can penetrate through the stopper 28 of the 28 mm vial. In particular, the vial adaptor 10 can be configured such that, when the vial adaptor 10 is inserted into the vial 22, the penetrating portion 14 protrudes through the stopper 28 to a distance so as to increase the amount of the contents that can be removed from the vial 22. In the illustrated embodiment, the inside surface 18a of the central portion 18 of the vial adaptor 10 can be curved. In some embodiments, the curvature of the inside surface 18a can be sized and configured to control the depth of the penetrating portion 14 into the vial 22.

As mentioned, the central portion 18 can be sized and configured such that the vial adaptor 10 can be attached to a wide range of vials 22 that have a wide range of cap or stopper diameters. In some embodiments (not illustrated), the vial adaptor 10 can be inserted into the vial 22 until the inside surface 18a of the central portion 18 contacts the top of the cap, stopper 28, or vial 22, whichever component surface is first contacted. Additionally, in some embodiments, when the vial adaptor 10 is so inserted, the tabs 20 can constrict around the cap, stopper 28, or protruding lip portions of the vial, such as protruding lip portion 40 in the illustrated embodiment. This can cause the abutment surfaces 20b to overlap with the bottom surface of the cap, stopper 28, or protruding lip portions 40 of the vial 22, thus removably securing the vial adaptor 10 to the vial 22. When the user desires to remove the vial adaptor 10, the abutment surfaces 20b can be disengaged from the cap, stopper 28, or protruding lip portion 40 of the vial 22 by spreading the tabs 20 away from one another until the abutment surfaces 20b no longer overlap the cap 28 or protruding lip portions 40. The vial adaptor 10 can then be removed by exerting an axial force on the vial adaptor 10 away from the vial 22.

Figure 14B:
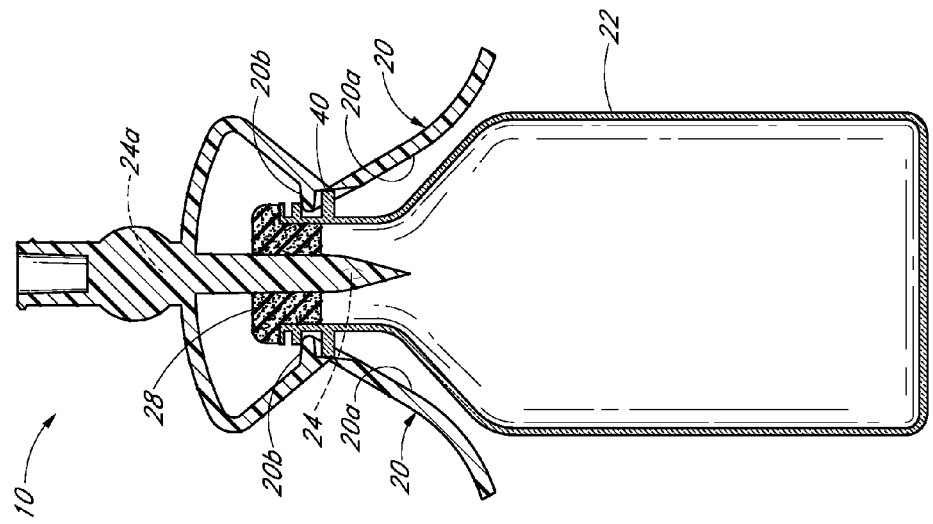
FIG. 14B is a section view of the embodiment of the vial adaptor of FIG. 1 inserted into a 13 mm vial, taken along the line 14B-14B in FIG. 14A.
Figure 14A:
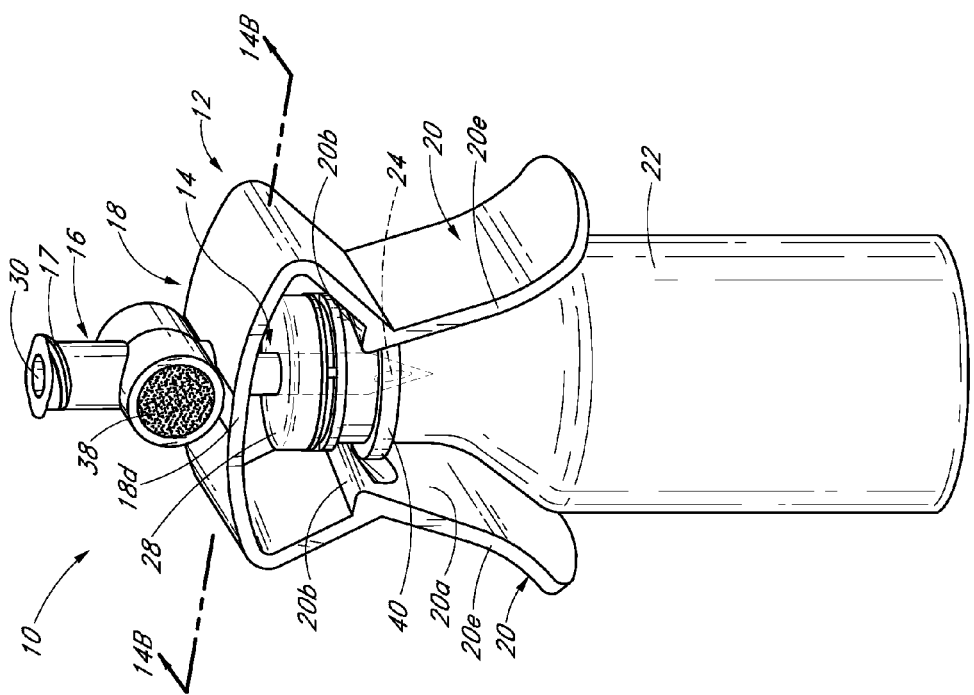
FIG. 14A is a perspective view of the embodiment of the vial adaptor of FIG. 1 inserted into a 13 mm vial.

FIG. 14A is a perspective view of the vial adaptor of FIG. 1 inserted into a 13 mm vial, and FIG. 14B is a section view of the vial adaptor of FIG. 1 inserted into a 13 mm vial, as defined in FIG. 14A. As illustrated therein, the vial adaptor 10 can be configured to be attached to and removed from the 13 mm vial 22 in a similar fashion as with respect to the 20 mm vial described above. In particular, the vial adaptor 10 can be inserted until the protruding lip portion 40 comes into contact with the depression 34, at which point the vial adaptor 10 will be inhibited or biased from penetrating further into the vial 22, and the opening 24a can be at an optimal distance from the stopper 28.

Figure 15A:
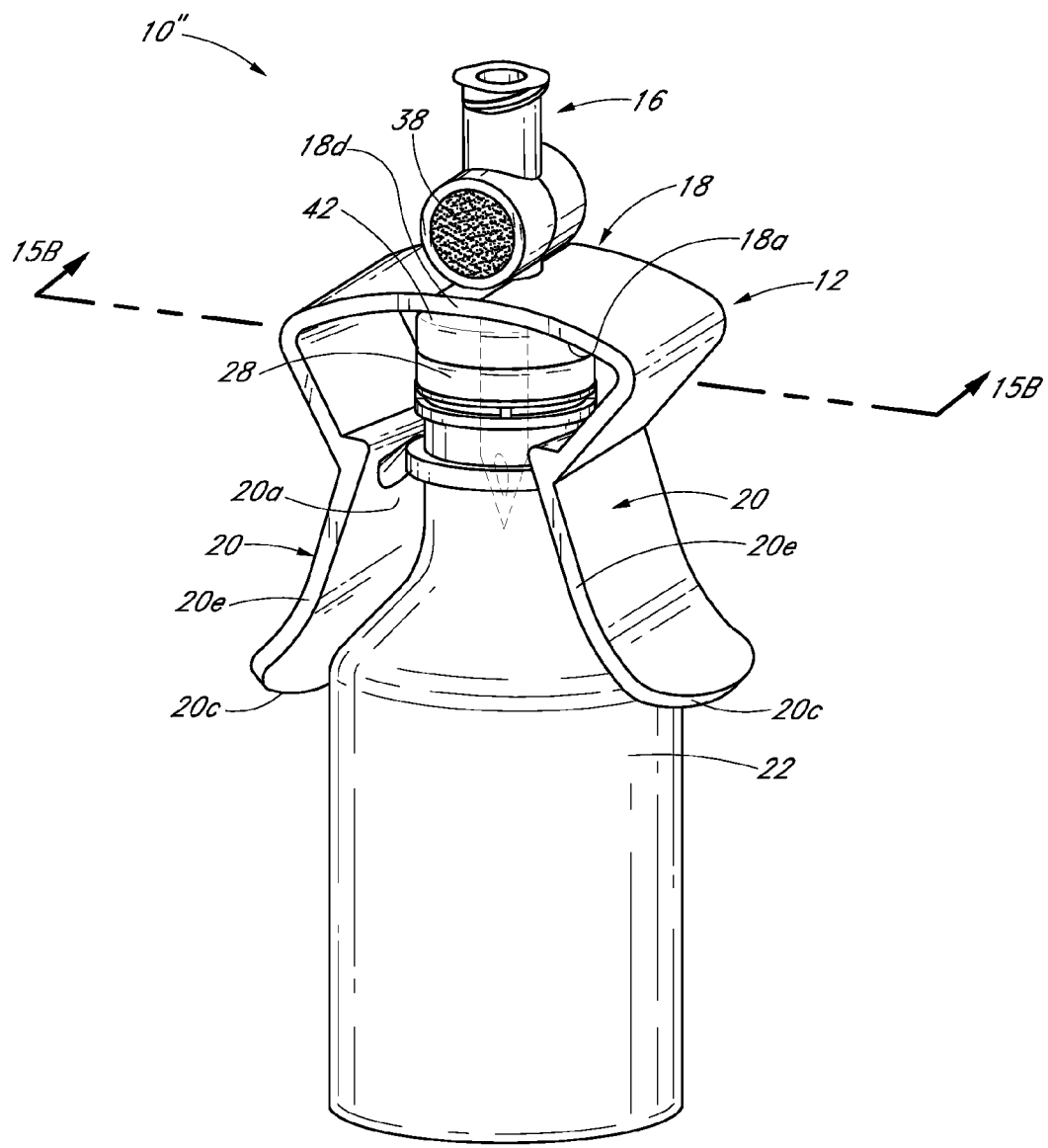
FIG. 15A is a perspective view of another embodiment of a vial adaptor inserted into a 13 mm vial.
Figure 15B:
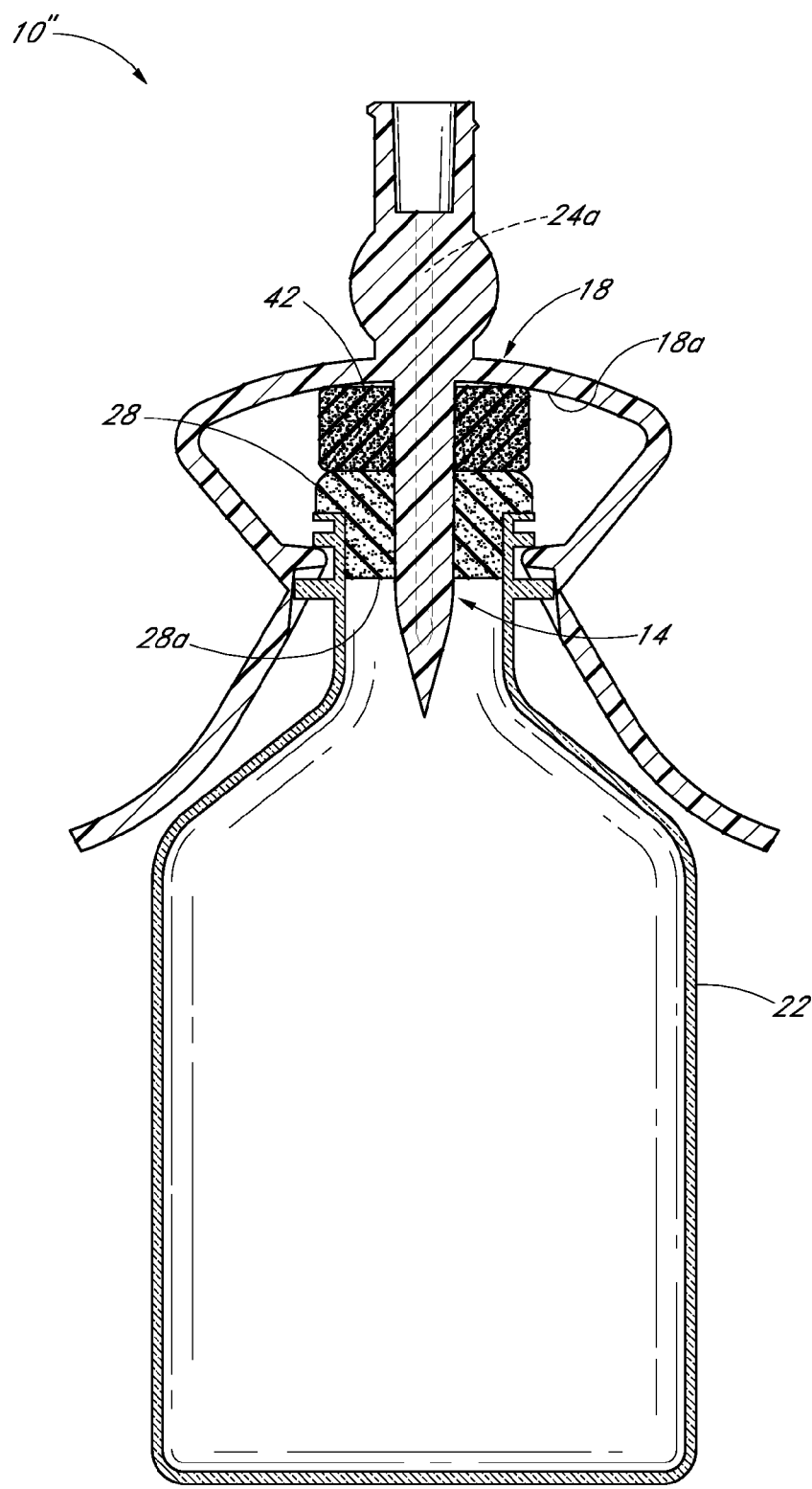
FIG. 15B is a section view of the embodiment of the vial adaptor of FIG. 15A inserted into a 13 mm vial, taken along the line 15B-15B in FIG. 15A.

FIG. 15A is a perspective view of another embodiment of a vial adaptor 10" inserted into a 13 mm vial, and FIG. 15B is section view of the vial adaptor 10" inserted into a 13 mm vial, taken along the line 15B-15B in FIG. 15A. The vial adaptor 10" can comprise any of the features or configurations described above, and can also comprise a spacer 42 that can define an axial opening therethrough through which the penetrating portion 14 of the vial adaptor 10" can pass. The spacer 42 can be used to increase or optimize the depth of the opening 24a below the fluid barrier surface 28a of the stopper 28, by providing a limit to which the vial adaptor 10" can penetrate into the vial 22. As illustrated in FIGS. 15A and 15B, the spacer 42 can be positioned between the inside surface 18a of the central portion 18 and the top of the cap (not shown) or stopper 28. The spacer 42 can prevent the vial adaptor 10" from further penetration into the vial adaptor 10" in the axial direction, based on the thickness of the spacer 42.

The spacer 42 can be sized and configured to control the depth to which the vial adaptor 10" can penetrate the vial 22 according to the size, shape, and configuration of the vial 22. Accordingly, the spacer 42 can be formed according to a widely ranging variety of sizes and shapes in accordance with the size and shape of the vial adaptor and vial, or other component, that the spacer 42 and vial adaptor 10" is to be used with and can be easily interchanged or stacked in series with one or more other spacers 42. The spacer 42 can be used with any suitable vial adaptor or vial, such as, but not limited, those described herein. For example, without limitation, the spacer 42 can be used with the configuration of the 28 mm vial illustrated in FIGS. 13A-13C by positioning the spacer between the top of the vial 22 (or cap or stopper 28) and the inside surface 18a, so that the depth that the penetrating portion 14 protrudes into the vial 22 can be reduced by an amount approximately equal to the thickness of the spacer 42. However, in some embodiments, the vial adaptor 10 can sufficiently engage the cap of the vial 22 so that the abutment surfaces 20b overlap and engage an opposing face of the cap (if any), stopper 28, or vial 22, so as to prevent the vial adaptor 10 from becoming inadvertently removed from the vial 22. Accordingly, the spacer 42 can also be used to ensure a snug fit with the portion of the vial 22 that is secured between the abutment surfaces 20b and the inside surface 18a.

In some embodiments, the thickness of the spacer 42 in the axial direction can be from approximately 1 mm to approximately 4 mm, or from approximately 4 mm to approximately 7 mm, or from approximately 7 mm to approximately 10 mm or from or to any value in these ranges. In some embodiments, the thickness of the spacer 42 in the axial direction can be from approximately from approximately 5% to approximately 12.5%, or from approximately 12.5% to approximately 20%, or from approximately 20% to approximately 27.5% of the length of the penetrating portion 14. However, the spacer 42 is not limited to the specific ranges or configurations described above. The spacer 42 can be of any size or configuration that is suitable for the vial or vials for which the vial adaptor 10 is intended to be used.

The spacer 42 can be made from any suitable material, but can be made from plastic or rubber, such as, but not limited to, silicone or neoprene. Furthermore, in some embodiments, the spacer 42 can be integrally formed with, or attached to, the inside surface 18a of the vial adaptor 10. In some embodiments, the spacer 42 can be attached to the inside surface 18a with adhesive, a hook and loop fastener, or by any suitable means.

The body portion 12, penetrating portion 14, and interface portion 16, or any other component or components of the vial adaptors described herein can be made from any suitable material such as, but not limited to, polycarbonate or other suitable polymeric or plastic materials. In some embodiments, one or more components of the vial adaptors described herein can be made from a hydrophobic material, such as Bayer Makrolon. The material chosen to make one or more of these components can be substantially fluid impervious and can be suitable for use with a wide range of medicaments.

In some embodiments, the body portion 12, penetrating portion 14, and interface portion 16 can be integrally formed in the same manufacturing step, such as in a plastic injection molding operation. In some embodiments, the body portion 12, penetrating portion 14, and interface portion 16 can be formed in separate manufacturing steps and fused, bonded, or otherwise attached together by any suitable method or with any suitable adhesive material. The filter member 38 can be attached to the vial adaptor 10 in a separate manufacturing step. The openings 24a, 24b can be formed in the vial adaptor 10 at the same time the body portion 12, penetrating portion 14, and interface portion 16 are formed, or can be formed in a subsequent step or process. The body portion 12, penetrating portion 14, and interface portion 16 can be made from a plastic, composite material, or other elastically deformable, semi-rigid material that is suitable for use in the medical field.

Figure 16:
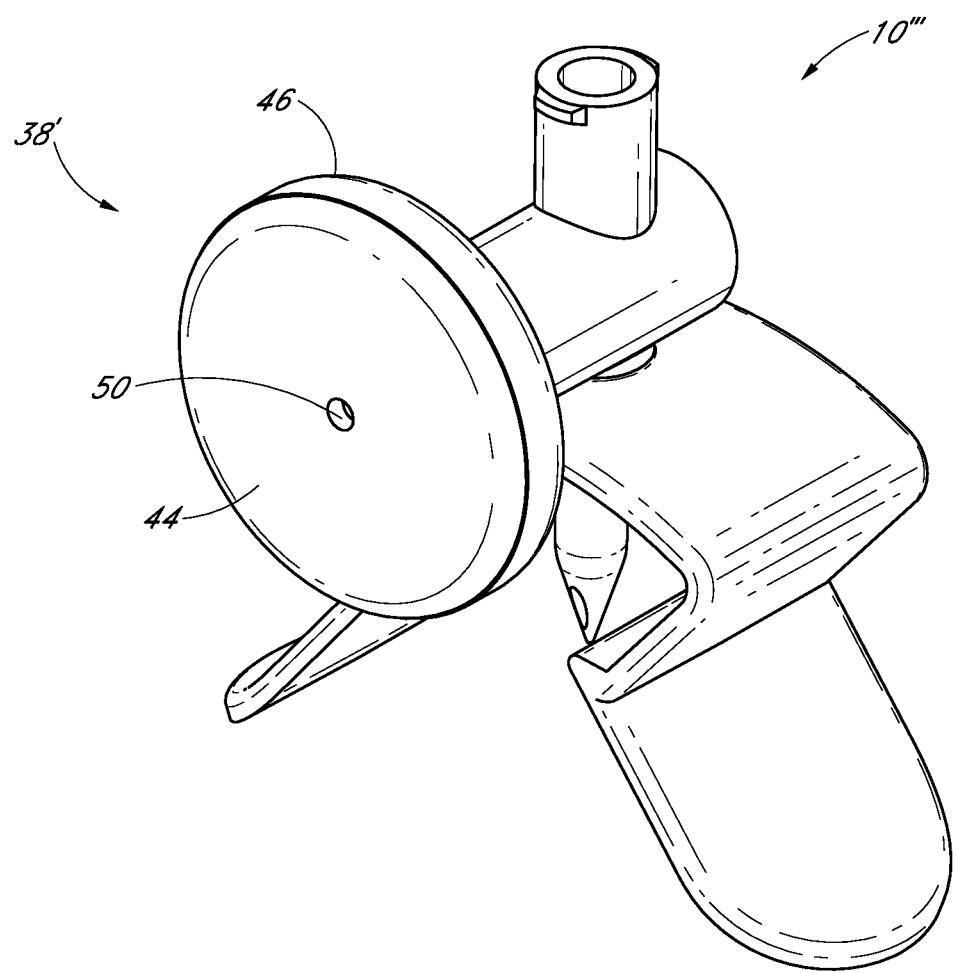
FIG. 16 is a perspective view of another embodiment of a vial adaptor.
Figure 17:
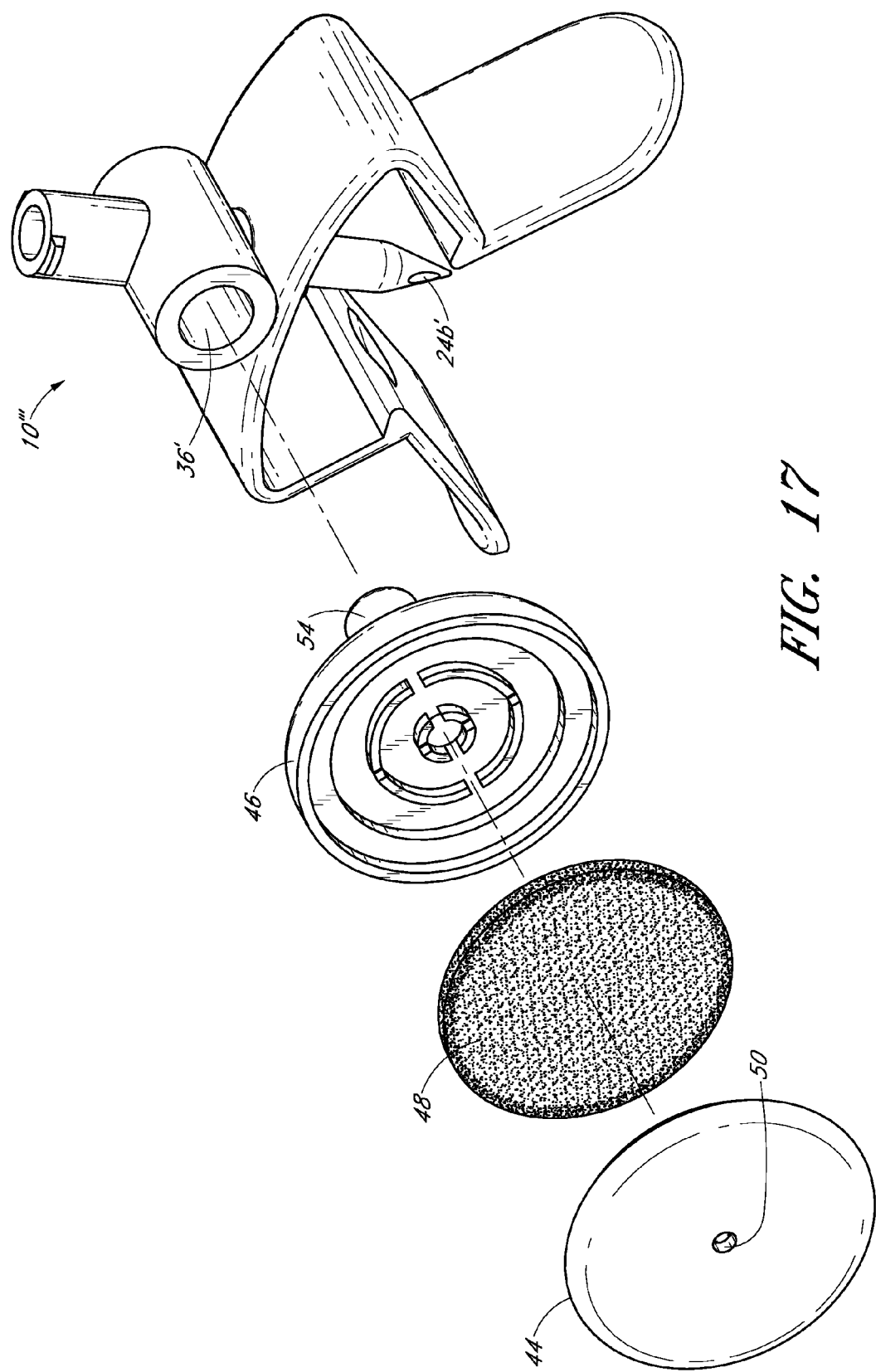
FIG. 17 is an exploded perspective view of the embodiment of the vial adaptor shown in FIG. 16.

FIG. 16 is a perspective view of another embodiment of a vial adaptor 10'" having a filter member 38'. FIG. 17 is an exploded perspective view of the embodiment of the vial adaptor 10'" shown in FIG. 16. With reference to FIGS. 16-17, in some embodiments, the vial adaptor 10'" can be the same or similar to any other vial adaptor embodiments disclosed herein, or can have any of the features or other details of any other vial adaptor disclosed herein, including but not limited to the embodiments of the vial adaptor 10, 10', and 10", the embodiments described below, and the embodiments of the vial adaptors incorporated herein by reference.

Figure 18:
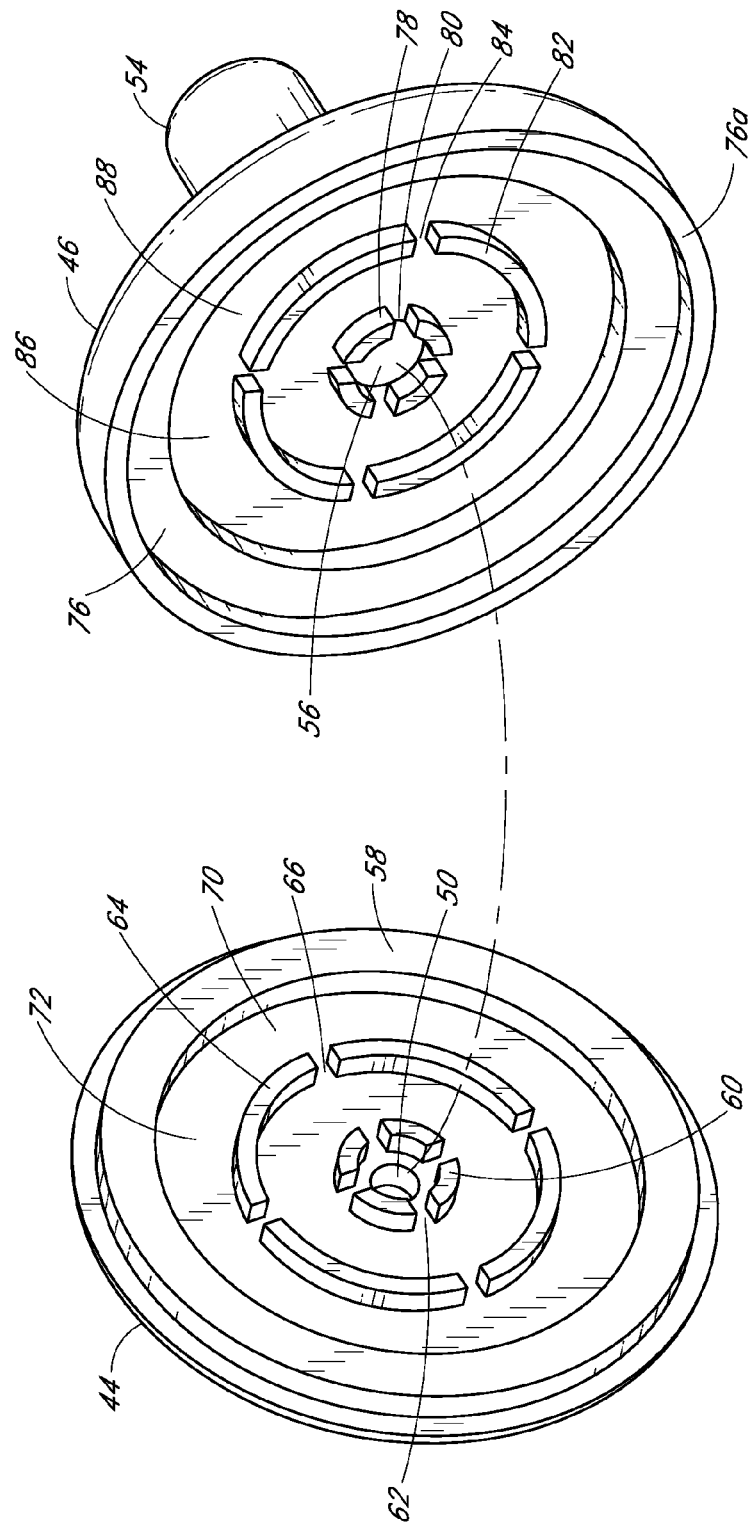
FIG. 18 is an exploded perspective view of some of the components of the embodiment of the filter member shown in FIG. 16.

FIG. 18 is an exploded perspective view of some of the components of the embodiment of the filter member 38' shown in FIG. 16. FIG. 19 is a top view of the embodiment of the filter member 38' shown in FIG. 16. FIG. 20 is a section view of the embodiment of the filter member 38' shown in FIG. 16, taken through line 20-20 in FIG. 19. With reference to FIGS. 16-20, the vial adaptor 10'" can be configured to support a filter member 38' comprising a cover 44, a base 46, and a membrane 48. The cover 44 can be substantially sealingly received by the base 46 so that substantially all of the air that is permitted to flow through the filter member 38' flows through an opening 50 formed in the cover 44.

The cover 44 can be press-fit with or otherwise attached to the base 46 using adhesive, sonic welds, or by any other similar or suitable means. For example, as illustrated in FIG. 20, the cover 44 can be attached to the base 46 with one or more sonic welds 52. As illustrated most clearly in FIG. 20, the cover 44 and the base 46 can be joined together so that the annular protrusion 58 of the cover 44 is adjacent to the annular protrusion 76 on the base 46. The protrusion 76 can have a stepped or extended lip portion 76a that can overlap the protrusion 58 formed on the cover 44 in the assembled configuration.

In some embodiments, the perimeter of the filter member 38' can define a non-circular shape, such as a square, triangular, polygonal, or other suitable or desired shape. Additionally, the diameter or area of the membrane 48 and, accordingly, the filter member 38', can be selected so that a sufficient amount of air can flow through the filter member 38' during extraction of the liquid or other substance from the vial. In some embodiments, the cross-sectional area of the filter membrane 48 can be significantly larger than the cross-sectional area of the opening 36' and/or the opening 24b'.

For example, without limitation, in some embodiments, the cross-sectional area of the filter membrane 48 can be approximately 9 times greater than the cross-sectional area of the opening 36'. In some embodiments, the cross-sectional area of the filter membrane 48 can be between approximately 2 times greater and approximately 5 times greater, or between approximately 5 times greater and approximately 8 times greater, or between approximately 8 times greater and approximately 11 times greater than the cross-sectional area of the opening 36', or to or from any values within these ranges.

Similarly, without limitation, in some embodiments, the cross-sectional area of the filter membrane 48 can be approximately 400 times greater than the cross-sectional area of the opening 24b'. In some embodiments, the cross-sectional area of the filter membrane 48 can be between approximately 100 times greater and approximately 250 times greater, or between approximately 250 times greater and approximately 400 times greater, or between approximately 400 times greater and approximately 550 times greater than the cross-sectional area of the opening 24b', or to or from any values within these ranges.

As illustrated, the membrane 48 can be configured to remove or diminish particulate matter such as dirt or other debris, germs, viruses, bacteria, and/or other forms of contamination from the air flowing into the vial adaptor 10'''. The membrane 48 can be formed from any suitable filter material. In some embodiments, the membrane 48 can be hydrophobic and can have a mean pore size of approximately 0.1 micron, or between approximately 0.1 micron and approximately 0.5 micron. Additionally, the cover 44 and the base 46 can be formed from any suitable material, including but not limited to any other material disclosed herein regarding any other component or feature of any embodiments of the vial adaptor disclosed herein.

With reference to FIGS. 16-20, the filter member 38' can be supported by an opening 36' formed in the vial adaptor 10'''. In particular, a protrusion or boss 54 extending from the base 46 can be configured to be substantially sealingly received within or around the outer perimeter of the opening 36' formed in the vial adaptor 10'''. In some embodiments, the boss 54 can be press-fit into the opening 36' so as to create a generally sealed connection between the boss 54 and the opening 36'. In some embodiments, adhesive, welds, or other materials or features can be used to provide the connection between the boss 54 and the opening 36'. An opening 56 can be formed through the boss 54 so that air flowing through the opening 50 formed in the cover 44 will be filtered by the membrane 48 before flowing through the opening 56 formed in the base 46 and into the opening 36' formed in the vial adaptor 10''', as will be described in greater detail below. As with the opening 36 formed in the vial adaptor 10 described above, the opening 36' can be configured to be in fluid communication with the opening 24b' (which is sometimes referred to herein as the second opening) so as to provide a conduit through which air can pass to fill a vial and, hence, compensate for the displaced volume of the contents of the vial that can be removed through the vial adaptor 10'''.

The protrusion 54 can be sized and configured to have a sufficient wall thickness and diameter to ensure that the protrusion 54 is not inadvertently broken during use by an inadvertent contact with the filter member 38'. Additionally, the size of the opening 56 formed through the protrusion 54, as well as the opening 50 formed in the cover 44, can be designed to ensure a sufficient amount of airflow through the filter member 38'. Accordingly, the diameter of the opening 36' formed in the vial adaptor 10''' can be adjusted to accommodate any desired or suitable outside diameter of the protrusion 54.

With reference to FIGS. 18-19, the cover 44 can have an outer annular protrusion 58, a first inner annular protrusion 60 having one or more openings 62 therethrough, and a second inner annular protrusion 64 having one or more openings 66 therethrough. When the cover 44 is assembled with the base 46 and the membrane 48, the annular protrusions 58, 60, 64 and the openings 62, 66 can form a volume of space 70 between the inner planar surface 72 of the cover 44 and the planar surface of the membrane 48 into which the air can flow and circulate before passing through the membrane 48.

Similarly, the base 46 can have an outer annular protrusion 76, a first inner annular protrusion 78 having one or more openings 80 therethrough, and a second inner annular protrusion 82 having one or more openings 84 therethrough. When the base 46 is assembled with the cover 44 and the membrane 48, the annular protrusions 76, 78, 82 and the openings 80, 84 can form a volume of space 86 between the inner planar surface 88 of the base 46 and the planar surface of the membrane 48 into which the air can flow and circulate after the air has passed through the membrane 48. Thus, in this configuration, air can flow through the opening 50 formed in the cover 44 into the space 70 defined between the cover 44 and the membrane 48, through the membrane 48 into the space 86 defined between the membrane 48 and the base 46, through the opening 56 formed in the base 46, and into the opening 36' formed in the vial adaptor 10'''.

Figure 24:
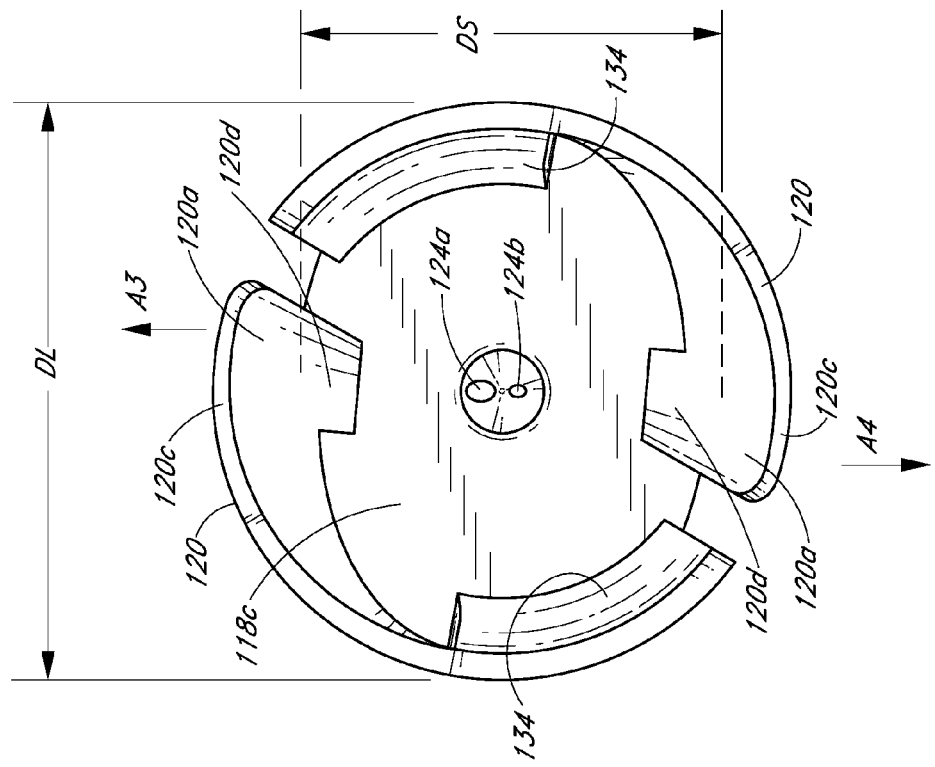
FIG. 24 is a bottom view of the embodiment of the vial adaptor shown in FIG. 21.
Figure 23:
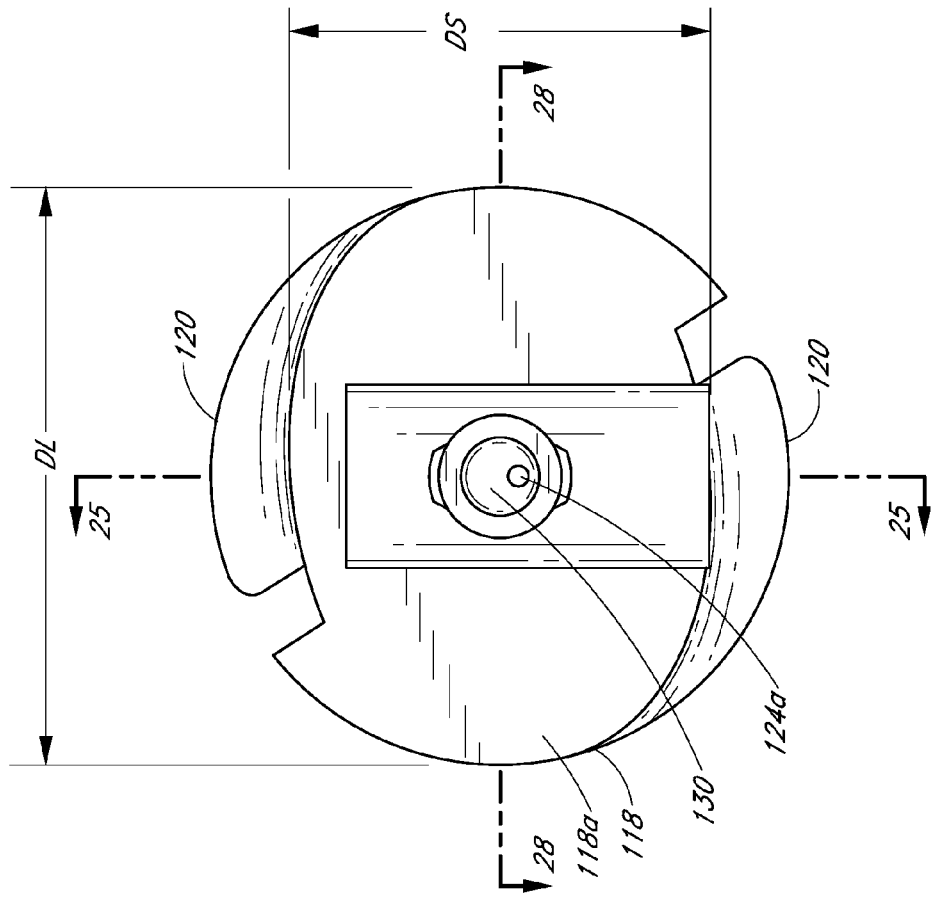
FIG. 23 is a top view of the embodiment of the vial adaptor shown in FIG. 21.

FIGS. 21-22 are perspective views of another embodiment of a vial adaptor 110. FIGS. 23-24 are top and bottom views, respectively, of the embodiment of the vial adaptor 110 shown in FIG. 21. FIG. 25 is a section view of the embodiment of the vial adaptor 110 shown in FIG. 21, taken through line 25-25 in FIG. 23. In some embodiments, the vial adaptor 110 can have any of the same features, shapes, sizes, proportional relationships, configurations, or other details of any other vial adaptor disclosed herein, including but not limited to the embodiments of the vial adaptor 10, 10', 10'', and 10''', and the embodiments of the vial adaptors incorporated herein by reference. Some components, features, or details of the vial adaptor 110 that are similar to those of any of the other vial adaptors disclosed herein may not be labeled or described in detail, such disclosure having been set forth elsewhere herein. Similar to the vial adaptor 10 described above, to increase or optimize the amount of the medicament that can be removed from a vial, the vial adaptor 110 can be configured such that the vial adaptor 110 is biased to affect the depth of the penetrating portion 114 into the vial.

With reference to FIGS. 21-25, the vial adaptor 110 can comprise a body portion 112, a penetrating portion 114, and an interface portion 116. In some embodiments, the vial adaptor 110 can be formed without a penetrating portion 114, and can be used to seal an open vial that has already been opened or for which the septum or seal has been damaged or removed. In the illustrated embodiment, the body portion 112 can comprise a central or base portion 118 and one or more tabs 120 (two opposing tabs 120 being shown). With reference to FIGS. 21-22, the central portion 118 can have a top portion 118a and flange portion 118b supported by the top portion 118a. In some embodiments, the flange portion 118b can be configured to obstruct or block liquid that inadvertently escapes from a vial when the vial adaptor 110 is secured thereto. The top portion 118a can be generally planar or curved, or can define any suitable shape. In some embodiments, as in the embodiment illustrated in FIGS. 21-22, the tabs 120 can be supported by the flange portion 118b of the central portion 118 so that the tabs 120 are not supported directly by the top portion 118a of the central portion 118.

As shown, for example in FIGS. 23-24, the central portion 118 can have a generally ovular or elliptical shape, having a first or long dimension (represented by "DL" in FIGS. 23-24) and a second or shorter dimension (represented by "DS" in FIGS. 23-24). The first dimension DL can be sized to accommodate the largest vial size that the vial adaptor 110 is desired to be used with. In some embodiments, the first length DL of the central portion 118 can be substantially greater than the second length DS of the central portion 118. In some embodiments, the first length DL of the central portion 118 can be approximately 133%, or between approximately 120% and approximately 135% or between approximately 135% and approximately 150% of the second length DS of the central portion 118 or from or to any valve within any of the ranges listed above. In some embodiments, first dimension DL is approximately equal to second dimension DS.

As mentioned, each of the tabs 120 can be supported at a proximal end of the tab 120 by the flange portion 118b of the central portion 118 of the body portion 112. As can be seen in the referenced Figures, each of the tabs 120 can define a generally curved or elliptical shape that, in the relaxed state of the tabs 120, can generally match the shape of the central portion 118. Furthermore, the distal end of each of the tabs 120 can each be unrestrained so as to allow each tab 120 to deflect outward in a radial direction (i.e., so that the unrestrained end portion of each tab 120 deflects away from the penetrating portion 114). In some embodiments, as in the illustrated embodiment, each of the tabs 120 can be deflected about an axis that is generally parallel with the centerline axis of the adaptor 110. Configuring the tabs 120 such that their axis of deflection extends generally parallel to the axis of the penetrating portion 114 can facilitate the insertion of the vial adaptor 110 into the vial.

In some embodiments, as illustrated most clearly in FIGS. 21-22, the vial adaptor 110 can be configured so that one or more slots 119, 121 are formed in the flange portion 118b of the central portion 118. In some embodiments, the slots 119, 121 can be formed so that the one or more tabs 120 can be deflected away from the flange portion 118b of the central portion 118 and/or the penetrating portion 114. For example, in some embodiments, a first slot 119 can be formed between each tab 120 and the flange portion 118b of the central portion 118. The first slot 119 can be oriented, for example, in a plane that is generally transverse to the axial centerline of the penetrating portion 114 or in a plane that forms a generally acute angle relative to the normal plane extending through axial centerline of the penetrating portion 114. Additionally, in some embodiments, a second slot 121 can be formed between each tab 120 and the flange portion 118b of the central portion 118. The second slot 120 can be oriented, for example, in a plane that is generally parallel to the axial centerline of the penetrating portion 114 or in a plane that forms a generally acute angle to the axial centerline of the penetrating portion 114.

In some embodiments, as illustrated most clearly in FIGS. 21-24, the flange portion 118b can define one or more surfaces that can be oriented so as to be generally parallel with the approximate axial centerline of the penetrating portion 114. In this configuration, the flange portion 118b can form a generally tube-like structure having an elliptical or ovular cross-section approximately centered about the centerline axis of the vial adapter 110. However, as will be described in greater detail below, because slots 119, 121 can be formed in the flange portion 118b and because the flange portion 118b can support the one or more tabs 120, the cross-section of the flange portion 118b in some embodiments can be discontinuous along at least a portion of the length of the flange portion 118b.

In some embodiments, the flange portion 118b can be configured to define any number of suitable cross-sectional shapes, including a generally circular, square, rectangular, or polygonal cross-sectional shape. In some embodiments, the flange portion 118b can be configured to define one or more generally tapered walls such that the angular orientation of at least a portion of the walls of the flange portion 118b (for example, without limitation, the portion of the walls of the flange portion 118b that support the tab or tabs 120) are not parallel with the axial centerline of the penetrating portion 114 of the vial adaptor 110. For example (not illustrated), in some embodiments, the flange portion 118b can be configured to define one or more walls that define an acute angle relative to the axial centerline of the penetrating portion 114.

In some embodiments the flange portion 118b can be configured to define one or more generally flat or curved projections or flanges that are supported by the top portion 118a of the central portion 118 in either a parallel or angled orientation relative to the centerline axis of the vial adaptor 110. In these configurations, similar to the configurations of the flange portion 118b described above, the one or more projections or flanges comprising the flange portion 118b can be configured to support the one or more tabs 120

In some embodiments, the flange portion 118b can be configured to define one or more walls that define an angle relative to the axial centerline of the penetrating portion 114 that is between approximately 0 degrees and approximately 15 degrees, or between approximately 15 degrees and approximately 30 degrees, or between approximately 30 degrees and approximately 45 degrees, or between any values within these ranges.

Because, in some embodiments, the flange portion 118b can have an angled surface relative to the axial centerline of the penetrating portion 114, the one or more tabs 120 can also be supported by the flange portion 118b at an angle relative to the axial centerline of the penetrating portion 114. For example and without limitation, in some embodiments (not illustrated), each of the tabs 120 can be supported by the flange portion 118b so that each of the tabs 120 can be deflected about an axis that forms an acute angle relative to the approximate axial centerline of the penetrating portion 114.

Therefore, in some embodiments, each of the tabs 120 can be deflected about an axis that forms an acute angle relative to the axial centerline axis of the penetrating portion 114 and/or the adaptor 110). For example, in some embodiments (not illustrated), each of the tabs 120 can be deflected about an axis that forms an angle relative to the axial centerline axis of the penetrating portion 114 and/or the adaptor 110 that is less than approximately 25 degrees, or from approximately 0 degrees (i.e., generally parallel to the axial centerline of the penetrating portion 114 and/or the vial adaptor 110) to approximately 15 degrees, or from approximately 15 degrees to approximately 30 degrees, or from approximately 30 degrees to approximately 45 degrees, or from or to any value within these ranges.

As with the other embodiments of the vial adaptors described above, the body portion 112, including the central portion 118 and tabs 120, can help removably secure the vial adaptor 110 to the outside surface of a vial. Additionally, the tabs 120 can help facilitate the removal of the vial adaptor 110 from the vial to which the adaptor 110 is connected, as will be discussed in greater detail below. In some embodiments, not shown, the body portion 112 can define only one tab 120, as opposed to a pair of opposing tabs 120, the single tab being configured to removably secure the vial adaptor 110 to the outside surface of a vial and to facilitate the removal of the vial adaptor 110 from the vial. The single tab 120 described above can be of any suitable configuration, including those set forth in this description. Similarly, as in the other embodiments disclosed herein, in some embodiments three or more tabs 120 may be incorporated.

In the illustrated embodiment, the penetrating portion 114 can be supported by the body portion 112. The penetrating portion 114 can project downward from the bottom of the central portion 118 of the body portion 112. The penetrating portion 114 can comprise a cannula with a cylindrical outer surface 114a, an end portion 114b that can be configured to penetrate through a septum or stopper, and one or more axial openings 124 therethrough. The end portion 114b can be pointed (as illustrated), can be rounded or dulled, or can comprise any suitable shape. In particular, in some embodiments, for example as illustrated in FIGS. 24 and 25, the penetrating portion 114 can have an opening 124a axially therethrough. The opening 124a can be configured to permit the contents of a vial to be extracted therethrough. The vial adaptor 110 can have only one, or can have any number of openings 124 therethrough.

In some embodiments, the penetrating portion 114 can also have another opening 124b axially therethrough, for example as illustrated in FIG. 25. Similar to opening 24b described above with respect to vial adaptor 10, the opening 124b of vial adaptor 110 can be configured to be in fluid communication with the transverse opening 136 formed in the body portion 112 of the vial adaptor 110 so as to provide a conduit through which air can pass to fill a vial and, hence, compensate for the displaced volume of the contents of the vial that can be removed through the vial adaptor 110. The opening 136 can be configured to support any of the filter members described herein, including but not limited the filter members 38, 38', or any other suitable filter so that contaminants are removed from the air filling the vial. In some embodiments, the cross-sectional area or diameter of the opening 124a can be greater than the cross-sectional area or diameter of the opening 124b.

Figure 26B:
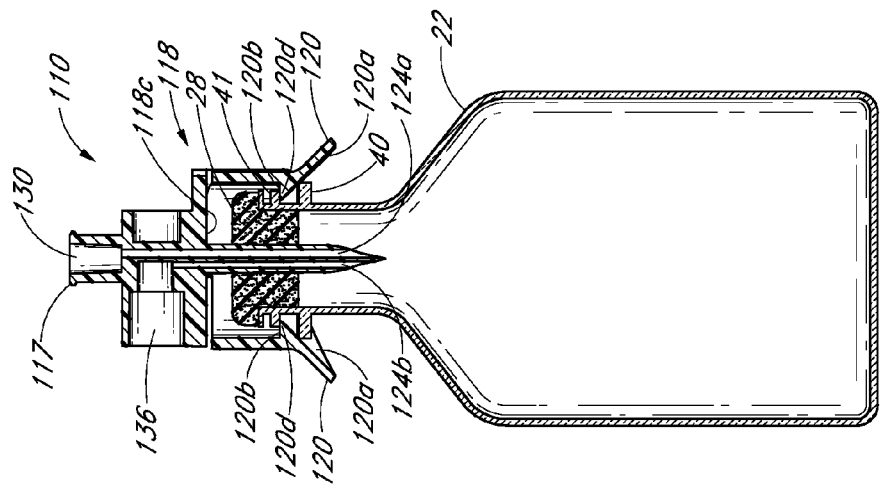
FIG. 26B is a section view of the embodiment of the vial adaptor of FIG. 21 inserted into a 20 mm vial, taken through the axial centerline of the embodiment of the vial adaptor.

The penetrating portion 114 can be inserted through a septum or stopper 28, or any other object that is typically used to seal the opening in a vial, by pushing the penetrating portion 114 of the vial adaptor 110 against the stopper of a vial until the penetrating portion 114 protrudes through the stopper, as is discussed above. In this arrangement, for example as illustrated in FIG. 26B, the openings 124a, 124b can be positioned inside the vial 22 below the bottom surface of the stopper 28 so as to be in communication with the inside volume of the vial. In some embodiments, as in the illustrated embodiment, the penetrating portion 114 can define a circular cross-section. However, the penetrating portion 114 can define an ovular, triangular, square, rectangular, or any other suitably shaped cross-section. A result of having a triangular, square, or other non-smoothly shaped cross-section is that the penetrating portion can engage with the cap 26 or stopper 28 of the vial to inhibit the vial adaptor 110 from twisting or rotating relative to the vial.

The frictional force of the seal from the stopper 28 around the outer surface 114a of the penetrating portion 114 can provide some axial support to the vial adaptor 110 so as to inhibit the axial movement of the vial adaptor 110 relative to the vial 22. In some embodiments, the outer surface 114a of the penetrating portion 114 can comprise features such as, but not limited to, ribs or striations that can be oriented perpendicular to the longitudinal axis of the penetrating portion 114, to increase the axial support provided by a stopper to the penetrating portion 114. As will be discussed in greater detail below, in some embodiments, the vial adaptor 110 can be configured to control the depth of the end portion 114b of the penetrating portion 114 relative to the bottom surface of a cap so as to increase or maximize the amount of fluid that can be withdrawn from a vial when the vial is in a cap down orientation, even when used with a certain range of different vial sizes.

In the illustrated embodiment, the interface portion 116 can be supported by the body portion 112. As illustrated in FIG. 21, the interface portion 116 can project upward from the upper surface 118a of the central portion 118 of the body portion 112. In some embodiments, the interface portion 116 can comprise a cylindrical outer surface and a third opening 130 axially disposed through at least a portion of the interface portion 116. In the illustrated embodiment, as shown for example in FIGS. 23 and 25, the opening 130 can be in fluid communication with the opening 124a such that the contents of a vial can pass from the opening 124a through the opening 130 when the adaptor 110 is engaged with the vial.

Any of a variety of suitable means for sealably closing the interface portion 116 of the vial adaptor 110 can be used to prevent the contents of a vial from flowing out of the vial when the vial adaptor 110 is inserted therein, as well as to seal the vial adaptor 10 and vial from contamination from bacteria, germs, or other contaminants. In some embodiments, the closing means or mechanisms can function to prevent and/or impede the contents of the vial from escaping from or entering into the vial, while allowing the contents of the vial to flow through the vial adaptor 110 when the closing means is opened or engaged with a corresponding male tipped connector or syringe or otherwise.

Similar to the interface portion 16 described above, the interface portion 116 can be configured to be connectable with any suitable medical connector or fluid flow connector, such as, without limitation, a male Luer connector. In some embodiments, the interface portion 116 can comprise a flange, protrusions (which can be opposing), or threads 117 to aid in coupling the vial adaptor 110 with the medical connector, a medical device, or other instrument. In some embodiments, the interface portion 116 can define a smooth cylindrical surface without such flange, protrusions, or threads. In some embodiments, the medical connector, a medical device, or other instrument can be secured to the interface portion 116 with adhesive or any other bonding or adhesive material. The interface portion 116 can be configured to accept any suitable medical connector, such as a syringe or sealable medical connector, or other connectors capable of sealing upon removal of a medical device therefrom. In some arrangements, the flange 117 can be sized and configured to accept the Clave® connector, available from ICU Medical, Inc. of San Clemente, Calif., described above. Connectors of many other varieties, including other needleless connectors, can also be used. Any such connectors can be removably attached to interface portion 116 or can be permanently bonded thereto.

Figure 26A:
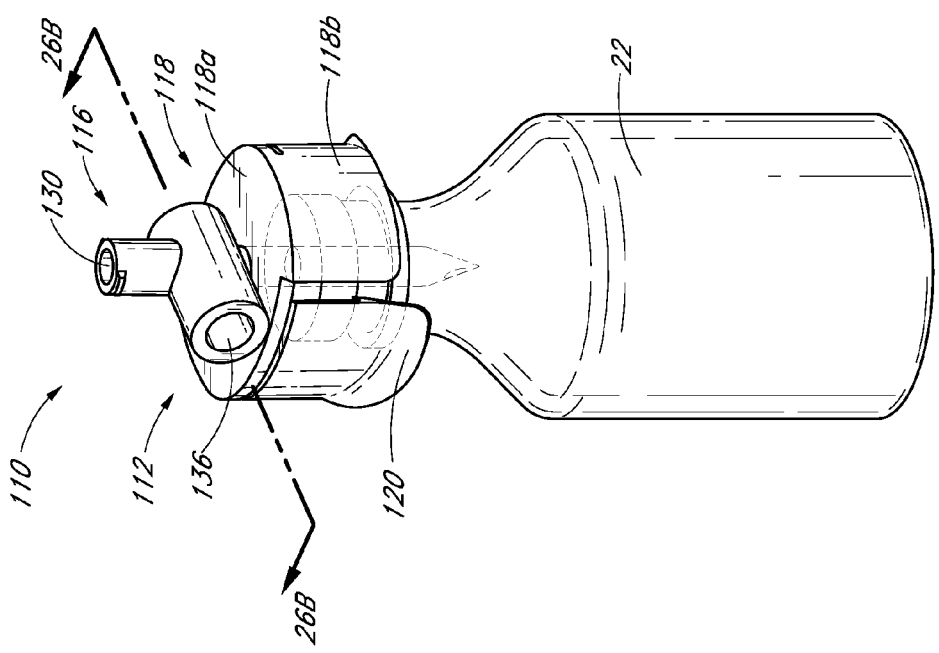
FIG. 26A is a perspective view of the embodiment of the vial adaptor of FIG. 21 inserted into a 20 mm vial.

FIG. 26A is a perspective view of the embodiment of the vial adaptor 110 attached to an exemplifying vial. FIG. 26B is a section view of the embodiment of the vial adaptor 110 attached to an exemplifying vial, taken through the axial centerline of the embodiment of the vial adaptor 110. The vial adaptor 110 can be inserted on or attached to a vial in a similar manner relative to any of the vial adaptors disclosed herein, including but not limited to any of vial adaptors 10, 10', and 10".

As mentioned above, the body portion 112 can comprise a pair of opposing tabs 120 attached to the central portion 118. In some embodiments, as illustrated in FIG. 25, the tabs 120 each can define an inside surface 120a, an abutment surface 120b, an end portion 120c, and a protruding portion 120d. As will be discussed below, the abutment surfaces 120b and protruding portions 120d can aid in securing the vial adaptor 110 to the vial 22. In some embodiments, as illustrated, the protruding portions 120d can define a generally linear shape. In some embodiments, however, the protruding portions 120d can define a generally arcuate shape, or have a v-shaped groove. Additionally, with reference to FIGS. 23-24, each of the tabs 120 can be curved so as to generally match the curvature of the perimeter of the upper surface 118a of the central portion 118 of the body portion 112.

In the illustrated embodiment, the end portion 120c of each tab 120 can taper outwardly away from the penetrating portion 114. In some embodiments, the end portion 120c of each tab 120 can taper outwardly at an angle that can be approximately 25° relative to a vertical plane, or from approximately 25° to approximately 35°, or from approximately 35° to approximately 50° relative to a vertical plane.

The vial adaptor 110 can be configured such that the vial adaptor 110 can be attached to a wide range of vials having a wide range of cap or stopper diameters. In particular, the central portion 118 and tabs 120 can be configured so as to be elastically bendable or deformable by a user to attach to or fit around a wide range of vial cap diameters. In some embodiments, the position, size, and shape of the protruding portions 120d on each of the tabs 120 and the other details regarding the design of the tabs 120 can be the same as is described above with regard to the vial adaptor 10. For example, the position, size, and shape of the protruding portions 120d on each of the tabs 120 and the other details regarding the design of the tabs 120 can be the same as is illustrated in and described in conjunction with FIGS. 6-7. However, the vial adaptor 110 and any components or features thereof is not limited to the specific ranges or configurations described above. The vial adaptor 110 can be of any size or configuration that is suitable for the vial or vials for which the vial or vial adaptor 110 is intended to be used.

As will be described in greater detail below, the vial adaptor 110 can be inserted into a vial by positioning the vial adaptor 110 above the top of the stopper of the vial so that the axial center of the penetrating portion 114 is approximately aligned with the axial center of the rubber septum or stopper. By grasping the vial adaptor 110 and pushing the vial adaptor 110 downwardly against the stopper, the penetrating portion 114 can be introduced into the stopper 28. As force is continued to be applied to the vial adaptor 110, the stopper of the vial can eventually contact the inside surface 120a of the tabs 120. Further axial force can cause the deflectable tabs 120 to spread apart (e.g., in opposing directions as shown by arrows A3 and A4 in FIG. 24) so that the penetrating portion 114 of the vial adaptor 110 can be further inserted into the vial. For example, in some embodiments, the tabs 120 can be configured so that a user can easily spread the tabs 120 apart by grasping or otherwise exerting a force on the inside surface of the end portions 120c of the tabs 120 and deflecting the tabs 120 away from the vial.

The vial adaptor 110 can be inserted into the vial such that the end portion 114b of the penetrating portion 114 protrudes through the stopper 28 to a sufficient distance so that the one or more openings 124 in the penetrating portion 114 can be in communication with the inside volume of the vial 22. In this configuration, the contents of the vial 22 can be extracted through the opening or openings 124. As mentioned, the vial adaptor 110 can be configured to control the depth of penetration of the penetrating portion 114 into the vial for a multitude of the vial sizes so as to increase or maximize the amount of medicament or other substance that can be extracted from the vial through the vial adaptor 110.

In some embodiments, the thickness of the material forming each tab 120 can be significantly less than the diameter or size of the cross-section of the penetrating portion 114. For example, in some embodiments, the thickness of the material forming each tab 120 can be less than approximately ½ than approximately ¼ of the diameter or size of the cross-section of the penetrating portion 114. In some embodiments, the thickness of the material forming each tab 120 can be approximately 40% of the diameter or size of the cross-section of the penetrating portion 114, or from approximately 25% to approximately 40%, or from approximately 40% to approximately 55%, or from approximately 55% to approximately 70% of the diameter or size of the cross-section of the penetrating portion 114, or from or to any value in these ranges.

In some embodiments, the thickness of the material forming each tab 120 can be approximately 1.5 mm. In some embodiments, the thickness of the material forming each tab 120 can be from approximately 1 mm to approximately 1.5 mm, or from approximately 1.5 mm to approximately 2 mm, or from approximately 2 mm to approximately 2.5 mm or from or to any value in these ranges.

However, the size and configuration of each tab 120 is not limited to any of the specific sizes, ranges, or configurations described above. Each tab 120 can have any length, taper angle, thickness, width, size or configuration that is suitable for the vial or vials for which the vial adaptor 110 is intended to be used, or for the material that is chosen for each tab 120 or for any other components or features of the vial adaptor 110. In some embodiments, each tab 120 can define a different size, shape, or other configuration as compared to any other tab 120 formed on the vial adaptor.

In some embodiments, the thickness of the material forming the central portion 118 can be significantly less than the diameter or size of the cross-section of the penetrating portion 114. For example, in some embodiments, the thickness of the material forming the central portion 118 can be less than approximately half than approximately three-quarters of the diameter or size of the cross-section of the penetrating portion 114. In some embodiments, the thickness of the material forming the central portion 118 can be approximately 40% of the diameter or size of the cross-section of the penetrating portion 114, or from approximately 25% to approximately 40%, or from approximately 40% to approximately 55%, or from approximately 55% to approximately 70% of the diameter or size of the cross-section of the penetrating portion 114, or from or to any value in these ranges.

In some embodiments, the thickness of the material forming the central portion 118 can be approximately 1.5 mm. In some embodiments, the thickness of the material forming the central portion 118 can be from approximately 1 mm to approximately 1.5 mm, or from approximately 1.5 mm to approximately 2 mm, or from approximately 2 mm to approximately 2.5 mm or from or to any value in these ranges.

However, the size and configuration of the central portion 118 is not limited to the specific ranges or configurations described above. The central portion 118 can be of any size or configuration that is suitable for the vial or vials for which the vial adaptor 110 is intended to be used, or for the material that is chosen for the central portion 118 or for any other components or features of the vial adaptor 110. In some embodiments, the width and thickness, or other aspects of the size and configuration of the central portion 118, can be the same as, or different than, that of the tabs 120 formed on the vial adaptor 110.

As mentioned, in some embodiments, the tabs 120 can each be sized and configured such that a portion of the inside surface 120a can slidingly receive the outer, generally cylindrical surface of a stopper when the vial adaptor 110 is inserted into a vial. As illustrated, for example in FIG. 26B, the abutment surfaces 120b can each be configured to inhibit the vial adaptor 110 from moving axially away from the vial 22 when the vial adaptor 110 is inserted into the vial 22 to a sufficient distance such that the abutment surfaces 120b overlap an adjacent protruding surface or surfaces on the vial 22 or stopper 28.

As mentioned, the vial adaptor 110 can be configured such that, when the vial adaptor 110 is attached to a vial, the tabs 120 can be deflected and spread apart (either by the user grasping and deflecting the end portions 120c of the tabs 120 or from the contact between the vial and the inside surface 120a of the tabs 120) so as to accommodate a vial having a cap or stopper diameter that is larger than the distance between the opposing protruding portions 120d. In some embodiments, the vial adaptor 110 can be sized and configured such that, when the tabs 120 are spread apart, the distance between one or more of the protruding portions 120d is significantly greater than the distance between the protruding portions 120d when the vial adaptor 110 is in the relaxed state.

For example, in some embodiments, the vial adaptor 110 can be sized and configured such that the distance between the protruding portions 120d when the tabs 120 are fully spread apart (i.e., when the vial adaptor 110 is mounted to a vial) can be at least approximately 50% larger than the distance between the protruding portions 120d when the tabs 120 are in the relaxed state. In some embodiments, the vial adaptor 110 can be sized and configured such that the distance between the protruding portions 120d when the tabs 120 are spread apart or when the vial adaptor 110 is mounted to a vial is from approximately 120% to approximately 130%, or from approximately 130% to approximately 140%, or from approximately 140% to approximately 150% or to or from any value within these ranges, of the distance between the protruding portions 120d when the tabs 120 are in the relaxed state.

In some embodiments, the vial adaptor 110 can be sized and configured such that, when the tabs 120 are spread apart, the distance between the protruding portions 120d can be from approximately 16 mm to approximately 20 mm, or from approximately 20 mm to approximately 24 mm, or from approximately 24 mm to approximately 28 mm, or from approximately 28 mm to approximately 32 mm or from or to any value in these ranges. However, the vial adaptor 110 and any components or features thereof is not limited to the specific ranges or configurations described above. The vial adaptor 110 can be of any size or configuration that is suitable for the vial or vials for which the vial adaptor 110 is intended to be attached.

In some embodiments, where the vial adaptor 110 has two or more tabs 120 as illustrated in FIGS. 24 and 25, the vial adaptor 110 can be configured such that at least a portion of the protruding portion 120d of one of the tabs 120 can be closer to the penetrating portion 114 than a portion of the protruding portion 120d of one or more of the other tabs 120. For some embodiments, this can depend in part on the location and orientation of the cross-sectional plane that is chosen. For example, with reference to FIG. 25, the portion of the penetrating portion 120d of the rightmost tab 120 that is shown in the cross-sectional plane can be closer to the penetrating portion 114 than the portion of the penetrating portion 120d of the leftmost tab 120 that is shown in the cross-sectional plane. In some embodiments, however, the vial adaptor 110 can be formed such that each portion of the protruding portion 120d of each tab can be approximately equidistant from the penetrating portion 114 over a range of deflections of the tabs 120 as compared to the protruding portions 120d of the other tabs 120.

For some vials, as illustrated in FIG. 26B, the positioning of the protruding portions 120d relative to the inside surface 118c of the body portion 118 or relative to the openings 124 can be used to control the depth of penetration of the penetrating portion 114 into the vial and, hence, the opening 124a, relative to the stopper. The position of the protruding portions 120d relative to the inside surface 118c of the body portion 118 can be varied from one vial adaptor 110 to the next to enable the penetrating portion of each vial adaptor 110 to penetrate to a different distance as compared to the next.

In some embodiments, in the pre-stressed state, the vial adaptor 110 can be sized and configured such that the distance between the protruding portions 120d and the inside surface 18c of the body portion 118 can be significantly less than the length of the penetrating portion 114. For example, in some embodiments, in the pre-stressed state, the distance between the protruding portions 120d and the inside surface 118c of the body portion 118 can be less than approximately three-quarters, than approximately half of the length of the penetrating portion 114. In some embodiments, the distance between the protruding portions 120d and the inside surface 118c of the body portion 118 can be from approximately 40% to approximately 50%, or from approximately 50% to approximately 60%, or from approximately 60% to approximately 70% of the length of the penetrating portion 114.

In some embodiments, in the pre-stressed state, the vial adaptor 110 can be sized and configured such that the distance between the protruding portions 120d and the inside surface 118c of the body portion 118 is from approximately 7 mm to approximately 10 mm, or from approximately 10 mm to approximately 13 mm, or from approximately 13 mm to approximately 16 mm or to or from any value in these ranges. However, the vial adaptor 110 and any components or features thereof is not limited to the specific ranges or configurations described above. The vial adaptor 110 can be of any size or configuration that is suitable for the vial or vials for which the vial or vial adaptor 110 is intended to be used.

In some embodiments, in the pre-stressed state, the vial adaptor 110 can be sized and configured such that the distance between the protruding portions 120d and the top of the opening 124a or opening 124b is approximately 60% of the length of the penetrating portion 114, or from approximately 40% to approximately 50%, or from approximately 50% to approximately 60%, or from approximately 60% to approximately 70% of the length of the penetrating portion 114. In some embodiments, in the pre-stressed state, the vial adaptor 110 can be sized and configured such that the distance between the protruding portions 120d and the top of the opening 124a or opening 124b is approximately 2 mm, or from approximately 2 mm to approximately 4 mm, or from approximately 4 mm to approximately 6 mm or from or to any value in these ranges.

To facilitate removal of the vial adaptor 110 from a vial, the end portion 120c of each tab 120 can be configured to have an outward flare or other structure to permit the user to easily grasp and deflect each of the tabs 120 radially outward so as to deflect away from the vial and, consequently, deflect each of the protruding portions 120d radially outward away from the vial so that the abutment surfaces 120b no longer overlap the protruding surface or surfaces on the vial 22, stopper 28, or cap. The end portions 120c can be configured so that a user gripping or contacting the end portions 120c of the tabs 120 with one hand and holding the vial 22 with the other can exert an axial, upward force on the vial adaptor 110 relative to the vial 22 so as to remove the vial adaptor 110 from the vial 22.

Additionally, in some embodiments, the end portion 120c of each tab 120 can comprise channels, scores, protrusions, pits, a gnurled texture, soft rubber, or any other features, materials, or textures to prevent a user's fingers or hands from slipping relative to the surface of the end portion 120c of each tab 120. Additionally, in some embodiments, the distal end portions of the end portions 120c can be configured to define an outwardly curved or flared surface to better enable a user to access or grasp the inside surface 120a of the tabs 120. In other words, the curved or flared surface of the end portions 120c of the tabs 120 better enable the user to slide his or her finger or fingers underneath the tabs 120 so as to exert a radially outward pressure on the tabs 120 to spread the tabs radially outward. Therefore, when a user desires to remove the vial adaptor 110 from a vial, the abutment surfaces 120b can be disengaged from the protruding vial surfaces, stopper, or cap by spreading the tabs 120 away from one another until the abutment surfaces 120b no longer overlap protruding vial surfaces, stopper, or cap. The vial adaptor 110 can then be removed by exerting an axial force on the vial adaptor 110 away from the vial. Additionally, in some embodiments, as in the illustrated embodiments, the end of each end portion 120c can be rounded or curved. This can be done to eliminate or soften otherwise sharp corners.

In some embodiments, the central portion 118 and tabs 120 can be configured to elastically deform or deflect so that the protruding portions 120d deflect outwardly over a wide range of distances to enable the vial adaptor 110 to accommodate a wide range of vial sizes. For this purpose, in some embodiments, the central portion 118 and tabs 120 can be shaped and configured and made from a material that permits a significant amount of the elastic deflection while still allowing the tabs 120 and protruding portions 120d to exert a radial inward force sufficient to adequately secure the vial adaptor 110 to the vial. In particular, in some embodiments, the body portion 112 can define a constricted portion such as, but not limited to, the distance between protruding portions 120d that is narrower than the diameter of the cap or neck on the vial into which the vial adaptor 110 is to be inserted, so that the tabs 120 deflect outward as the penetrating portion 114 is being inserted into and through the stopper 28. Consequently, the deflected tabs 120 can each exert a radial force directed toward the axial center of the vial adaptor 110 that is commensurate with the magnitude of their deflection so that the tabs 120 exert a reactive force on the vial and/or vial cap when the vial adaptor 110 is attached to the vial.

As mentioned, the vial adaptor 110 can be configured to work with a wide range of vial sized such as, but not limited to, vials having 8 mm, 11 mm, 13 mm, 17 mm, 20 mm, and 28 mm opening sizes, among others. The tabs 120 can be formed from a resilient material that permits the tabs 120 to deflect outwardly to accommodate at least the range of vial sizes listed above.

In some embodiments, the tabs 120 can be integrally formed with the central portion 118. In some embodiments, the tabs 120 can be formed separately and fused, welded, or otherwise attached to the central portion 118 with adhesive or other suitable fastening substances or materials, such as, without limitation, screws, rivets, or pins.

In some embodiments, as illustrated for example in FIGS. 22 and 24, the central portion 118 can have one or more protrusions 134. For some vials, each of the protrusions 134 can help secure the vial adaptor 110 in approximate alignment with the axial centerline of the vial to which the vial adaptor 110 is attached. For example, the protrusions 134 can be configured to contact a portion of the typically cylindrical outside surface of a vial or the typically cylindrical outside surface of a stopper or cap. In some embodiments, the protrusions 134 can be curved (as illustrated). In some embodiments (not shown), the protrusions 134 can define two generally planar surfaces defining a "V" shaped groove, which can be configured to contact a portion of the cylindrical outside surface of a vial or the generally cylindrical outside surface of a stopper or cap so as to bias the vial adaptor 110 to remain approximately aligned with the axial centerline of the vial.

In embodiments where the protrusions 134 are curved and where the penetrating portion 114 defines a circular cross-section, the radius of curvature of the protrusions 134 can be significantly greater than the radius of the cross-section of the penetrating portion 114. In some embodiments, the axial centerline of the protrusions 134 can be collinear with the centerline axis of the penetrating portion 114. In some embodiments, the radius of curvature of the protrusions 134 can be approximately 2 cm. In some embodiments, the radius of curvature of the central portion 118 can be from approximately 1 cm to approximately 2 cm, or from approximately 2 cm to approximately 3 cm, or from approximately 3 cm to approximately 4 cm or to or from any value within these ranges.

As mentioned above, the penetrating portion 114 can comprise a cylindrical outer surface 114a and one or more axial openings 124 therethrough. The opening 124a (which is sometimes referred to herein as the first opening) can pass through the entire penetrating portion 114, body portion 112, and interface portion 116, where it can be joined so as to be in communication with the opening 130. Thus, the opening 124a can provide a conduit through which the contents of a vial can be extracted when the vial adaptor 110 is attached to the vial. The opening 124b (which is sometimes referred to herein as the second opening) can be in fluid communication with the transverse opening 136 to provide a conduit through which air can pass to fill the vial and, hence, compensate for the displaced volume of the contents of the vial that can be removed through the opening 124a. However, some embodiments of the vial adaptor 110 can be formed without a second opening (e.g., the opening 124b) or separate air vent. In these embodiments, the vial adaptor 110 can have only one opening (e.g., opening 124a) through which, at a minimum, fluid or medicament can be extracted from the vial.

Figure 27:
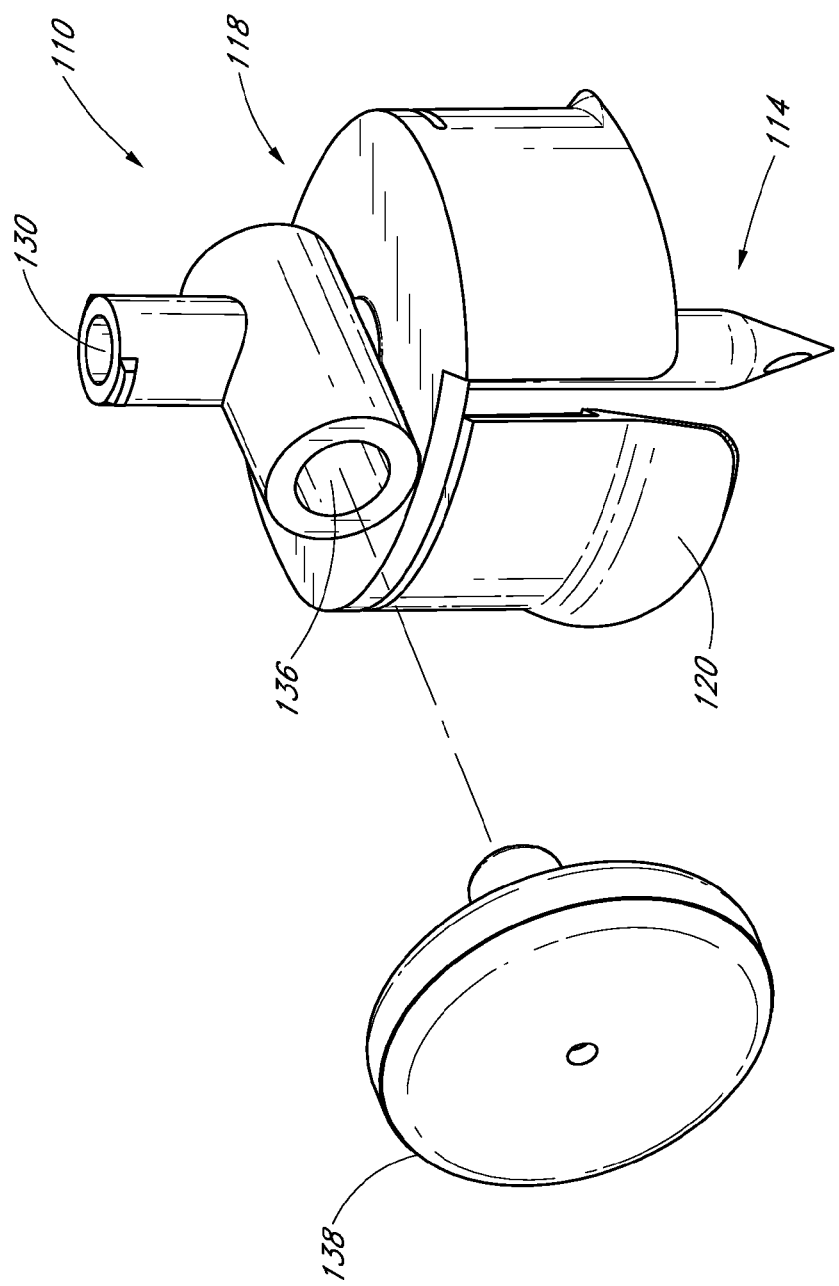
FIG. 27 is an exploded perspective view of the embodiment of the vial adaptor shown in FIG. 21 having an embodiment of a filter member.

FIG. 27 is an exploded perspective view of the vial adaptor 110 having a filter member 138. The filter member 138 can be configured to prevent debris from contaminating the inside of the vial. In some embodiments, the filter member 138 can also be configured to prevent any bacteria, germs, viruses, or other contaminants from entering the inside of the vial. The filter member 138 can be the same as or similar to the filter member 38' described above. Alternatively, in some embodiments (not illustrated), the vial adaptor 110 can have a filter member assembled therewith that is the same as or similar to the filter member 38 described above. In the illustrated embodiment, the filter member 138 can be positioned inside of, or adjacent to, the transverse opening 36 and can be held in place with adhesive or by any other suitable attachment means.

In some embodiments (not illustrated), the vial adaptor 110 can comprise a one-way valve configured to prevent the contents of the vial from leaking through the transverse opening 136, but to allow air to pass into the vial. The one-way valve can be formed separate from the filter member 138 or can be formed integrally with the filter member 138.

As described above, the position of the abutment surfaces 120b relative to the inside surface 118c of the body portion 118 can be varied from one vial adaptor 110 to the next. Further, the position of the opening 124a relative to the inside surface 118c can be varied from one vial adaptor 110 to the next. Accordingly, the position of the abutment surfaces 120b relative to position of the opening 124a can be varied from one vial adaptor 110 to the next.

In some embodiments, as in the illustrated embodiment, the end portions of each of the openings 124a, 124b can be approximately aligned. In some embodiments, the penetrating portion 114 can be configured such that the opening 124a terminates (i.e., passes through the wall of the penetrating portion 114) at an axial position on the penetrating portion 114 that is different than the point of termination of the opening 124b. In some embodiments, the penetrating portion 114 can be configured such that the opening 124a terminates at an axial position on the penetrating portion 114 that is closer to the inside surface 118a than the point of termination of the opening 124b. This configuration can allow air to pass through the end portion of the opening 124b at a point that is far enough removed from the opening 124a such that the air is not inadvertently drawn through the opening 124a as the contents of the vial are being extracted through the opening 124a. This configuration thus can prevent air bubbles from inadvertently entering the opening 124a when the vial is upside down and the contents of the vial are being extracted.

As mentioned, in some embodiments, the vial adaptor 110 can be sized and configured such that the end portion of the opening 124a is spaced apart from the end portion of the opening 124b. For example, in some embodiments, the vial adaptor 110 can be sized and configured such that the distance between the end portion of the opening 124a and the end portion of the opening 124b is from less than approximately half of the diameter or size of the cross-section of the penetrating portion. The distance between the end of the portion of the opening 124a and the end portion of the opening 124b can be approximately 50% to approximately 65%, or from approximately 65% to approximately 80%, or from approximately 80% to approximately 95% of the diameter or size of the cross-section of the penetrating portion 114.

In some embodiments, the vial adaptor 110 can be sized and configured such that the end portion of the opening 124a can be approximately 1 mm away from the end portion of the opening 124b, or from approximately 1 mm to approximately 3 mm, or from approximately 3 mm to approximately 5 mm, or from approximately 5 mm to approximately 7 mm away from the end portion of the opening 124b. However, the vial adaptor 110 and any components or features thereof is not limited to the specific ranges or configurations described above. The vial adaptor 10 can be of any size or configuration that is suitable for the vial or vials for which the vial adaptor 110 is intended to be used.

As illustrated, for example in FIG. 26B, as the vial adaptor 110 is being inserted into the vial, the protruding portions 120d can be biased to move into the space between the protruding lip portion 40 and the adjacent protruding lip portion 41. In some embodiments, as the vial adaptor 110 is being inserted into a vial, the protruding portions 120d can be biased to move into the space between a protruding lip portion and an adjacent planar surface of a stopper or cap, or other object attached to the vial. This can occur because the tabs 120 can be biased to exert a radial inward force against the vial, cap, and/or stopper when the vial adaptor 110 is being attached to the vial. In other words, the tabs 120 can each contract inwardly toward their pre-stressed or pre-installed state such that the protruding portion 120d of each tab 120 moves into the necked or recessed portion of the vial between the protruding lip portions 40 and 41, or between the protruding lip portion of the vial and the cap or stopper.

In this configuration, for some vials, the abutment surfaces 120b can control the depth of the penetrating portion 114 into the vial and can prevent the vial adaptor 110 from being inadvertently removed from the vial when the vial adaptor 110 is inserted into a vial. In some embodiments, this can be achieved when the vial adaptor 10 overlaps and abuts a protruding surface or surfaces on the vial, cap, or stopper, as illustrated in FIG. 26B.

Because fluid is typically withdrawn from the vial when the vial is in an upside down orientation, more fluid can generally be extracted through a vial adaptor 110 having a smaller distance between the interior fluid barrier surface of the stopper and the distal end of the opening 124a as compared to a vial adaptor 110 having a larger distance between the interior fluid barrier surface of the stopper and the distal end of the opening 124a. Thus, to increase or optimize the amount of medicament or other substance that can be extracted from the vial, the vial adaptor 110 can be configured so as to minimize the distance between the interior fluid barrier surface of the stopper and the distal end of the opening 124a. In some embodiments, the vial adaptor 110 can be configured so that the distance from the fluid barrier surface to the opening 124a is approximately the same when the vial adaptor 110 is attached to a wide range of vial sizes and configurations.

Figure 28A:
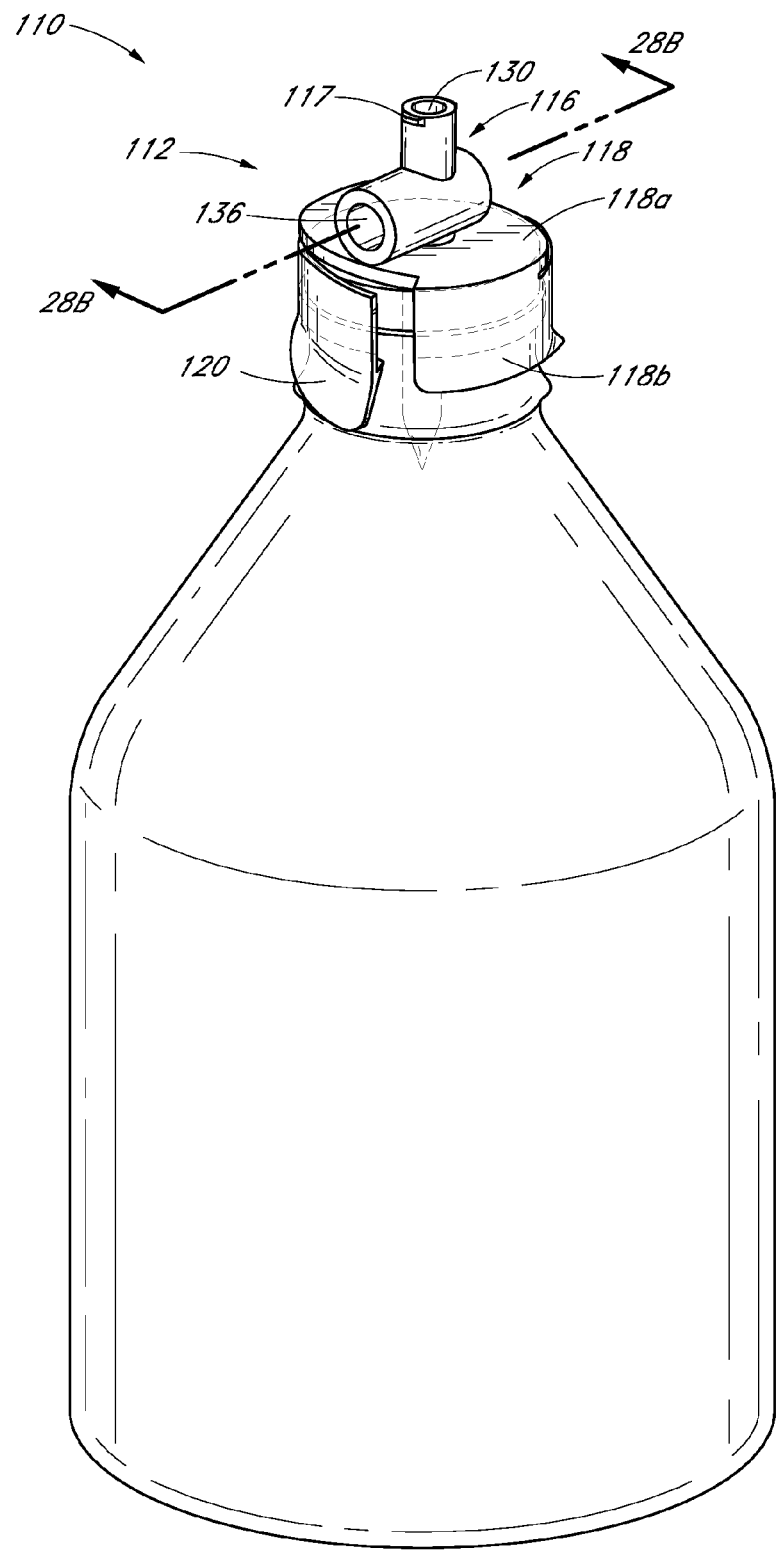
FIG. 28A is a perspective view of the embodiment of the vial adaptor of FIG. 21 inserted into a 28 mm vial.
Figure 28B:
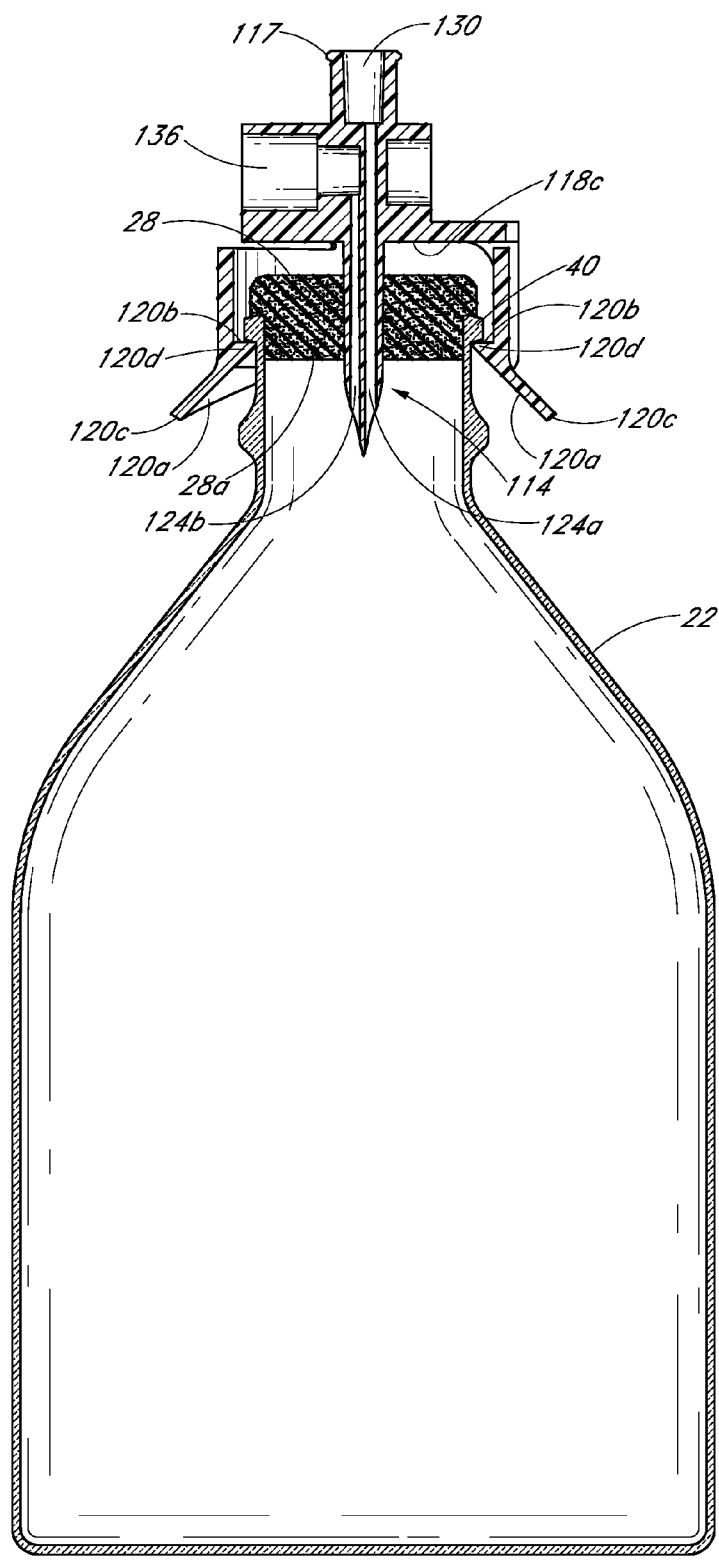
FIG. 28B is a section view of the embodiment of the vial adaptor of FIG. 21 inserted into a 28 mm vial, taken along the line 28B-28B in FIG. 28A.

In some embodiments, the vial adaptor 110 can be inserted into a 28 mm vial 22 as shown in FIG. 28A, which is a perspective view of the vial adaptor 110 inserted into a 28 mm vial 22. FIG. 28B is a section view of the vial adaptor 110 inserted into a 28 mm vial 22, taken along the line 28B-28B in FIG. 28A. As illustrated, for example in FIG. 28B, the penetrating portion 114 of the vial adaptor 110 can be inserted through a cap (not shown) and/or stopper 28 on the 28 mm vial 22 so that the opening 124a is below the inside planar surface 28a and, hence, inside the vial 22.

In some embodiments, the vial adaptor 110 can be configured to limit the depth to which the engagement portion 114 of the vial adaptor 110 can penetrate through the stopper 28 of the 28 mm vial. In particular, the vial adaptor 110 can be configured such that, when the vial adaptor 110 is inserted into the vial, the penetrating portion 114 protrudes through the stopper 28 to a distance that optimizes the amount of the contents that can be removed from the vial 22. In some embodiments, the protruding portions 120d can be sized and configured to control the depth of the penetrating portion 114 into the vial 22 by, as described above, interacting with protrusions on the vial that bias or secure the vial adaptor 110 in the desired axial location. Additionally, in some embodiments (not illustrated), the vial adaptor 110 can have one or more spacers (such as, but not limited to the spacers 42 shown in FIGS. 15A-15B) positioned between the central portion 118 and the vial cap 28 to control the depth of penetration of the penetrating portion 114. In some embodiments (not illustrated), the vial adaptor 110 can be inserted into the vial 22 until the inside surface 118c of the central portion 118 contacts the top of the cap, stopper 28, or vial 22, whichever component surface is first contacted, to thus control the depth of penetration of the penetrating portion 114.

As illustrated in FIGS. 28A-28B, in some embodiments, when the vial adaptor 110 is inserted into the vial 22, the tabs 120 can constrict around the cap, stopper 28, or protruding lip portions of the vial 22 such as protruding lip portion 40 of the vial 22 illustrated in FIGS. 28A-28B. This can cause the abutment surfaces 120b to overlap with the bottom surface of the cap, stopper 28, or protruding lip portions 40 of the vial, thus removably securing the vial adaptor 110 to the vial 22. When the user desires to remove the vial adaptor 110, the abutment surfaces 120b can be disengaged from the cap, stopper 28, or protruding lip portion 40 of the vial by spreading the tabs 120 away from one another until the abutment surfaces 120b no longer overlap the cap 28 or protruding lip portions 40. The vial adaptor 110 can then be removed by exerting an axial force on the vial adaptor 110 away from the vial 22.

The body portion 112, penetrating portion 114, and interface portion 116, or any other component or components of the vial adaptors described herein can be made from any suitable material such as, but not limited to, polycarbonate or other suitable polymeric or plastic materials. In some embodiments, one or more components of the vial adaptors described herein can be made from a hydrophobic material, such as Bayer Makrolon. The material chosen to make one or more of these components can be substantially fluid impervious and can be suitable for use with a wide range of medicaments.

In some embodiments, the body portion 112, penetrating portion 114, and interface portion 116 can be integrally formed in the same manufacturing step, such as in a plastic injection molding operation. In some embodiments, the body portion 112, penetrating portion 114, and interface portion 116 can be formed in separate manufacturing steps and fused, bonded, or otherwise attached together by any suitable method or with any suitable adhesive material. The filter member 38 can be attached to the vial adaptor 110 in a separate manufacturing step. The openings 124a, 124b can be formed in the vial adaptor 110 at the same time the body portion 112, penetrating portion 114, and interface portion 116 are formed, or can be formed in a subsequent step or process. The body portion 112, penetrating portion 114, and interface portion 116 can be made from a plastic, composite material, or other elastically deformable, semi-rigid material that is suitable for use in the medical field.

Additionally, any vial adaptor disclosed herein, including but not limited to the vial adaptors 10, 110, can comprise any of the features, materials, sizes, geometries, or other configurations or details described in U.S. Application Publication No. US 2007/0244456 A1 (application Ser. No. 11/414,948), titled "VIAL ADAPTOR FOR REGULATING PRESSURE" and filed on May 1, 2006, the entirety of which is hereby incorporated by reference as if fully disclosed herein.

Although this invention has been disclosed in the context of a certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above.

What is claimed is:

1. A vial adaptor configured to be attachable to a vial having an opening and a seal wherein the seal defines a fluid barrier surface, the vial adaptor comprising:
   a body portion;
   a penetrating portion supported by the body portion, the penetrating portion projecting from a first surface of the body portion and comprising an outer surface and a distal end portion, the penetrating portion being configured to be inserted through the seal past the fluid barrier surface so as to be positioned within an interior space of the vial;
   an interface portion supported by the body portion, the interface portion projecting away from a second surface of the body portion;
   at least one deflectable tab comprising a proximal end, a distal end, and a protruding portion, the proximal end being supported by the body portion;
   a first opening disposed axially through at least a portion of the penetrating portion; and
   a second opening disposed axially through at least a portion of the penetrating portion;
   wherein:
      the second opening comprises a first end portion and a second end portion and is configured such that the first end portion is in communication with a transverse opening and the second end portion passes through the outer surface of the penetrating portion; and
      wherein the body portion comprises a biasing member configured to bias the vial against the at least one deflectable tab and away from the first surface of the body portion to hold the second end portion of the second opening within the interior space of the vial proximate to the fluid barrier surface of the vial seal in a position which facilitates the removal of a majority of fluid from the vial.

2. The vial adaptor of claim 1, wherein the interface portion is configured to be connectable to a medical connector, syringe, or other medical implement.

3. The vial adaptor of claim 2, further comprising a third opening, the third opening comprises a first end portion and a second end portion and is configured such that the first end portion of the third opening is in communication with an interior space of the medical connector, syringe, or other medical implement, and the second end portion of the third opening is in communication with the first opening.

4. The vial adaptor of claim 1, wherein the interface portion is selectively sealable.

5. The vial adaptor of claim 1, wherein the first opening comprises a first end portion and a second end portion, the second end portion of the first opening is located adjacent to or at the distal end portion of the penetrating portion.

6. The vial adaptor of claim 5, wherein the second end portion of the second opening is located below the second end portion of the first opening so as to be closer to the distal end portion of the penetrating portion.

7. The vial adaptor of claim 1, wherein the at least one deflectable tab is configured such that the protruding portion exerts a pressure in a radial direction on an exterior surface of the vial or cap.

8. The vial adaptor of claim 1, wherein the transverse opening comprises a first end portion and a second end portion and being configured such that the first end portion of the transverse opening is in communication with ambient air and the second end portion of the transverse opening is in communication with the second opening and is configured to allow ambient air to flow into the interior space of the vial when the vial adaptor is engaged with the vial.

9. The vial adaptor of claim 1, further comprising a filter in communication with the transverse opening, the filter being configured to inhibit any contaminants from entering the transverse opening.

10. The vial adaptor of claim 9, wherein the filter comprises a filter membrane that has a cross-sectional area that is larger than a cross-sectional area of the transverse opening.

11. The vial adaptor of claim 1, wherein the vial adaptor can be used with any vial having an opening size between approximately 8 mm and approximately 28 mm in diameter.

12. The vial adaptor of claim 1, wherein the vial adaptor can be used with any vial having an opening size between approximately 13 mm and approximately 28 mm in diameter.

13. The vial adaptor of claim 1, wherein the at least one deflectable tab comprises at least a first tab and a second tab, the first and second tabs are spaced apart from and on opposite sides of the penetrating portion.

14. The vial adaptor of claim 1, wherein the at least one deflectable tab is configured to contact an outer surface of the vial and to approximately align the penetrating portion with the centerline axis of the vial as the vial adaptor is being inserted into the vial.

15. The vial adaptor of claim 1, wherein the body portion comprises an elastically deformable material.

16. The vial adaptor of claim 1, wherein the at least one deflectable tab comprises an abutment surface extending toward the penetrating portion.

17. The vial adaptor of claim 1, further comprising a filter member in communication with the transverse opening, the filter member having a peripheral diameter and comprising a first section and a second section with a membrane therebetween, the second section comprising an aperture in communication with ambient air, the aperture having a diameter that is substantially smaller than the peripheral diameter of the filter member.

18. The vial adaptor of claim 17, wherein the first and second sections each further comprise one or more protrusions.

19. The vial adaptor of claim 18, wherein each of the one or more protrusions further comprises a plurality of gaps.

20. The vial adaptor of claim 19, wherein the air is allowed to pass through the aperture of the second section and through the plurality of gaps of each of the one or more protrusions.

21. The vial adaptor of claim 18, wherein each of the one or more protrusions is annular.

22. The vial adaptor of claim 17, wherein the first and second sections are coupled together.

23. The vial adaptor of claim 17, wherein the membrane has a diameter that is substantially larger than a diameter of the transverse opening.

24. The vial adaptor of claim 17, wherein the membrane further comprises a first side and a second side, and the air is allowed to contact substantially the entire first side and substantially the entire second side.

25. The vial adaptor of claim 17, wherein the membrane comprises a hydrophobic material.

26. The vial adaptor of claim 17, wherein the filter member is received by the transverse opening in substantially airtight engagement.

27. The vial adaptor of claim 1, wherein the biasing member is a resilient spacer, the spacer being separately formed from the body portion.

28. The vial adaptor of claim 1, wherein the biasing member comprises a curved surface of the body portion.

* * * * *